US009453051B2

(12) United States Patent
Fischer et al.

(10) Patent No.: US 9,453,051 B2
(45) Date of Patent: Sep. 27, 2016

(54) CYCLOSPORIN DERIVATIVES

(75) Inventors: Gunter Fischer, Halle (DE); Miroslav Malesevic, Halle (DE); Frank Erdmann, Halle (DE); Jan Kuhling, Halle (DE); Michael Bukrinsky, Potomac, MD (US); Stephanie Constant, Herndon, VA (US); Gerd Ruhter, Hamburg (DE); Peter Nussbaumer, Dortmund (DE); Klaus Dinkel, Bochum (DE)

(73) Assignees: Max-Planck-Gesellschaft zur Forderung der Wissenschaften e.V., Munich (DE); Lead Discovery Center GmbH, Dortmund (DE)

( * ) Notice: Subject to any disclaimer, the term of this patent is extended or adjusted under 35 U.S.C. 154(b) by 82 days.

(21) Appl. No.: 14/241,126

(22) PCT Filed: Aug. 29, 2012

(86) PCT No.: PCT/EP2012/066726
§ 371 (c)(1),
(2), (4) Date: Apr. 16, 2014

(87) PCT Pub. No.: WO2013/030208
PCT Pub. Date: Mar. 7, 2013

(65) Prior Publication Data
US 2014/0316104 A1 Oct. 23, 2014

(30) Foreign Application Priority Data
Aug. 30, 2011 (DE) .......................... 10 2011 111 991

(51) Int. Cl.
*A61K 38/12* (2006.01)
*C07K 7/50* (2006.01)
*C07K 7/64* (2006.01)
*C12N 9/90* (2006.01)

(52) U.S. Cl.
CPC ............... *C07K 7/645* (2013.01); *C12N 9/90* (2013.01); *C12Y 502/01008* (2013.01)

(58) Field of Classification Search
None
See application file for complete search history.

(56) References Cited

U.S. PATENT DOCUMENTS

| 8,618,065 B2 | 12/2013 | Fischer et al. | |
| 2010/0041747 A1 | 2/2010 | Fischer et al. | |
| 2010/0209390 A1* | 8/2010 | Or | C07K 7/645 424/85.4 |
| 2012/0058932 A1 | 3/2012 | Fischer et al. | |

FOREIGN PATENT DOCUMENTS

| AU | 762963 | 7/2003 |
| WO | 9918120 | 4/1999 |
| WO | 2010-012073 | 2/2010 |

OTHER PUBLICATIONS

International Search Report for PCT/EP2012/066726 mailed on Sep. 28, 2012.
Andrzej Galat. "Peptidylprolyl Cis/Trans Isomerases (Immunophilins): Biological Diversity—Targets—Functions", Current Topics in Medicinal Chemistry, 2003, vol. 3, No. 12, pp. 1315-1347.
Franz X. Schmid. "Prolyl Isomerases", Advances in Protein Chemistry, 2001, vol. 59, pp. 243-282.
Xiaodong J. Wang, et al. "Peptidyl-Prolyl Isomerase Inhibitors", Biopolymers (Peptide Science), 2006, vol. 84, pp. 125-146.
Takafumi Uchida, et al. "Pin1 and Par14 Peptidyl Prolyl Isomerase Inhibitors Block Cell Proliferation", Chemistry & Biology, 2003, vol. 10, Issue 1, pp. 15-24.
Sheng-Hao Chao, et al. "Juglone, an inhibitor of the peptidyl-prolyl isomerase Pin1, also directly blocks transcription", Nucleic Acids Research, 2001, vol. 29, No. 3, pp. 767-773.
Rene Traber, et al. "Isolation and Structure Determination of the New Cyclosporins E, F, G, H, and I", Helvetica Chimica Acta, 1982, vol. 65, Issue 5, No. 162, pp. 1655-1677.
Rene Traber, et al. "Novel Cyclosporins from Tolypocladium inflatum. The Cyclosporins K-Z", Helvetica Chimica Acta, 1987, vol. 70, pp. 13-36.
Jens W. Eckstein, et al. "A new class of cyclosporin analogues for the treatment of asthma", Expert Opinion on Investigational Drugs, 2003, vol. 12, pp. 647-653.
I. Leonard Bernstein, et al. "How Does Auranofin Compare with Methotrexate and Cyclosporin as a Corticosteroid-Sparing Agent in Severe Asthma?", BioDrugs, 1979, vol. 8, No. 3, pp. 205-215.
Shelby P. Umland, et al. "Effects of Cyclosporin A and Dinactin on T-Cell Proliferation, Interleukin-5 Production, and Murine Pulmonary Inflammation", American Journal of Respiratory Cell & Molecular Biology, 1999, vol. 20, pp. 481-492.
N. B. Bouchta, et al. "Conversion From Tacrolimus to Cyclosporin Is Associated With a Significant Improvement of Glucose Metabolism in Patients With New-Onset Diabetes Mellitus After Renal Transplantation", Transplantation Proceedings, 2005, vol. 37, pp. 1857-1860.
Martina Dufer, et al. "Diabetogenic Effect of Cyclosporin A Is Mediated by Interference with Mitochondrial Function of Pancreatic B-Cells", Molecular Pharmacology, 2001, vol. 60, No. 4, pp. 873-879.
K. R. Schultz, et al. "Effect of gastrointestinal inflammation and age on the pharmacokinetics of oral microemulsion cyclosporin A in the first month after bone marrow transplantation", Bone Marrow Transplantation, 2000, vol. 26, pp. 545-551.

(Continued)

*Primary Examiner* — Satyanarayana R Gudibande
(74) *Attorney, Agent, or Firm* — Amin, Turocy & Watson, LLP

(57) ABSTRACT

The present invention relates to novel cyclosporin derivatives that do not cross the cellular membrane. The compounds according to the invention are used in medicine, more particularly in the treatment/diagnosis of acute and chronic inflammatory diseases, viral infections, cancer, degenerative muscle diseases, neurodegenerative diseases and damage that is associated with calcium homeostasis impairment. The novel cyclosporin derivatives additionally have no immunosuppressive effect.

8 Claims, 6 Drawing Sheets

(56) References Cited

OTHER PUBLICATIONS

Kazuhiko Arimori, et al. "Effect of P-Glycoprotein Modulator, Cyclosporin A, on the Gastrointestinal Excretion of Irinotecan and Its Metabolite SN-38 in Rats", Pharmaceutical Research, vol. 20, No. 6, Jun. 2003, pp. 910-917.

Laurent Mascarell, et al. "Cyclosporin A therapy differently affects immunological-relevant gene expression following immunization", Immunology Letters, 2002, vol. 84, pp. 137-143.

T. Z. Sukkar, et al. "Gingival fibroblasts grown from cyclosporin-treated patients show a reduced production of matrix metalloproteinase-1 (MMP-1) compared with normal gingival fibroblasts, and cyclosporin downregulates the production of MMP-1 stimulated by pro-inflammatory cytokines", Journal of Periodontal Research, 2007, vol. 42, pp. 580-588.

M. Odaka, et al. "Intractable chronic inflammatory demyelinating polyneuropathy treated successfully with ciclosporin", Journal of Neurology, Neurosurgery & Psychiatry, 2005, vol. 76, pp. 1115-1120.

Eduardo Monguilhott Dalmarco, et al. "Additional evidence of acute anti-inflammatory effects of cyclosporin A in a murine model of pleurisy", Transplant Immunology, 2004, vol. 12, pp. 151-157.

Jesper Melchior Hansen, et al. "Effects of nitric oxide blockade and cyclosporin A on cardiovascular and renal function in normal man", Journal of Hypertension, 1999, vol. 17, No. 12, pp. 1707-1713.

M. R. Rao, et al. "Changes in the Cardiovascular Nitric Oxide Pathway in Cyclosporin-A Treated Rats", Drug & Chemical Toxicology, 1998, vol. 21, pp. 27-34.

Erdem A. Ozkisacik, et al. "Effects of Cyclosporin A on Neurological Outcome and Serum Biomarkers in the Same Setting of Spinal Cord Ischemia Model", Annals of Vascular Surgery, 2006, vol. 20, No. 2, pp. 243-249.

Roos Van Westrhenen, et al. "Cyclosporin A Induces Peritoneal Fibrosis and Angiogenesis during Chronic Peritoneal Exposure to a Glucose-Based, Lactate-Buffered Dialysis Solution in the Rat", Blood Purification, 2007, vol. 25, pp. 466-472.

C. Wilasrusmee, et al. "Angiocidal effect of Cyclosporin A: a new therapeutic approach for pathogenic angiogenesis", International Angiology, 2005, vol. 24, No. 4, pp. 372-379.

A. J. Quesada, et al. La ruta de señalización CA++/ Calcineurina/ NFAT en activación endotelial y angiogénesis: efectos de la ciclosporina A, Nefrología, 2003, vol. 23, No. 3, pp. 44-48.

N. Duncan, et al. Optimizing the use of cyclosporin in allogeneic stem cell transplantation, Bone Marrow Transplantation, 2006, vol. 38, pp. 169-174.

Michael Winkler. "Cyclosporin as Baseline Immunosuppression in Solid Organ Transplantation", BioDrugs, 2000, vol. 14, No. 3, pp. 185-193.

Ashok B. Jain, et al. "Cyclosporin and Tacrolimus in Clinical Transplantation, A Comparative Review", Clinical Immunotherapeutics, 1996, vol. 5, pp. 351-373.

Jan G. M. C. Damoiseaux, et al. "Short Analytical Review: Multiple Effects of Cyclosporin A on the Thymus in Relation to T-Cell Development and Autoimmunity", Clinical Immunology and Immunopathology, 1997, vol. 82, No. 3, pp. 197-202.

G. S. Panayi, et al. "The Use of Cyclosporin A Microemulsion in Rheumatoid Arthritis: Conclusions of an International Review", British Journal of Rheumatology, 1997, vol. 36, pp. 808-811.

Giampiero Pasero, et al. "Risks and Benefits of Low-Dosage Cyclosporin in Rheumatoid Arthritis—Emerging Evidence of a Therapeutic Role", BioDrugs, 1997, vol. 7, Issue 5, pp. 376-385.

Jean Steffan, et al. "A systematic review and meta-analysis of the efficacy and safety of cyclosporin for the treatment of atopic dermatitis in dogs", Veterinary Dermatology, 2006, vol. 17, pp. 3-16.

John Berth-Jones. "The use of ciclosporin in psoriasis", Journal of Dermatological Treatment, 2005, vol. 16, pp. 258-277.

Ulrich Mrowietz. Vorstellungen zum Wirkmechanismus von Ciclosporin bei der Psoriasis : Eine Übersicht mit Richlinien zur Therapie (New findings on the mode of action of Ciclosporin in psoriasis. A review with guidelines for therapy), Hautarzt, 1993, vol. 44, pp. 353-360.

Luciano P. Bellini, et al. "Letter to the Editor" regarding published article "Topical Cyclosporin A in Severe Allergic Conjunctivities" with response by Altan A. Ozcan, et al., Cornea, 2008, vol. 27, No. 5, p. 625.

C. Noli, et al. "Prospective open pilot study on the use of ciclosporin for feline allergic skin disease", Journal of Small Animal Practice, 2006, vol. 47, pp. 434-438.

Atsuki Fukushima, et al. Cyclosporin A inhibits eosinophilic infiltration into the conjunctiva mediated by type IV allergic reactions, Clinical & Experimental Ophthalmology, 2006, vol. 34, pp. 347-353.

C. Guillen, et al. "Regulatory Effects of Cytokines and Cyclosporine A on Peripheral Blood Mononuclear Cs from Stable Multiple Sclerosis Patients", Immunopharmacology and Immunotoxicology, 1999, vol. 21, No. 3, pp. 527-549.

Guo Jun Zhao, et al. "Clinical and Magnetic Resonance Imaging Changes Correlate in a Clinical Trial Monitoring Cyclosporine Therapy for Multiple Sclerosis", Journal of Neuroimaging, 1997, vol. 7, No. 1, pp. 1-7.

Bradley G. Leshnower, et al. "Cyclosporine Preserves Mitochondrial Morphology After Myocardial Ischemia/ Reperfusion Independent of Calcineurin Inhibition", Annals of Thoracic Surgery, 2008, vol. 86, pp. 1286-1292.

J. R. Xie, et al. "Cardioprotective effects of cyclosporine A in an in vivo model of myocardial ischemia and reperfusion", Acta Anaesthesiologica Scandinavica, 2007, vol. 51, pp. 909-913.

Thilo Hackert, et al. "Ciclosporin Aggravates Tissue Damage in Ischemia Reperfusion-Induced Acute Pancreatitis", Pancreas, 2006, vol. 32, No. 2, pp. 145-151.

Gokhan Akdemir, et al. "Therapeutic efficacy of intraventricular cyclosporine A and methylprednisolone on a global cerebral ischemia model in rats", Neurological Research, 2005, vol. 27, No. 8, pp. 827-834.

Lars Pape, et al. "Letter regarding Cyclosporin A-induced remission of primary membranous glomerulonephritis in a child", Nephrology Dialysis Transplantation, 2004, vol. 19, p. 3207.

Takahiro Kiyomasu, et al. "Cyclosporin A Treatment for Membranoproliferative Glomerulonephritis Type II", Nephron, 2002, vol. 91, pp. 509-511.

Brian C. Wulff, et al. "Sirolimus Reduces the Incidence and Progression of UVB-Induced Skin Cancer in SKH Mice even with Co-administration of Cyclosporine A", Journal of Investigative Dermatology, 2008, vol. 128, pp. 2467-2473.

Sumudra Periyasamy, et al. "The Immunophilin Ligands Cyclosporin A and FK506 Suppress Prostate Cancer Cell Growth by Androgen Receptor-Dependent and-Independent Mechanisms", Endocrinology, 2007, vol. 148, No. 10, pp. 4716-4726.

L. M. Pilarski, et al. "Drug resistance in multiple myeloma: cyclosporin A analogues and their metabolites as potential chemosensitizers", Leukemia, 1998, vol. 12, pp. 505-509.

Peter H. Wiernik, et al. "Objective Response of Multiple Myeloma to Cyclosporin A", Leukemia & Lymphoma, 1994, vol. 16, pp. 167-170.

Apostolia M. Tsimberidou, et al. "Mylotarg, fludarabine, cytarabine (ara-C), and cyclosporine (MFAC) regimen as post-remission therapy in acute myelogenous leukemia", Cancer Chemotheraphy & Pharmacology, 2003, vol. 52, pp. 449-452.

Apostolia Tsimberidou, et al. "Gemtuzumab, Fludarabine, Cytarabine, and Cyclosporine in Patients with Newly Diagnosed Acute Myelogenous Leukemia or High-Risk Myelodysplastic Syndromes", Cancer, 2003, vol. 97, No. 6, pp. 1481-1487.

Luigi Rodella, et al. "Cyclosporine-A Delays the End-Plate Degeneration in Denerved Rat Muscles", Neuroscience Research Communications, 2002, vol. 31, No. 2, pp. 85-92.

S. Von Haehling, et al. "C achexia: a therapeutic approach beyond cytokine antagonism", International Journal of Cardiology, 2002, vol. 85, pp. 173-183.

Elisabetta Ravot, et al. "New Uses for Old Drugs in HIV Infection—The Role of Hydroxyurea, Cyclosporin and Thalidomide", Drugs, 1999, vol. 58, No. 6, pp. 953-963.

(56) References Cited

OTHER PUBLICATIONS

G. J. Carroll, Letter to the Editor regarding "Effective control of incomplete reactive arthritis with cyclosporin", Rheumatology, 2001, vol. 40, pp. 945-947.

Shuichi Tsuruoka, et al. "Dosing time-dependent variation of bone resorption by cyclosporin A in rats' femurs", European Journal of Pharmacology, 2007, vol. 564, pp. 226-231.

Emmanuel M. Awumey, et al. "Molecular and Functional Evidence for Calcineurin-A a and b Isoforms in the Osteoclast: Novel Insights into Cyclosporin A Action on Bone Resorption", Biochemical & Biophysical Research Communications, 1999, vol. 254, pp. 248-252.

Kun Ping Lu, et al. "Prolyl cis-trans isomerization as a molecular timer", Nature Chemical Biology, 2007, vol. 3, No. 10, pp. 619-629.

S. Barik. "Immunophilins: for the love of proteins", Cellular and Molecular Life Sciences, 2006, vol. 63, No. 24, pp. 2889-2900.

David S. Cassarino, et al. "Cyclosporin A Increases Resting Mitochondrial Membrane Potential in SY5Y Cells and Reverses the Depressed Mitochondrial Membrane Potential of Alzheimer's Disease Cybrids", Biochemical and Biophysical Research Communications, 1998, vol. 248, pp. 168-173.

Quanbao Wang, et al. "Injection of bradykinin or cyclosporine A to hippocampus induces Alzheimer-like phosphorylation of Tau and abnormal behavior in rats", Chinese Medical Journal, 2002, vol. 115, No. 6, pp. 884-887.

Sean Dobson, et al. "Characterization of protein Ser:Thr phosphatases of the malaria parasite, *Plasmodium falciparum*: inhibition of the parasitic calcineurin by cyclophilin-cyclosporin complex", Molecular and Biochemical Parisitology, 1999, vol. 99, pp. 167-181.

Hiroyuki Iwamura, et al. "Comparative Study of Glucocorticoids, Cyclosporine A, and JTE-607 [( )-Ethyl-N-{3,5-dichloro-2-hydroxy-4-[2-(4-methylpiperazin-1-yl)ethoxy]benzoyl}-L-phenylalaninate Dihydrochloride] in a Mouse Septic Shock Model", The Journal of Pharmacology & Experimental Therapeutics, 2004, vol. 311, No. 3, pp. 1256-1263.

H. K. Bell, et al. "Letter Regarding Use of basiliximab as a cyclosporin-sparing agentin palmoplantar pustular psoriasis with myalgia as an adverse effect", British Journal of Dermatology, 2002, vol. 147, pp. 606-607.

Erik De Clercq. "Emerging antiviral drugs", Expert Opinion on Emerging Drugs, 2008, vol. 13, pp. 393-416.

Michael M. Lederman, et al. "Cyclosporin A Provides No Sustained Immunologic Benefit to Persons with Chronic HIV-1 Infection Starting Suppressive Antiretroviral Therapy: Results of a Randomized, Controlled Trial of the AIDS Clinical Trials Group A5138", Journal of Infectious Diseases, 2006, vol. 194, pp. 1677-1685.

Markus Thali. "Cyclosporins: immunosuppressive drugs with anti-HIV-1 activity", Molecular Medicine Today, 1995, vol. 1, pp. 287-291.

Hideya Kawasaki, et al. "Cyclosporine Inhibits Mouse Cytomegalovirus Infection via a Cyclophilin-Dependent Pathway Specifically in Neural Stem/Progenitor Cells", Journal of Virology, 2007, vol. 81, No. 17, pp. 9013-9023.

D. Bohringer, et al. "Cyclosporin-A-Augentropfen bei Nummuli nach Adenovirus-Keratokonjunktivitis", Ophthalmologe, 2008, vol. 105, pp. 592-594.

T. Reinhard, et al. "Lokales Cyclosporin A bei Nummuli nach Keratoconjunctivitis epidemica", Ophthalmologe, 2000, vol. 97, pp. 764-768.

Anat Gafter-Gvili, et al. "Cyclosporin A-induced hair growth in mice is associated with inhibition of hair follicle regression", Archives of Dermatological Research, 2004, vol. 296, No. 6, pp. 265-269.

J. L. Schmutz, et al. "Nouveaux effets secondaires de la ciclosporine sur les phanères", Annales de Dermatologie et de Vénéréologie, 2000, vol. 127, p. 769.

Feng Wang, et al. "Synthesis and Peptidyl-Prolyl Isomerase Inhibitory Activity of Quinoxalines as Ligands of Cyclophilin A", Chemical & Pharmaceutical Bulletin, 2006, vol. 54, No. 3, pp. 372-376.

Jolanta M. Dzik, et al. "Effect of cyclosporin A on immunological response in lungs of guinea pigs infected with Trichinella spiralis", Acta Biochimica Polinica, 2002, vol. 49, No. 1, pp. 233-247.

Dean C. S. Tai, et al. "Correction of motion artifact in transmembrane voltage-sensitive fluorescent dye emission in hearts", American Journal of Physiology Heart and Circulatory Physiology, 2004, vol. 287, pp. 985-993.

Andrey Gurachevsky, et al. "Application of spin label electron paramagnetic resonance in the diagnosis and prognosis of cancer and sepsis", Clinical Chemistry and Laboratory Medicine, 2008, vol. 46, No. 9, pp. 1203-1210.

Aki Yamada, et al. "Usefulness and Limitation of DiBAC4(3), a Voltage-Sensitive Fluorescent Dye, for the Measurement of Membrane Potentials Regulated by Recombinant Large Conductance $Ca^{2+}$-Activated $K^+$ Channels in HEK293 Cells", Japan Journal of Pharmacology, 2001, vol. 86, pp. 342-350.

\* cited by examiner

Fig. 1
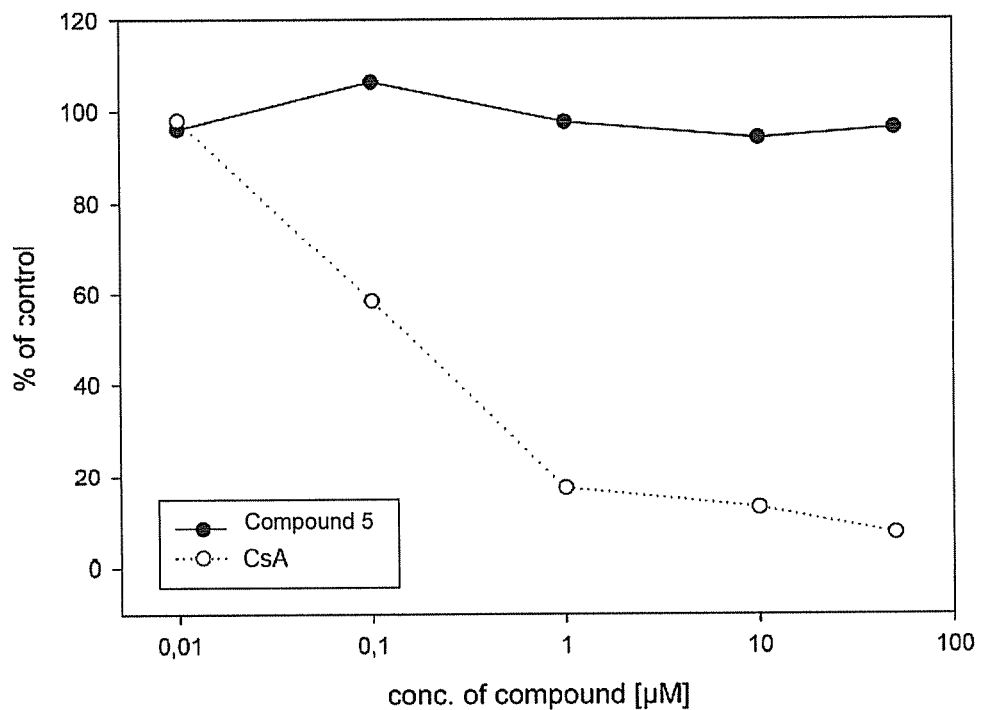
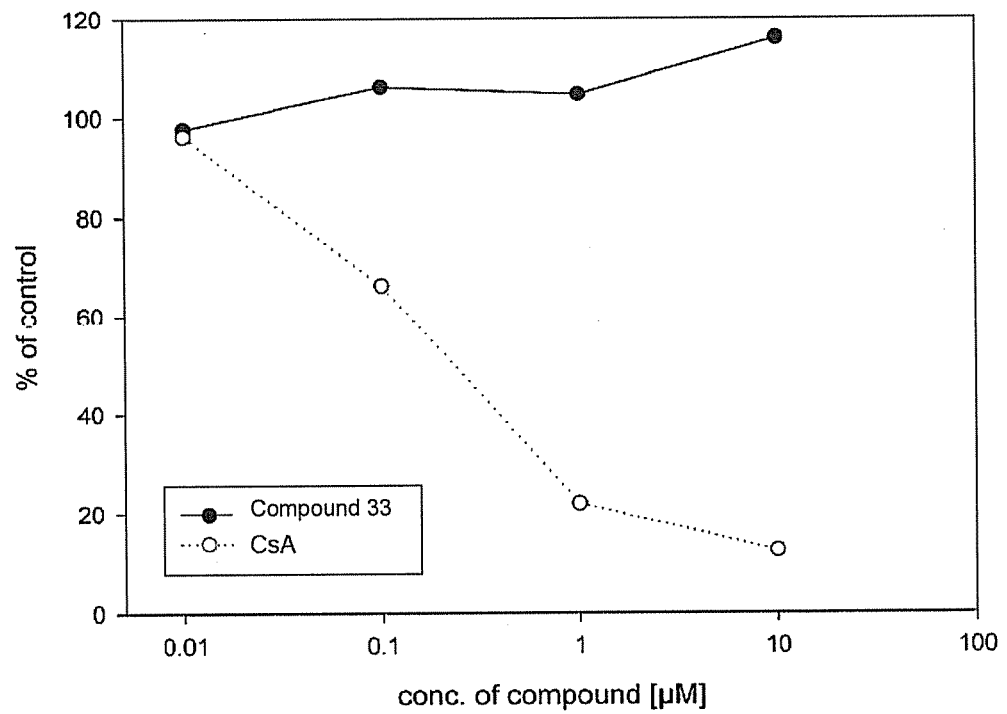

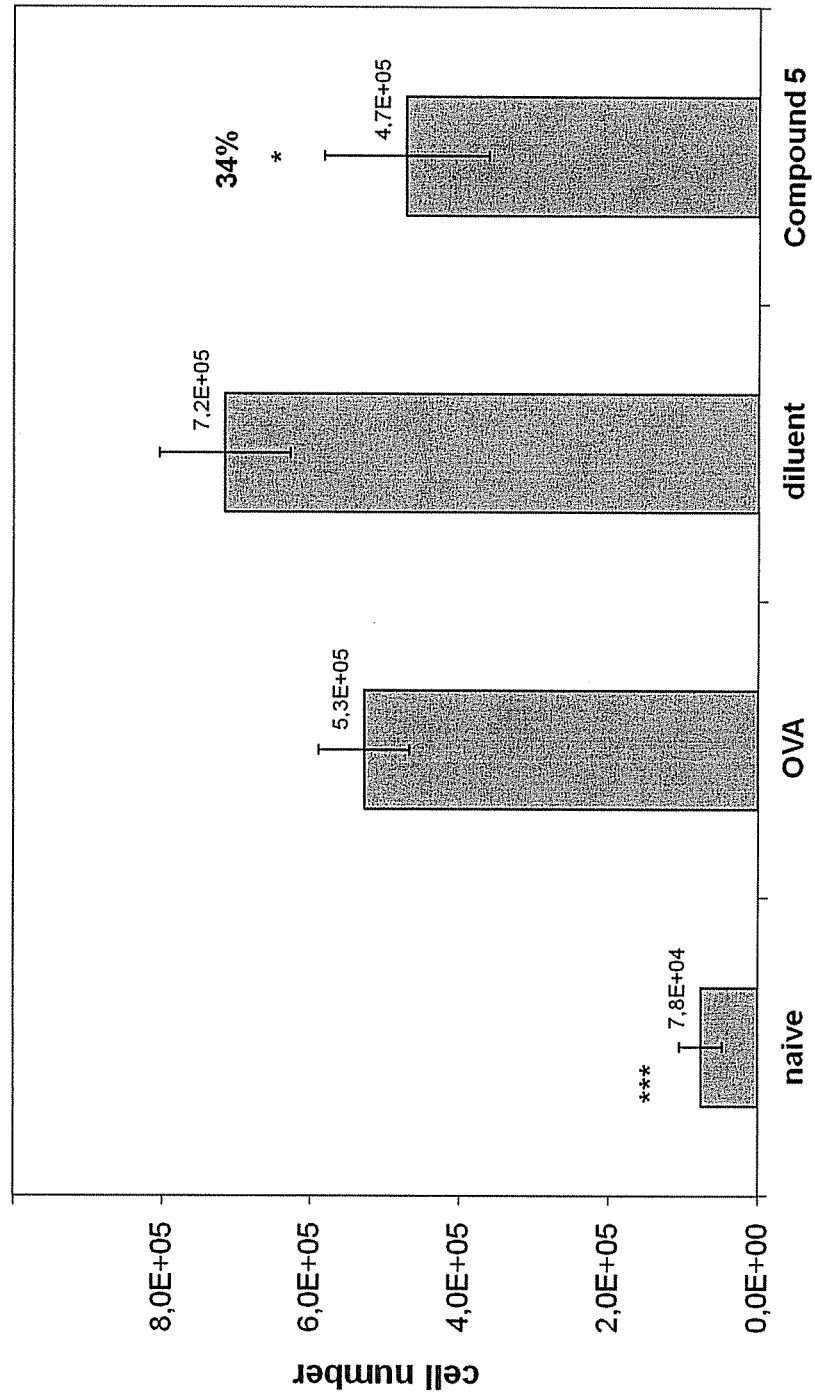

CYCLOSPORIN DERIVATIVES

The present invention is directed to compounds of formula I shown below and tracer-coupled compounds, which are both cyclosporin derivatives. The compounds according to the present invention show no immunosuppressive effect and are used in medicine, in particular in the treatment of diseases like viral infections, inflammatory diseases, cancer, degenerative muscles diseases, neurodegenerative diseases and damages that are associated with impairment of calcium homeostasis. Furthermore, the present invention is directed to a pharmaceutical composition containing a compound according to the present invention and optionally different additives. The present invention is furthermore directed to a method of accumulation of active agents in an extracellular space of a multi-cellular object. A further objective of the present invention is the use of various cyclosporin derivatives for the preparation of compounds according to the present invention.

Biologically active molecules, so-called "active agents", which are in general pharmaceutically active agents, have their effect mostly inside as well as outside of biological cells. Thereby, the problem especially emerged so far is that active agents, which should have their effects only inside the cell are causing unwanted side effects in the extracellular space already prior to their transfer through the cell membrane. At this arises the additional problem that one and the same active agent can have different effects inside and outside of the cell. The actual effect comprises therefore two components—the desired intracellular effect and the undesired extracellular effect. To achieve the intracellular effect, often also the extracellular (side) effects have necessarily to be accepted—since the transport to the cell includes normally crossing an extracellular space.

Equally, only the extracellular effect can be desired and the intracellular effect can be undesired. Especially in medicine, various active agents are known that not only do not cause the desired effect in the cell, but are even toxic or cause an otherwise harmful effect. It comes along that a far higher dose than is actually needed has to be applied for achieving a specific, extracellular effect to compensate for the "loss" of active agents migrated into the cell.

Active agents can affect molecules or structures extracellularly and/or intracellularly. Such biological molecules could for example be enzymes, inhibitors, activators or receptors. "Structures" for example can be understood as extracellular matrix, consisting of the entirety of macromolecules, which are located outside of the plasma membrane of cells in tissues and organs.

Various publications show that cyclosporins can have intracellular as well as extracellular effects. Cyclosporins can bind intracellularly as well as extracellularly to proteins, like cyclophilins. These proteins are comprehensively described in the scientific and patent literature, such as for example in WO 2010/012073. Cyclosporins and their derivatives have a variety of effects which may be used therapeutically. Thus, they may influence neuroprotection/neurogeneration, chaperon activity, HIV-infection, cancer or Alzheimer's disease. An example for a desired effect of these compounds is the PPlase-inhibition. Although, the PPlase(peptidyl-prolyl-isomerase)-inhibitors could differentiate between the individual PPlase-families ((Nature Chemical Biology. 3(10):619-29, 2007; Cellular & Molecular Life Sciences. 63 (24):2889-900, 2006; Current Topics in Medicinal Chemistry. 3(12):1315-47, 2003; Advances in Protein Chemistry. 59:243-82, 2001) they have often similar inhibitive strength in view of sequence-similar family members. As PPlases within one family can influence different biochemical reactions, the diagnostic or pharmacological effect of applied active agents depends directly on the concentration achieved in different distribution spaces. Thus, for example, some of these PPlase-inhibitors (e.g. Biopolymers 84(2006)125-146; Chemical & Pharmaceutical Bulletin. 54 (3):372-376, 2006; Chemistry & Biology. 10 (1):15-24, 2003; Nucleic Acids Research. 29(3):767-773, 2001), such as the therapeutically used cyclosporin A, are only slightly soluble in water (DE 19859910).

Cyclosporin A originally isolated from the fungi *Tolypocladium inflatum* is for example used in medical applications for suppression of immune responses. Cyclosporins, in terms of this invention, are cyclic peptides of 11 amino acids (undecapeptides). All cyclosporins A to I, as well as their derivatives as described in Helvetica Chimica Acta 65 (1982), 1655-1677 and all cyclosporins K to Z as well as their derivatives as described in Chimica Acta 70 (1987), 13-36 are included. The cyclosporins may according to the invention also—as described in WO 99/18120—be deuterated.

Cyclosporin A (also Ciclosporin) is a cyclic oligopeptide, which has intracellularly a calcineurin-inhibiting effect. A cyclosporin, effective as such, is characterized by a selective and reversible mechanism of immunosuppression. It blocks selectively the activation of T-lymphocytes by production of certain cytokines, which participate in the regulation of these T-cells. Thereby, particularly, the synthesis of interleukin-2 is inhibited causing in parallel that the proliferation of cytotoxic T-lymphocytes, which for example are responsible for rejection of foreign tissue, is suppressed. The cyclosporin takes effect intracellularly by binding to the so called cyclophilins or immunophilins, which belong to the family of cyclosporin-binding proteins. According to the present invention, it is preferred that the compounds of the invention do not have this intracellular effect.

Inhibitors of cyclophilins have a very wide therapeutic range, such as, for example the treatment of diseases of the respiratory tract, like e.g. asthma, chronic obstructive pulmonary disease (COPD), pneumonia or emphysema (Expert Opinion on Investigational Drugs 12(2003)647-653, Biodrugs 8(1997) 205-215, American Journal of Respiratory Cell & Molecular Biology 20(1999)481-492), metabolic diseases, like diabetes (Transplantation Proceedings 37(2005) 1857-1860, Molecular Pharmacology 60(2001)873-879), inflammatory diseases of the digestive tract (Bone Marrow Transplantation 26(2000):545-551, Pharmaceutical Research 20(2003)910-917), disorders of the immune system (Immunology Letters 84(2002)137-143, Acta Biochimica Polonica 49(2002)233-247) inflammations (Journal of Periodontal Research 42(2007)580-588, Journal of Neurology, Neurosurgery & Psychiatry 76(2005)1115-1120, Transplant Immunology 12(2004):151-157), cardiovascular diseases (Journal of Hypertension 17(1999)1707-1713, Drug & Chemical Toxicology 21(1998)27-34), neurological diseases (Annals of Vascular Surgery. 20(2006) 243-249), diseases that are associated with dysfunction of angiogenesis (Blood Purification. 25 (2007) 466-472, International Angiology 24 (2005) 372-379, Nefrologia. 23(2003):44-48), for suppression of the immune response in case of organ transplantation (Bone Marrow Transplantation. 38 (2006) 169-174), Biodrugs. 14 (2000) 185-193, Clinical Immunotherapeutics. 5 (1996) 351-373) and of autoimmune diseases (Immunology & Immunopathology. 82(3):197-202, 1997), arthritic diseases (British Journal of Rheumatology. 36(1997)808-811, Biodrugs. 7 (1997) 376-385), dermatitis (Veterinary Dermatology 17 (2006) 3-16), psoriasis (Journal of Dermatological Treatment 16(2005)258-277, Hautarzt 44 (1993) 353-360), in allergies (Cornea 27 (2008) 625, Journal of Small Animal Practice 47(2006)434-438, Clinical & Experimental Ophthalmology 34(2006)347-353), for multiple sclerosis (Immunopharmacology & Immunotoxicology 21(1999)527-549, Journal of Neuroimaging 7(1997)1-7), diseases caused by ischemia such as e.g. cardiac infarction (Annals of Thoracic Surgery 86(2008)1286-1292, Acta Anaesthesiologica Scandinavica 51(2007)+909-913), infarction of the pancreas (Pancreas 32 (2006) 145-151) or stroke (Annals of Vascular Surgery 20(2006)243-249, Neurological Research 27(2005)827-834), kidney diseases such as e.g. glomerulonephritis (Nephrology Dialysis Transplantation 19(2004)3207, Nephron 91(2002)509-511), tumors (Journal of Investigative Dermatology 128(2008)2467-2473, Endocrinology 148(2007)4716-4726), for multiple myeloma (Leukemia 12 (1998) 505-509, Leukemia & Lymphoma 16(1994)167-170), for acute or chronic leukemia (Cancer Chemotherapy & Pharmacology 52 (2003) 449-452, Cancer 97 (2003) 1481-1487), muscle degeneration (Neuroscience Research Communications 31(2002)85-92, cachexia (International Journal of Cardiology 85(2002)173-183, Drugs 58 (1999) 953-963, 1999), Reiter's syndrome (Rheumatology 40(2001)945-947), diseases of bone resorption (European Journal of Pharmacology 564(2007)226-231, Biochemical & Biophysical Research Communications 254(1999)248-252), in Alzheimer's disease (Biochemical & Biophysical Research Communications 248 (1998) 168-173, Chinese Medical Journal 115 (2002) 884-887), malaria (Molecular & Biochemical Parasitology 99(1999)167-181), septic and toxic shock syndrome (Journal of Pharmacology & Experimental Therapeutics 311(2004)1256-1263), myalgia (British Journal of Dermatology 147(2002)606-607), in viral infection (Expert Opinion on Emerging Drugs 13 (2008) 393-416) such as e.g. HIV-1, HIV-2, HIV-3 (Journal of Infectious Diseases 194(2006)1677-1685, Molecular Medicine Today 1 (1995) 287-291, 1995), cytomegaloviruses (Journal of Virology 81(2007)9013-9023) or adenoviruses (Ophthalmologe 105 (2008) 592-594, Ophthalmologe 97 (2000) 764-768) and for supporting hair growth (Archives of Dermatological Research 296 (6): 265-269, 2004, Annales de Dermatologie et de Venereologie 127(2000) 769). Based on the wide range of therapeutically application, they are an important substance class in medicine.

If cyclosporins and their derivatives are used for the treatment of said diseases, then they have in addition to the desired therapeutic effect, immunosuppressive effects, which is a drawback of many so far known cyclosporin derivatives. In these cases, however, the immunosuppressive effect is an undesired side effect which should be eliminated. It is known that cyclosporins and their derivatives are able to inhibit cyclophilins. But, if the cyclosporin compounds enter the cell, then the complexes of cyclosporin compounds and cyclophilin may inhibit the serine-threonine-phosphatase calcineurin. The inhibition of calcineurin induces then the undesired side effect of immunosuppression. But, there exists also cyclophilins in the extracellular space whose inhibition by cyclosporin compounds induces desired therapeutic effects. Therefore, if it is possible to provide cyclosporin compounds which show both an effect in regard to the desired therapeutic purpose and are not able to enter cells, then the undesired side effects could be avoided.

Thus, it was the objective if the present invention to provide novel cyclosporin derivatives, which have the desired therapeutic effects without occurrence of the side effect of immunosuppression. Particularly; it was the objective of the present invention to provide active agents, which are therapeutically effective, but cannot enter into the cell.

Especially, it was one objective of the present invention to provide active agents which are therapeutically effective against the following diseases without being immunosuppressive:
 a) viral infection
 b) acute and chronic inflammatory diseases
 c) cancer
 d) degenerative muscle diseases
 e) neurodegenerative diseases, and
 f) disorders, which are associated with an impairment of calcium homeostasis,
wherein the viral infection can be caused by viruses such as HIV, hepatitis A, hepatitis B, hepatitis C, hepatitis D, and hepatitis E,
wherein the inflammatory disease includes preferably asthma, chronic inflammations, chronic prostatitis, glomerulonephritis, multiple chemical sensitivity, inflammatory intestinal diseases, sepsis, inflammation of the vascular smooth muscle cells, aneurysm, inflammation in the pelvic area, reperfusion injury, rheumatoid arthritis, vasculitis, psoriasis, and ulcerative colitis,
wherein the cancer disease preferably comprises lung cancer, cancer of the bladder, hepatic cancer, pancreatic cancer, and breast cancer,
wherein the degenerative muscle disease is preferably directed to muscle dystrophy, collagen IV-myopathies, and the myocardial reperfusion injury,
wherein the neurodegenerative disease is preferably selected from Alzheimer's disease, Parkinson's disease, Huntington's disease, multiple systemic atrophy, multiple sclerosis, cerebral poliomyelitis, stroke, diabetic neuropathy, amyotrophic lateral sclerosis, spinal cord injuries, and cerebral sclerosis,
wherein the disease associated with an impairment of calcium homeostasis, refers preferably to myocardial infarct, stroke, acute hepatic toxicity, cholestasis, and reperfusion injury of transplanted organs, and Surprisingly, it has been found that the derivatization of amino acid 1 of cyclosporins with suitable imidazole, oxazole, or thiazole derivatives may change their features in a way that such changed cyclosporins have modified cell permeability. In particular introducing chemical groups in the abovementioned imidazole, oxazole, or thiazole derivatives according to the invention, such as e.g. an acid group, may change the features of the cyclosporins in a way that they do not accumulate in the extracellular space and do not enter into the cells.

An essential feature, which is obtained by derivatization of cyclosporins with suitable imidazole, oxazole, or thiazole derivatives, is the ability of the novel cyclosporin-derivatives obtained in such a way to inhibit furthermore the peptidyl-prolyl-cis/trans-isomerase activity of human cyclophilins, preferably with an $IC_{50}$ value of <100 nMol without inhibiting thereby the serine-threonine-phosphatase calcineurin and without entering into the cells.

The above mentioned objective is accomplished by the provision of compounds of the following formula I:

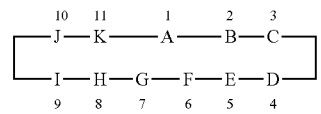

Formula I wherein A is an amino acid of the following formula H,

Formula II

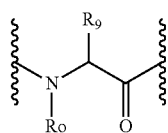

where the bonds that end at the wavy lines represent linkages to the moieties B and K and $R_9$ is a group of the following formula III, and Formula III

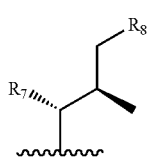

in which $R_8$ corresponds to a group of the following formula IV, or

Formula IV

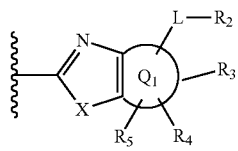

in which $R_8$ corresponds to a group of the following formula V, or

Formula V

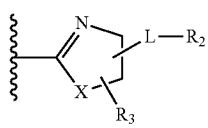

in which $R_8$ corresponds to a group of the following formula VI, or

Formula VI

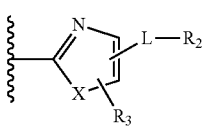

in which $R_8$ corresponds to a group of the following formula VII, or

Formula VII

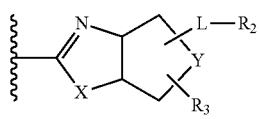

in which $R_8$ corresponds to a group of the following formula VIII, wherein the residues L-$R_2$ and $R_3$ can be bound to the same or different phenyl rings, or Formula VIII

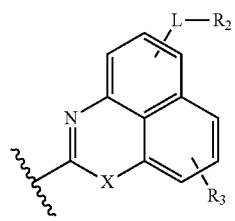

in which $R_8$ corresponds to a group of the following formula IX, and wherein the residues L-$R_2$ and $R_3$ can be bound to the same or different rings $Q_2$ or $Q_3$, or Formula IX

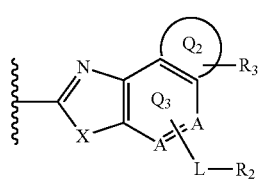

in which $R_8$ corresponds to a group of the following formula X, wherein the residues L-$R_2$ and $R_3$ can be bound to the same or different rings $Q_2$ or $Q_3$, or Formula X

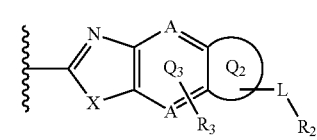

in which $R_8$ corresponds to a group of following formula XI, wherein the residues L-$R_2$ and $R_3$ can be bound to the same or different rings $Q_2$ or $Q_3$, or Formula XI

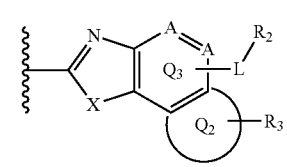

in which $R_8$ corresponds to a group of the following formula XII, wherein the residues L-$R_2$ and $R_3$ can be bound to the same or different phenyl rings, or Formula XII

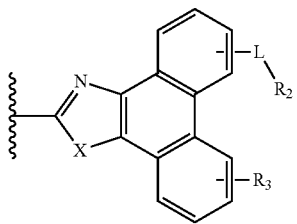

in which $R_5$ corresponds to a group of following formula XIII,

Formula XIII

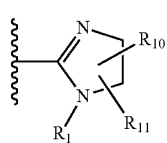

wherein
the bonds in the formulae IV to XIII that end at the wavy lines bind to the $CH_2$— group of formula III on which $R_8$ is linked;
wherein
the group of formula II is covalently bound by its CO to the alpha-amino acid B in formula I via formation of an amide bond and the N—$R_0$ in formula II is covalently bound to a carboxyl group of K via formation of an amide bond, wherein
  B is an amino acid selected from the following group:
  alpha-aminobutanoic acid;
  alanine;
  threonine;
  valine;
  norvaline; and
  alpha-aminobutanoic acid, alanine, threonine, valine, or norvaline with a hydroxyl group modified side chain;
  C represents sarcosine;
  D is an amino acid selected from the following group:
  leucine;
  N-methylleucine;
  valine;
  gamma-hydroxy-N-methylleucine; and
  gamma-hydroxyleucine;
  E is an amino acid selected from the following group:
  valine;
  norvaline; and
  a modified valine or norvalin having one of the carbon atoms of the side chain substituted with a hydroxyl group;
  F is an amino acid selected from the following group:
  leucine,
  N-methylleucine;
  gamma-hydroxy-N-methylleucine; and
  gamma-hydroxyleucine;
  G is alpha-aminobutanoic acid or alanine;
  H is D-alanine or D-serine;
  I and J are amino acids, which are independently of each other selected from the following group:
  leucine;
  N-methylleucine;
  gamma-hydroxy-N-methylleucine; and
  gamma-hydroxyleucine;
  K is N-methylvaline or valine;

wherein
the amino acids B to K are linked to each other via formation of amide bonds;
wherein
the used symbols and indices have the following meanings:
  X represents O, S, or N—$R_1$;
  Y represents O, S, N—$R_1$, —$CH_2$— or —$CH_2CH_2$—;
  A represents CH or N;
  L represents a bond, —$CH_2$—, —$CH_2CH_2$—, —$CH_2CH_2CH_2$—, —$CH_2CH_2CH_2CH_2$—, —CH=CH—, —CH=CHCH$_2$—, —$CH_2$CH=CH—, —$CH_2CH_2$CH=CH—, —$CH_2$CH=CHCH$_2$—, —CH=CHCH$_2CH_2$, —OCH$_2$—, —OCH$_2CH_2$—, —OCH$_2CH_2CH_2$—, —OCH$_2$CH=CH—, —CONH—, —CONHCH$_2$— —CONHCH$_2CH_2$—, —CONHCH$_2CH_2OCH_2CH_2$—, —CONHCH$_2CH_2OCH_2CH_2OCH_2CH_2$—;
  $Q_1$ represents together with the two atoms of the adjacent rings an aromatic or heteroaromatic ring from the group benzene, pyridine, pyrimidine, pyridazine, pyrazine, triazine, thiophene, furan, pyrrole, thiazole, isothiazole, oxazole, isoxazole, imidazole, pyrazole;
  $Q_2$ represents together with the two atoms of the adjacent rings an aromatic or heteroaromatic ring from the group benzene, pyridine, pyrimidine, pyridazine, pyrazine, triazine, thiophene, furan, pyrrole, thiazole, isothiazole, oxazole, isoxazole, imidazole, pyrazole, thiadiazole, oxadiazole, triazole;
  $Q_3$ designates each six membered ring in the middle of which it is positioned;
  $R_0$ represents H or $CH_3$;
  $R_1$ represents H, (C1-C4)-alkyl or benzyl that can also be substituted with a —COOH group;
  $R_2$ represents a polar deprotonizable group $P_s$, or a group $P_s'$ that under physiological conditions can be converted to the group $P_s$, or a polar protonizable group $P_b$, or a group $P_b'$ that under physiological conditions can be converted to the group $P_b$;
  $R_3$ represents H, (C1-C6)-alkyl, (C1-C6)-alkoxy, —OH, (C1-C6)-alkylthio, (C1-C6)-alkylsulfonyl, —SH, —$CF_3$, —COOH, —COO((C1-C6)alkyl), —$CONH_2$, —CONH((C1-C6)alkyl), —CON((C1-C6)alkyl)$_2$, nitro, halogen, cyano, amino, (C1-C6)alkyl-amino, (C1-C6)dialkyl-amino; $R_3$ can also be in the form of a free electron pair, in particular, if $R_3$ binds to a heteroatom of the ring $Q_1$, $Q_2$ or $Q_3$,
  $R_4$ and $R_5$ are independently of each other H, (C1-C6)-alkyl, (C1-C6)-alkoxy, —$CF_3$, halogen or if $R_4$ and $R_5$ are situated on the ring in ortho position, then they can form together a —OCH$_2$O— or a —OCH$_2CH_2$O— group; $R_4$ and $R_5$ can also independently of each other be in the form of a free electron pair; in particular, if $R_4$ or $R_5$ binds to a heteroatom of the ring $Q_1$,
  $R_7$ represents H, —OH, —OCOOR$_{12}$, —OCOR$_{13}$, —OCONR$_{14}R_{15}$, —O-(tetrahydropyran-2-yl), —O-(tetrahydrofuran-2-yl), —O—CHR$_{16}$—OR$_{17}$, —SiR$_{18}R_{19}R_{20}$;
  $R_{10}$ and $R_{11}$ represent independently of each other H, (C1-C6)-alkyl, —$CF_3$, halogen or can form together a —CH$_2CH_2$—, —CH$_2CH_2CH_2$—, —CH$_2CH_2CH_2CH_2$—, or —CH$_2CH_2CH_2CH_2CH_2$— group;
  $R_{12}$ represents (C1-C6)-alkyl, benzyl or phenyl, wherein the alkyl group can be optionally substituted with fluorine or chlorine and the benzyl and phenyl are optionally substituted with one or more substituent(s) from the group: (C1-C6)-alkyl, (C1-C6)-alkoxy, —$CF_3$, cyano, nitro or halogen;
  $R_{13}$ represents H or $R_{12}$;

$R_{14}$ and $R_{15}$ represent independently of each other H, (C1-C6)-alkyl, benzyl or phenyl, wherein the benzyl and phenyl can be optionally substituted with one or more substituent(s) from the group: (C1-C6)-alkyl, (C1-C6)-alkoxy, —$CF_3$, cyano, nitro or halogen;

$R_{16}$ represents H or (C1-C6)-alkyl;

$R_{17}$ represents (C1-C6)-alkyl, benzyl or phenyl; and $R_{18}$, $R_{19}$ and $R_{20}$ represent independently of each other (C1-C6)-alkyl, benzyl or phenyl.

The invention includes also all pharmaceutically acceptable salts, as well as tautomeric, enantiomeric and other stereoisomeric forms of the compound of formula I.

According to this invention, if names of amino acids are used without the nomenclature prefixes D- or L-according to Fischer, both possibilities are possible; but preferred is the isomer naturally present in the environment (mostly L-isomer). If a corresponding nomenclature prefix is used, then the corresponding isomer is preferred according to the invention.

The $P_s$ and $P_b$ groups are either ionic groups, i.e. anionic groups $P_s$ or cationic groups $P_b$, or groups that in solutions easily dissociate to ionic groups $P_s$ or $P_b$. Preferably, these groups exist partially or completely in ionic form in the pH range from 6 to 8. The $P_s$ groups can also be polar groups having a hydrogen atom that could be cleaved off with stronger bases, wherein the hydrogen atom is preferably bound to a heteroatom.

Examples of acid $P_s$ groups are the followings:

a) —COOH, —$SO_3H$, —$CONH_2$, —$CONHNH_2$, —$SO_2NH_2$, —$PO_3H_2$, —PO(OH)($NH_2$), —CO(NHOH), —CO(NH—C1-C4-alkyl)), —$CSNH_2$, —$NHCONH_2$, —N(OH)$CONH_2$, —NHCO(NHOH), —$NHCSNH_2$, —$CSNHNH_2$;

b)

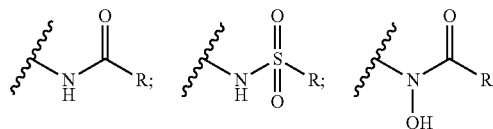

and R=—(C1-C4)-alkyl, —O(C1-C4)-alkyl, —NH(C1-C4)-alkyl, —NH(C1-C4-alkenyl), (substituted) aryl, (substituted) O-aryl, (substituted) NH-aryl, —$CF_3$ and other fluorinated (C1-C4-alkyl) groups;

c)

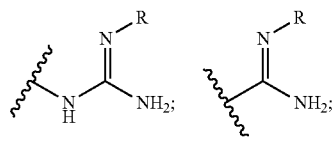

and R=—OH, —CN, —$NO_2$;

d)

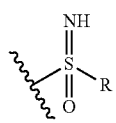

and R=(C1-C4-alkyl), (substituted) aryl, —$CF_3$ and other fluorinated (C1-C4-alkyl) groups;

e)

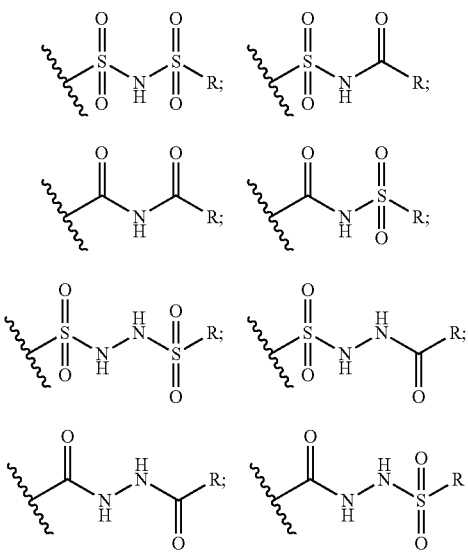

and R=—(C1-C4-alkyl), —O(C1-C4-alkyl), —NH(C1-C4-alkyl), —NH(C1-C4-alkenyl), (substituted) aryl, (substituted) O-aryl, (substituted) NH-aryl, —$CF_3$ and other fluorinated (C1-C4-alkyl) groups;

f)

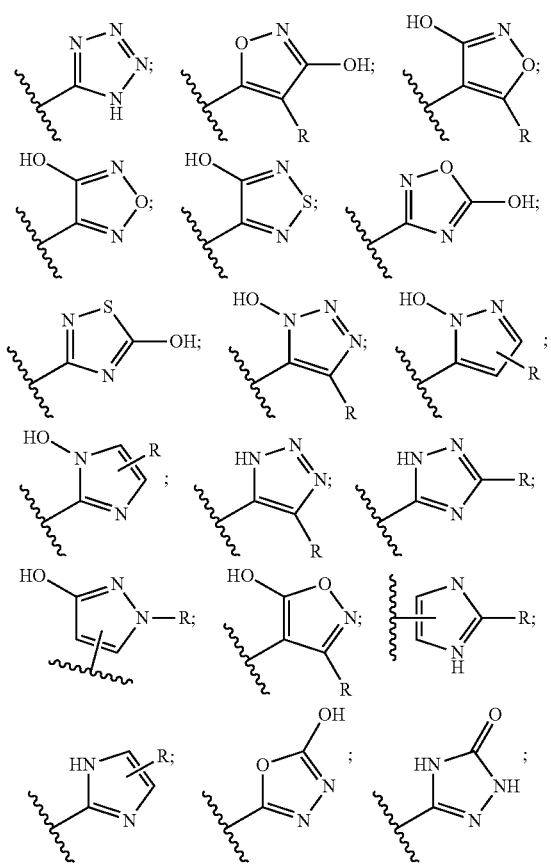

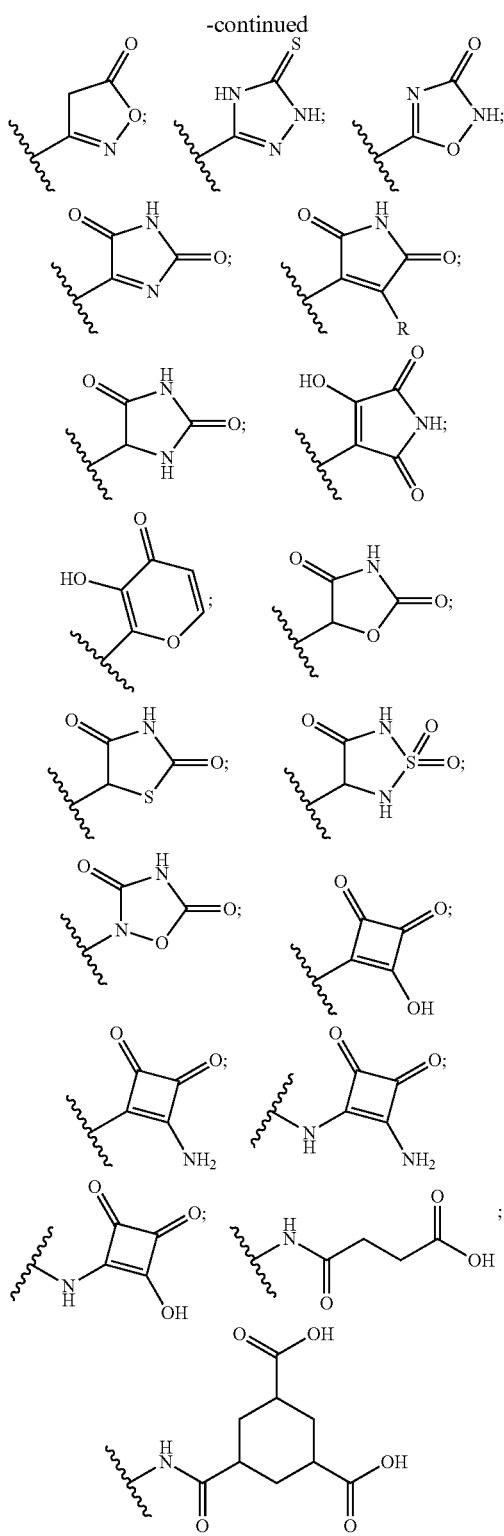

in which R=H, —(C1-C4-alkyl), —CF₃, and other fluorinated (C1-C4-alkyl) groups.

g) —OH and —SH, providing that L is a covalent single bond and that —OH or —SH can only be present as a substituent on a ring $Q_1$, $Q_2$ or $Q_3$ and thereby is bound to a carbon atom, which is positioned in the vicinity of a nitrogen atom.

According to the invention, it is especially preferred that the $P_s$ group is one of the following groups, which preferably is directly bound via a covalent bond to a heterocycle of formula IV-XII:

—COOH, —OH, —SH, —CONH₂, —CONHNH₂, —SO₃H, —SO₂NH₂, and the group

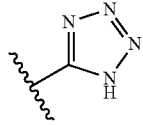

providing that, if $P_s$ represents —OH or —SH, then L is a covalent single bond, and —OH or —SH is bound to a carbon atom of a ring $Q_1$, $Q_2$ or $Q_3$, and said carbon atom is positioned in the vicinity of a nitrogen atom.

Examples of basic $P_b$ groups are the following:

a)

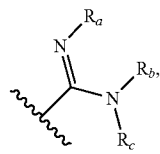

wherein $R_a$, $R_b$ and $R_c$ represent H and —(C1-C4-alkyl), $R_a$ and $R_b$ can be together —(CH₂CH₂)—, or —(CH₂CH₂CH₂)—, and $R_b$ and $R_c$ together with the nitrogen atom can be pyrrolidine, piperidine or morpholine;

b)

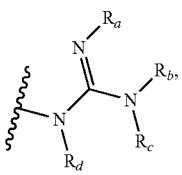

wherein $R_a$, $R_b$, $R_c$ and $R_d$ represent H and —(C1-C4-alkyl), $R_a$ and $R_b$, $R_a$ and $R_d$, as well as $R_b$ and $R_d$ together can be —(CH₂CH₂)—, or —(CH₂CH₂CH₂)— and $R_b$ and $R_c$ together with the nitrogen atom can be pyrrolidine, piperidine or morpholine;

c) an amino group selected from —NH₂, (C1-C6)alkyl-amino, (C1-C6)dialkyl-amino, pyrrolidine, pyperidine, morpholine or piperazine, which can be substituted at position 4 with (C1-C6)alkyl, —(C1-C6)alkanoyl, benzyl, benzoyl, or phenyl, wherein these substituents can optionally have a —COOH group.

According to the present invention, it is especially preferred that the $P_b$ group is one of the following groups, which is directly bound via a covalent bond to a heterocycle of formula IV-XII:

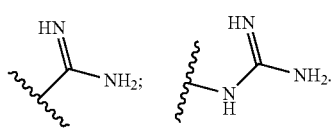

The $P_s$ and $P_b$ groups can also be a

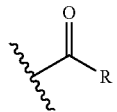

group, wherein R is an amino acid or an amino acid amide, which are bound via their amino groups, or a peptide consisting of 2-10 amino acids and in which the terminal amino acid can also be an amino acid amide. Preferred peptide groups contain at least one amino acid from the group: D-glutamic acid, L-glutamic acid, D-aspartic acid, L-aspartic acid, D-glutamine, L-glutamine, D-asparagine, L-asparagine, D-cysteine sulfonic acid, L-cysteine sulfonic acid, D-arginine or L-arginine. Preferred are peptide groups of formula

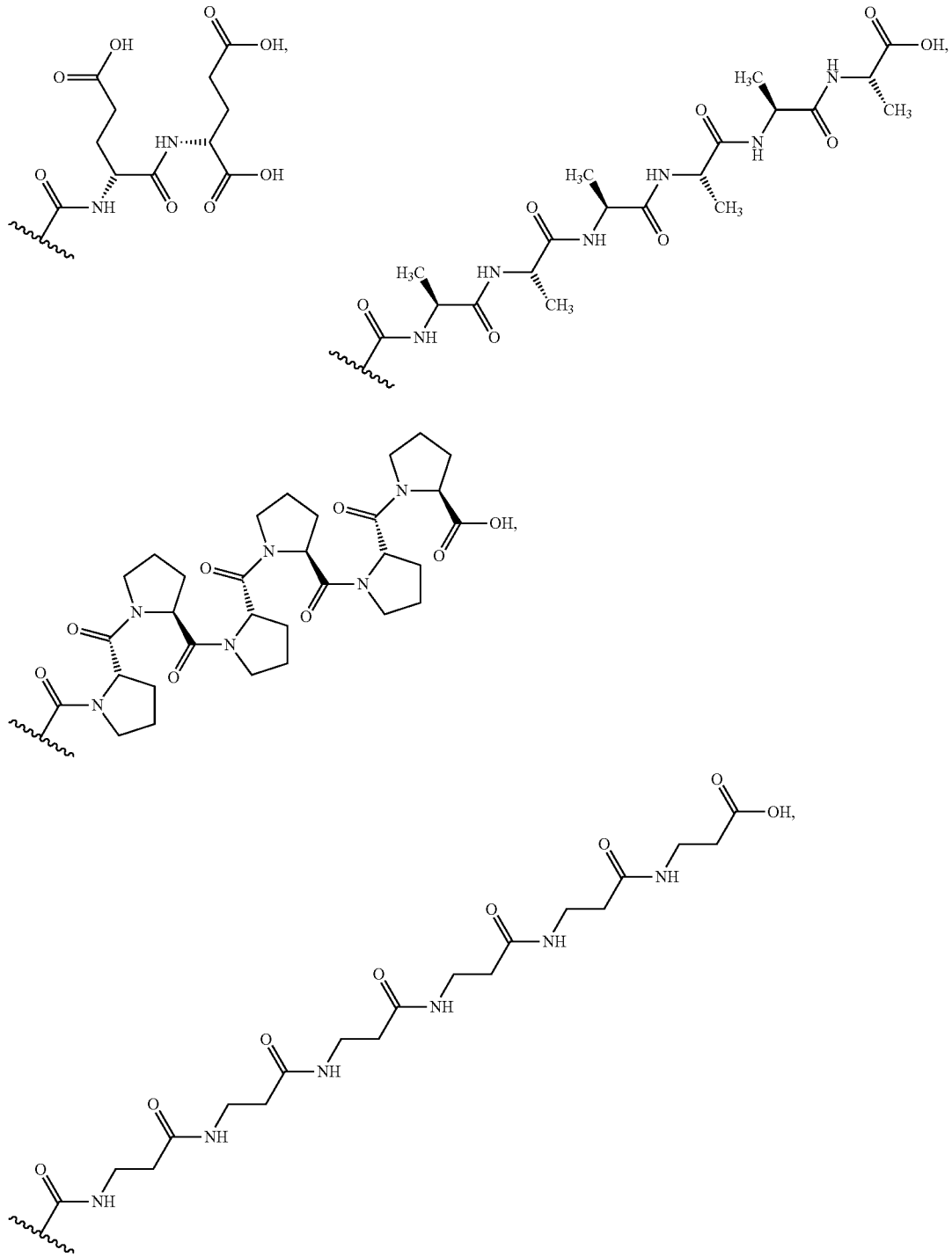

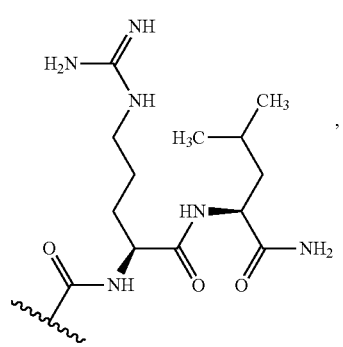
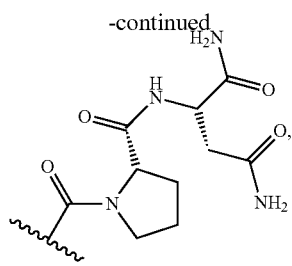
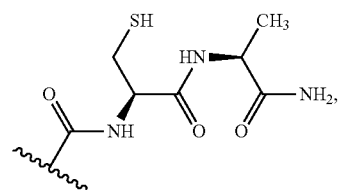

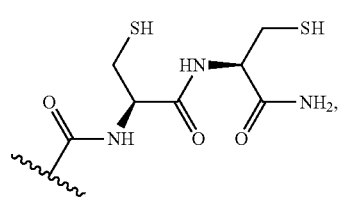
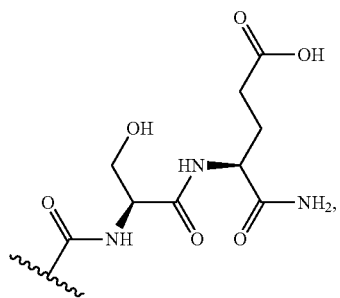
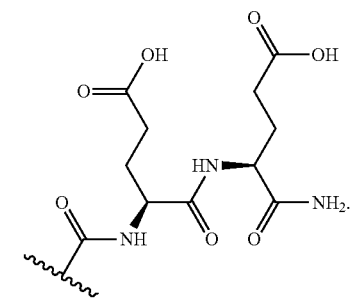

and

In the present application, the term "amino acid" encompasses any organic compound containing an amino group and a carboxylic acid group or a sulfonic acid group. In the present application, the naturally occurring amino acids are preferred.

The groups $P_s'$ and $P_b'$ are groups that can be converted under physiological conditions to the groups $P_s$ and $P_b$, respectively. Compounds containing groups $P_s'$ and $P_b'$ are termed "prodrugs". Such compounds do not necessarily have to be cell-impermeable, but they are ideally transforming themselves to cell-impermeable derivatives after application, preferably after oral application, so that they cannot penetrate into the cell at the site of action.

For example, carboxylic acid esters can be used as prodrugs for carboxylic acids ($P_s$=—COOH) (K. Beaumont, et al., Current Drug Metabolism 4 (2003), 461-485). Examples of carboxylic acid esters $P_s'$=—COOR contain the residue R a) (C1-C6-alkyl), (C2-C6-alkenyl), phenyl or benzyl, wherein the aromatic ring can have further substituents, preferably —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH=CH$_2$, benzyl;

b) (C1-C6-alkyl), in which the hydrogen atoms are replaced by a halogene, preferably —CF$_3$, —CH$_2$CCl$_3$;

c) (C1-C6-alkyl), in which the hydrogen atom is replaced by —OH, (C1-C6-alkoxy) or a substituted amino group, preferably —CH$_2$OCH$_3$, —CH$_2$CH$_2$OCH$_3$, —CH$_2$CH$_2$OH, —CH$_2$CH$_2$N(CH$_3$)$_2$, —CH$_2$CH$_2$(morpholin-4-yl);

d)

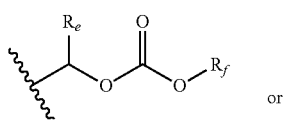

or

-continued

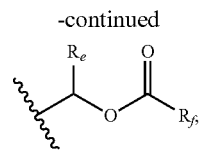

wherein $R_e$ represents H or (C1-C4-alkyl) and $R_f$ represents (C1-C4-alkyl) or (C3-C6-cycloalkyl), preferably $R_e$=H, —CH$_3$, —CH$_2$CH$_3$, —CH(CH$_3$)$_2$ and $R_f$=—CH$_3$, —CH$_2$CH$_3$, —CH(CH$_3$)$_2$, —C(CH$_3$)$_3$, cyclohexyl;

e)

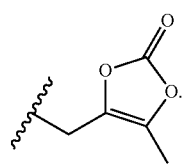 [SMILES: *Cc1oc(=O)oc1C]

It is especially preferred that the Ps' group is one of the following groups: —COOCH$_3$, —COOCH$_2$CH$_3$, —COOCH$_2$CH$_2$CH$_3$, —COOCH$_2$CH$_2$CH$_2$CH$_3$, —COOCH$_2$CH(CH$_3$CH$_3$)$_2$, —COOCH(CH$_3$)$_2$, —COOC(CH$_3$)$_3$, —COOCH$_2$CH$_2$N(CH$_3$)$_2$ or —COOCH$_2$CH$_2$(morpholin-4-yl).

Acetylated derivatives $P_b'$ can be used as prodrugs for basic $P_b$ groups such as amidine and guanidine, wherein $P_b'$=

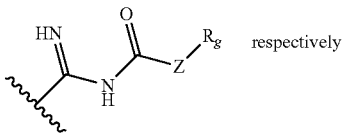 respectively

-continued

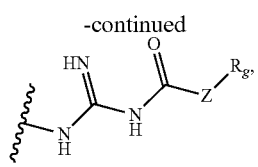

in which Z=O, S, NH or NCH₃ and R_g=(C1-C4-alkyl), (C3-C6-cycloalkyl) or benzyl, and preferably Z=O and R_g=—CH₃, —CH₂CH₃, —CH₂CH₂CH₃, —CH(CH₃)₂, benzyl.

It is especially preferred that R₂ is selected from the group of residues consisting of the following: —COOH, —OH, —SH, —CONH₂, —CONHNH₂, —SO₃H, —SO₂NH₂, —COOCH₃, —COOCH₂CH₃, —COOCH₂CH₂CH₃, —COOCH₂CH₂CH₂CH₃, —COOCH₂CH(CH₂CH₃)₂, —COOCH(CH₃)₂, —COOC(CH₃)₃, —COOCH₂CH₂N(CH₃)₂ or —COOCH₂CH₂(morpholin-4-yl), the groups

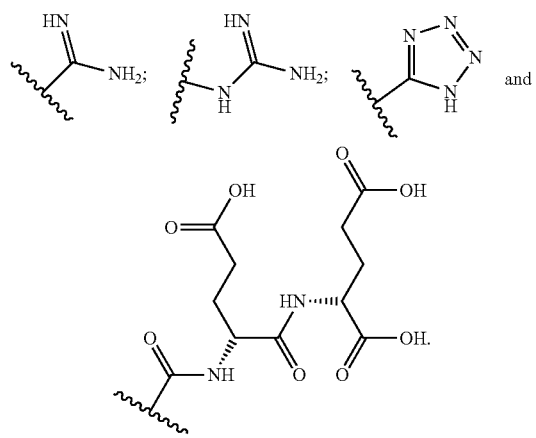

Further preferred is that R₀ represents —CH₃ in the inventive compounds of general formula I.

Preferably, the group R₇ is selected from the group consisting of: —OH, —OCOCH₃, —OCOOCH₃, —OCH₂OCH₃, —Si(CH₃)₃ and —Si(CH₃)₂C(CH₃)₃. It is especially preferred that R₇ represents —OH.

The bivalent group L is preferably selected from the group consisting of a bond, preferably of a covalent single bond, —CH₂—, —CH₂CH₂—, —CH=CH—, —CONH— and —OCH₂—. It is especially preferred that L represents a covalent single bond.

It is further preferred that R₂ represents —COOH, —SO₃H, —SO₂NH₂, tetrazol-5-yl, —C=NH(NH₂) or —NH—C=NH(NH₂) and the bivalent group L is a covalent bond.

It is especially preferred that the group R₁ represents H or CH₃, and even more preferred represents H.

Moreover, it is preferred that X represents N—R₁, even more preferred X represents NH.

The ring Q₁ is particularly preferred benzene, pyridine or pyrimidine, and strongestly preferred benzene.

The rings Q₂ and Q₃ are independently of each other preferably benzene. If one compound contains both rings Q₂ and Q₃, then it is mostly preferred that both rings Q₂ and Q₃ are benzene.

The bivalent moiety Y is especially preferred O, S, —CH₂—, or —CH₂CH₂—.

In addition it is preferred if R₃ is selected from the group which consists of H, —COOH, CH₃, OCH₃, F, Cl, Br and CN. Especially preferred R₃ represents H and F, and even more preferred H.

It is especially preferred that R₄ and R₅ are independently of each other H or F, and even more preferred H.

It is especially preferred that group A represents CH.

It is especially preferred that groups R₁₀ and R₁₁ are independently of each other H or CH₃, an even more preferred H.

Moreover, it is preferred that the group R₈ is a group of formula IV, V, VII, IX or XI. It is especially preferred that group R₈ is a group of formula IV.

If group R₈ is a group of formula IV, then in a preferred embodiment Q₁ represents benzene and X represents NH, L is a covalent single bond or —CH=CH—, R₂ is —COOH, —CONH₂, —CONHNH₂, —SO₃H, —SO₂NH₂, —COOCH₃, —COOCH₂CH₃, —COOCH₂CH₂CH₃, —COOCH₂CH₂CH₂CH₃, —COOCH₂CH(CH₂CH₃)₂, —COOCH(CH₃)₂, —COOC(CH₃)₃, —COOCH₂CH₂N(CH₃)₂ or —COOCH₂CH₂(morpholin-4-yl) or one of the groups

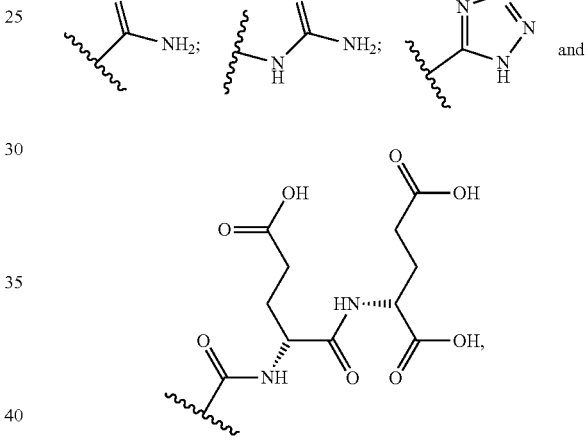

R₃ represents H, —COOH, —COOMe or F and preferably H; R₄ represents H or F, and preferably H, and R₅ represents H.

If group R₈ is a group of formula IV, then in a further preferred embodiment Q₁ represents pyridine or pyrimidine and X represents NH. Thereby, it is especially preferred that Q₁ is pyrimidine, L is a covalent single bond, R₂ represents SH, OH or NH₂, and preferably SH or OH, R₃ represents H, SH, OH or NH₂, and preferably H, SH or OH, and R₄ and R₅ are preferably not present (since the heteroatoms of the pyrimidine ring are situated at this position).

If group R₈ is a group of formula IX, X or XI, then in a further preferred embodiment X represents NH, A represents CH, Q₂ represents benzene, L represents a covalent single bond, R₂ represents —SO₃H or —COOH and R₃ represents H.

If group R₈ is a group of formula XIII, then in a further preferred embodiment R₁, R₁₀ and R₁₁ represent H.

It is furthermore preferred that the scaffold of formula I is a substituted cyclosporin A compound corresponding to the following formula:

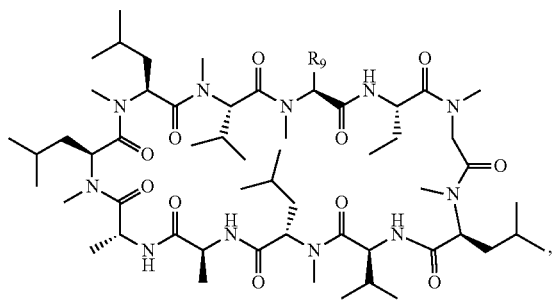

wherein $R_9$ has the same meanings as above or below defined.

Moreover, it is especially preferred that the compound of formula I is a substituted cyclosporin A-derivative of following formula:

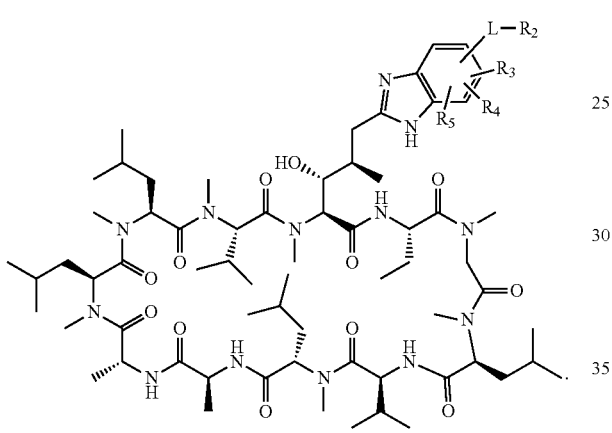

All the features of the compound of aforementioned formula I listed in the different embodiments can be, according to the present invention, combined with each other provided that they are not mutually exclusive. If in the mentioned embodiments, residues of the compound of aforementioned formula I are not explicitly defined in the mentioned embodiment, then they can have according to the present invention every specified general or particular definition.

As an example for compounds of aforementioned formula I the following compounds are listed:
Ac-CsA-aldehyde, TBDMS-CsA-aldehyde and Ac-CsA-acid,
which can serve as starting material for the synthesis of compounds of formula I derived from cyclosporin A:
Compounds 1, 2 and 3: Ac-CsA-aldehyde, TBDMS-CsA-aldehyde and Ac-CsA-acid (CsA meaning cyclosporin A) (hereinafter):

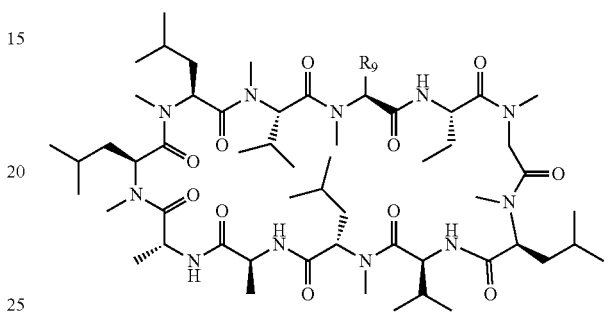

wherein $R_9$ corresponds to the following structure:

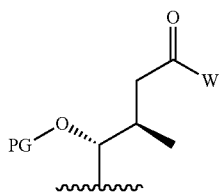

and wherein in case of compound 1, PG represents an acetyl group (Ac) and W=H, in case of compound 2, PG represents a tert-butyldimethylsilyl group (TBDMS) and W=H, and in case of compound 3, PG represents an acetyl group (Ac) and W=OH.

In the present invention, the following compounds 4 to 68 are especially preferred as compounds of formula I:

Compound 4

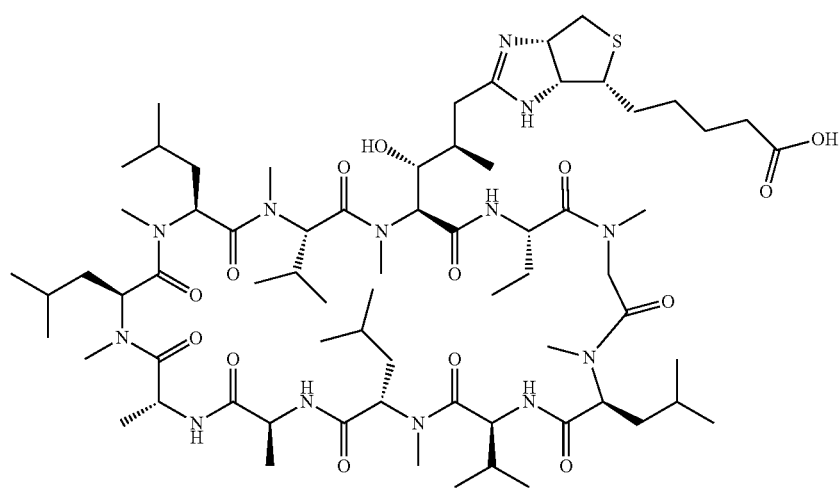

-continued
Compound 5
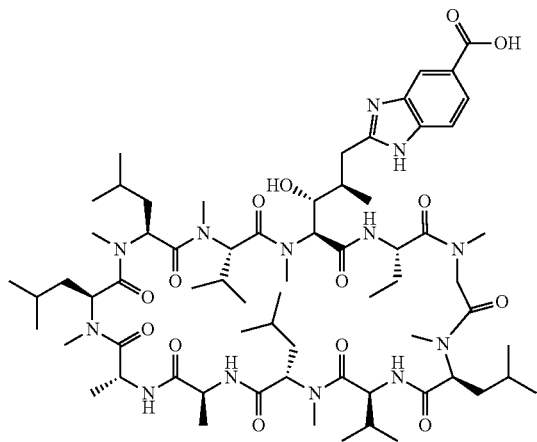
Compound 6
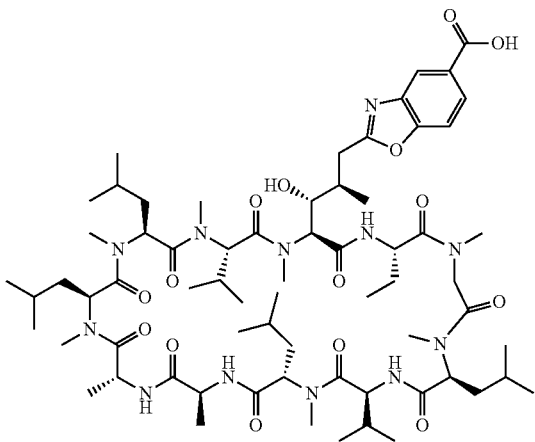
Compound 7
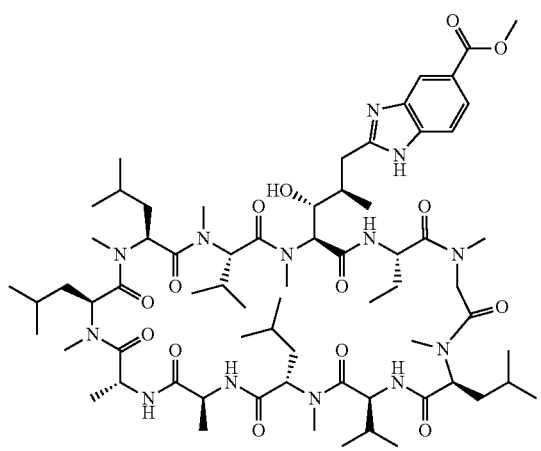
Compound 8
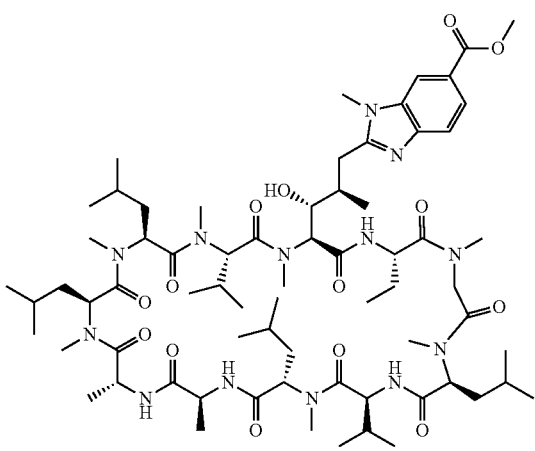
Compound 9
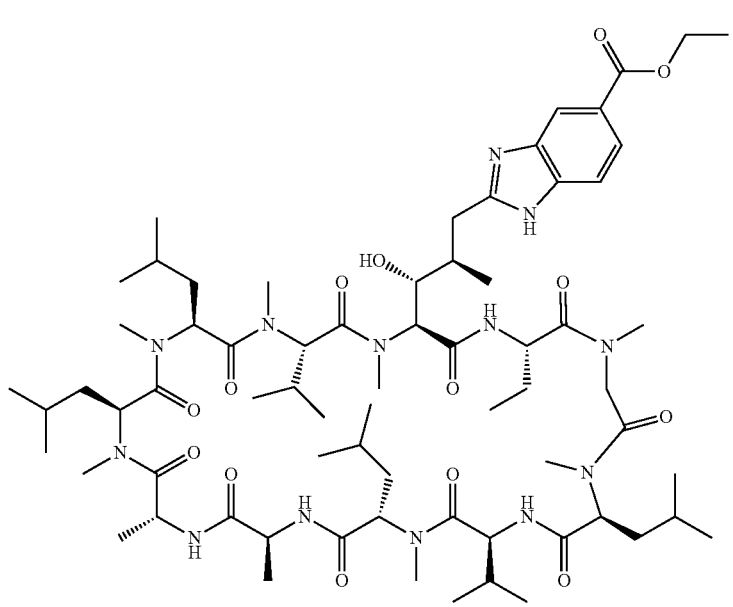

-continued
Compound 10
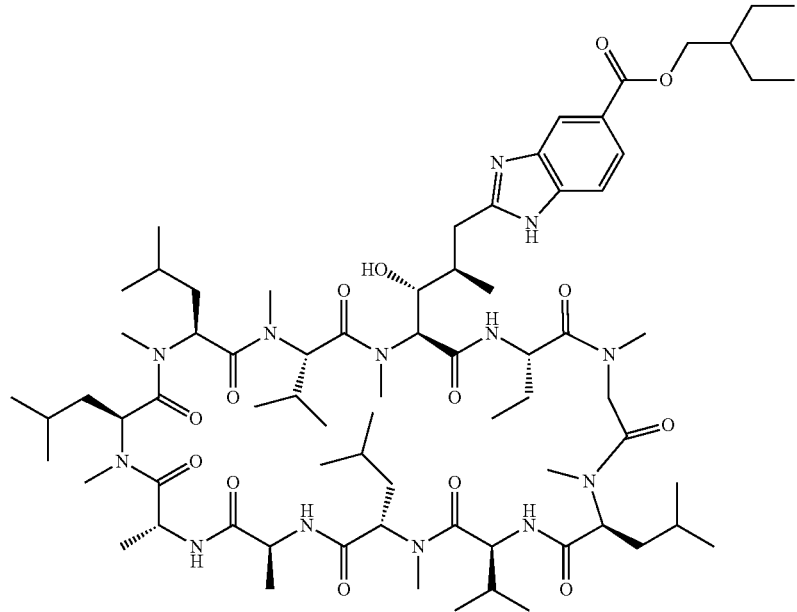
Compound 11
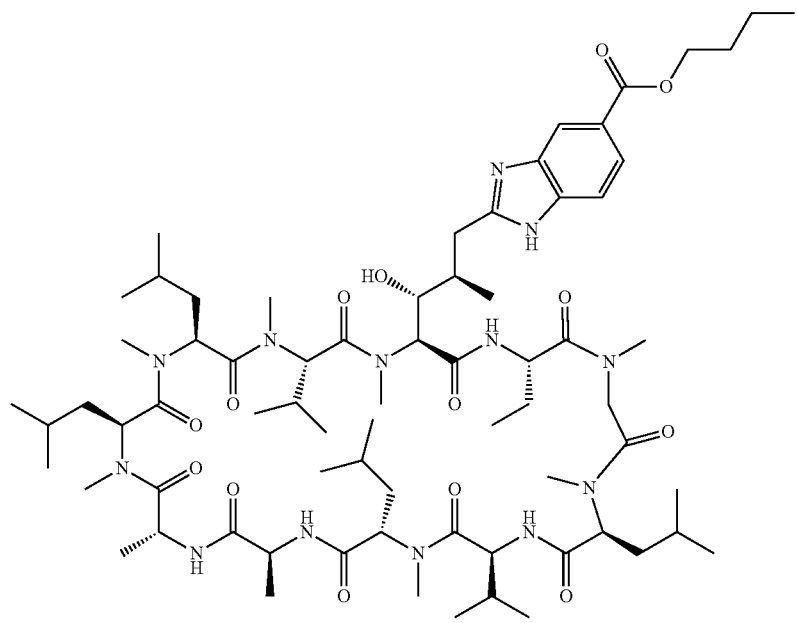

-continued
Compound 12
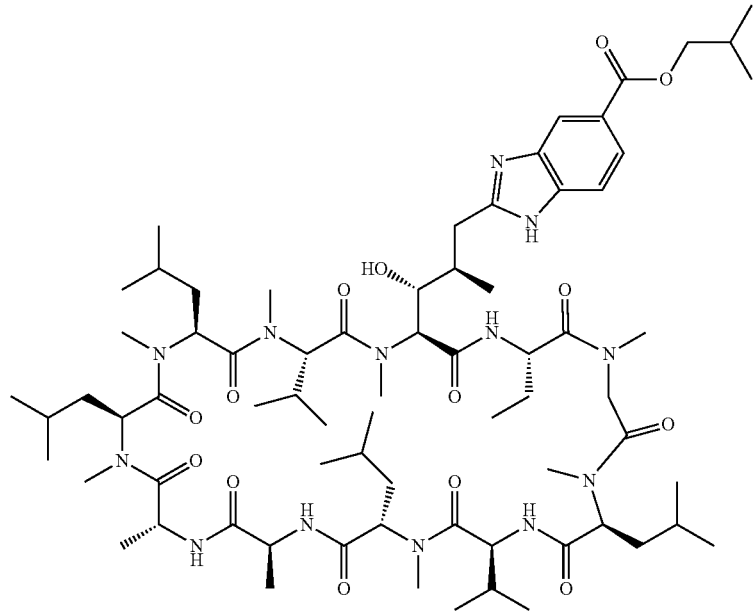
Compound 13
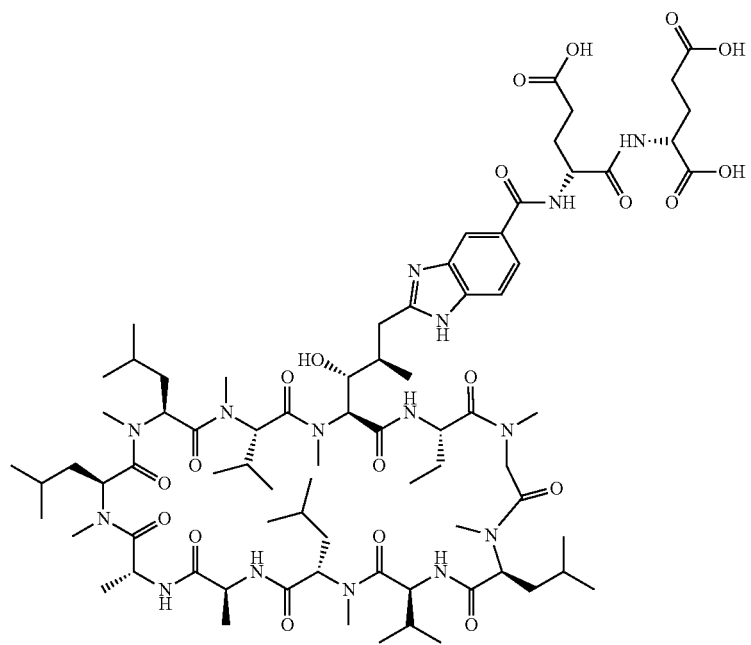

Compound 14
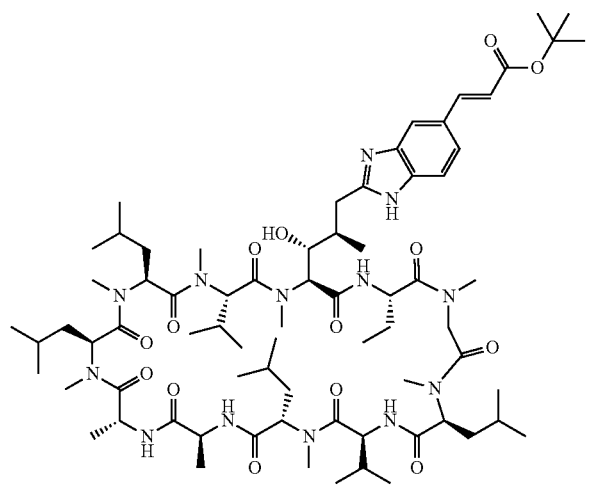
Compound 15
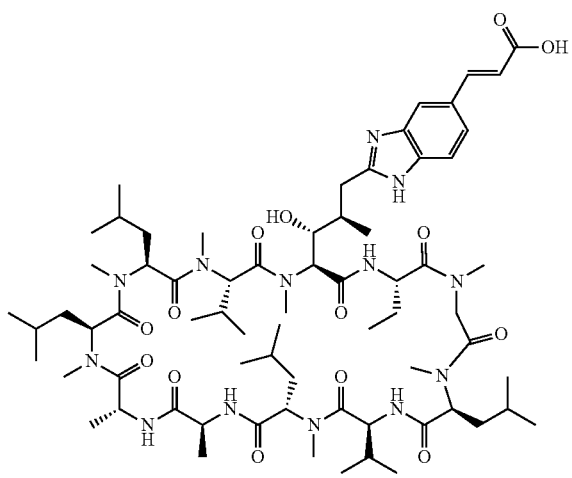
Compound 16
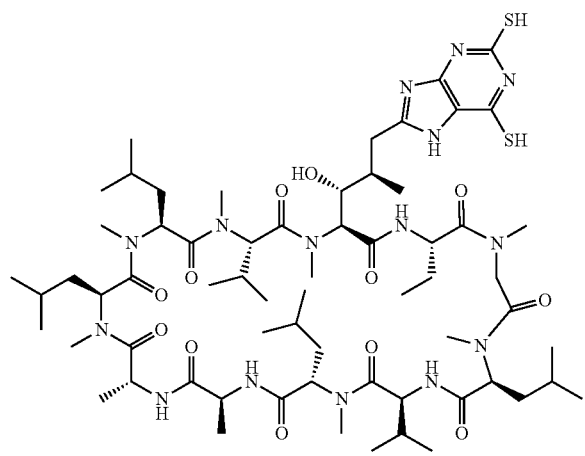
Compound 17
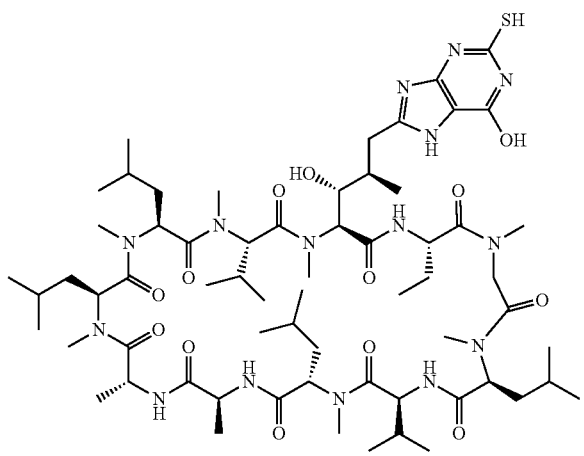
Compound 18
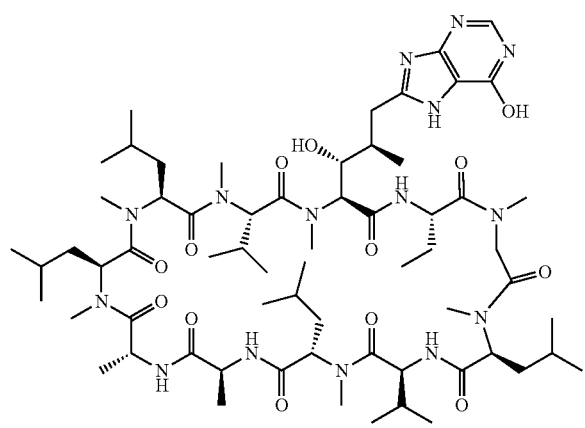
Compound 19
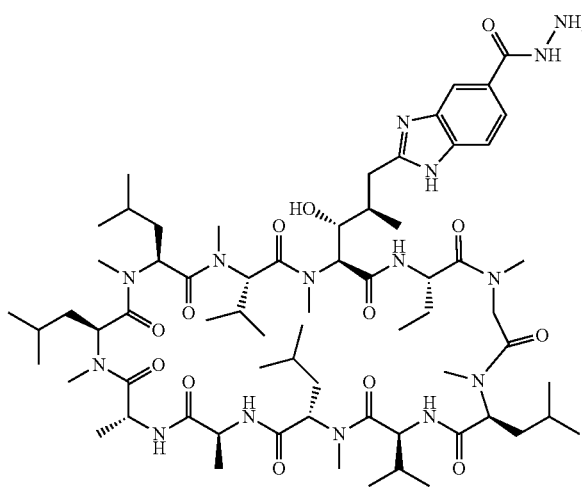

-continued
Compound 20
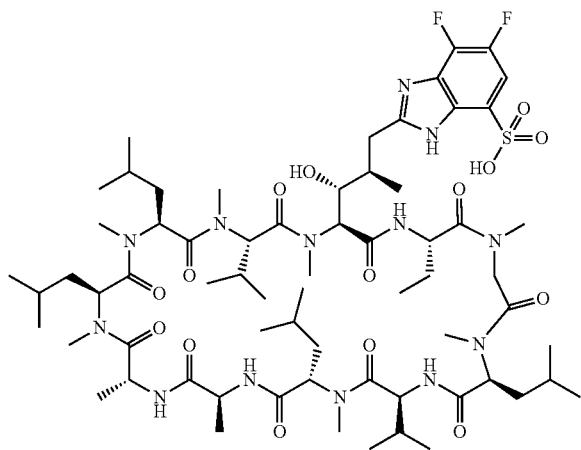
Compound 21
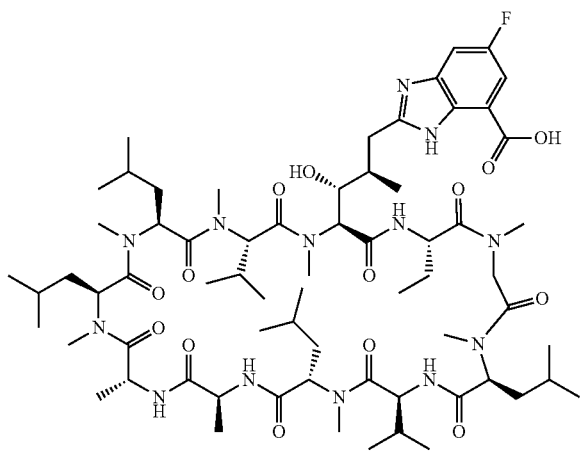
Compound 22
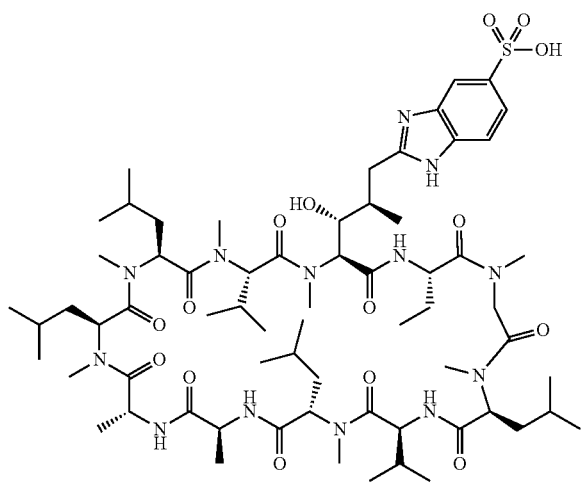
Compound 23
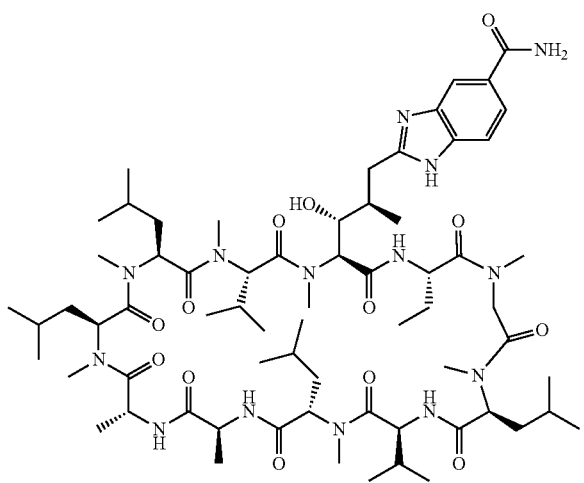
Compound 24
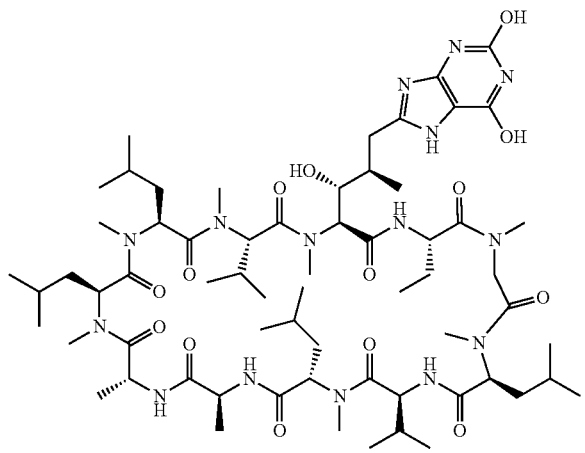
Compound 25
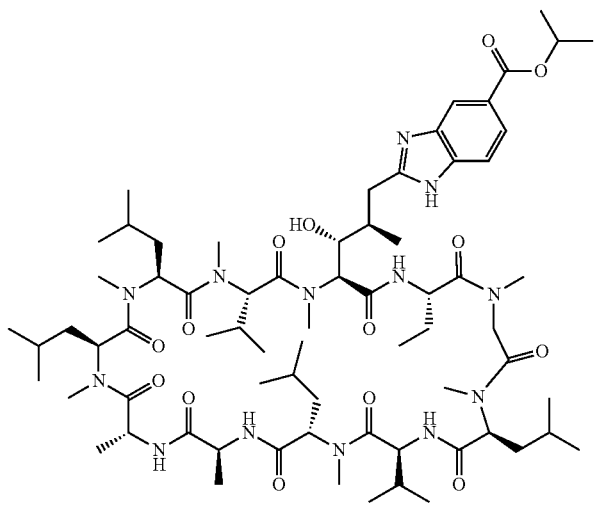

Compound 26
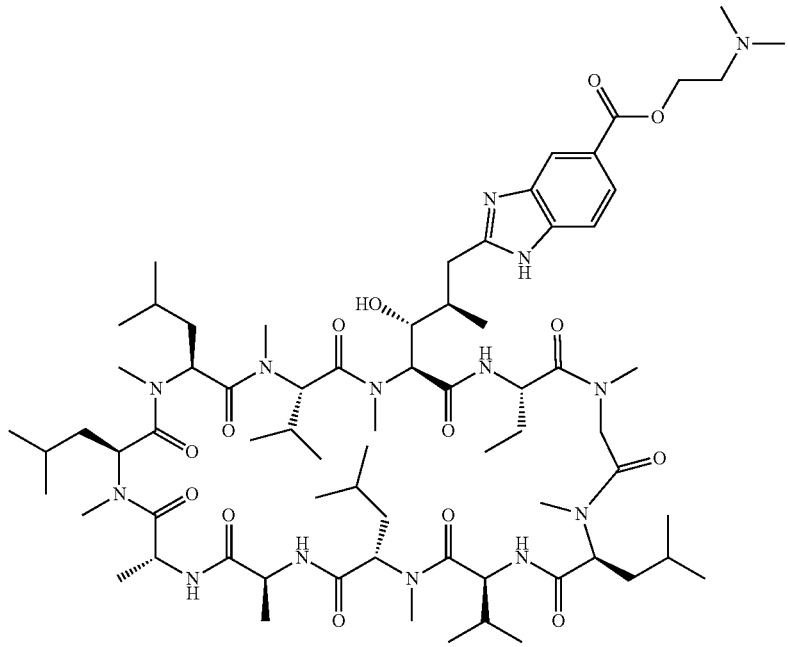
Compound 27
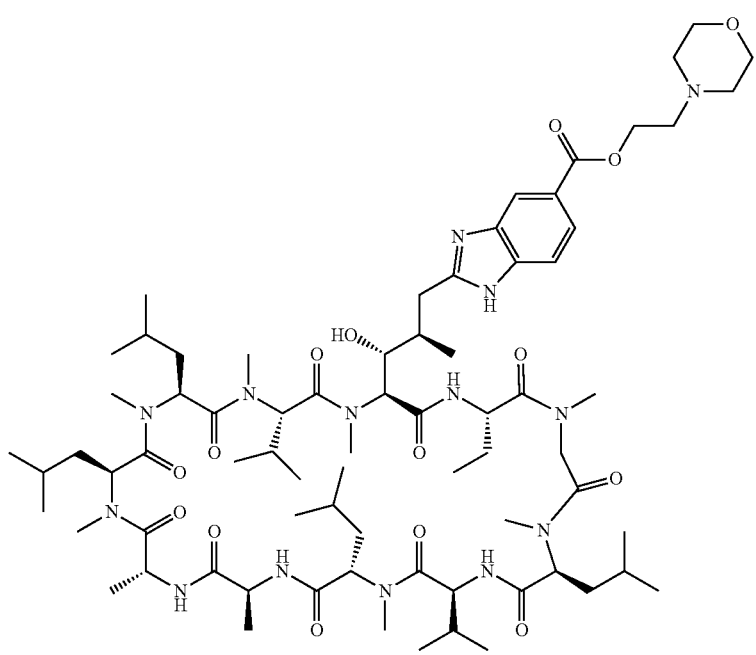

-continued
Compound 28
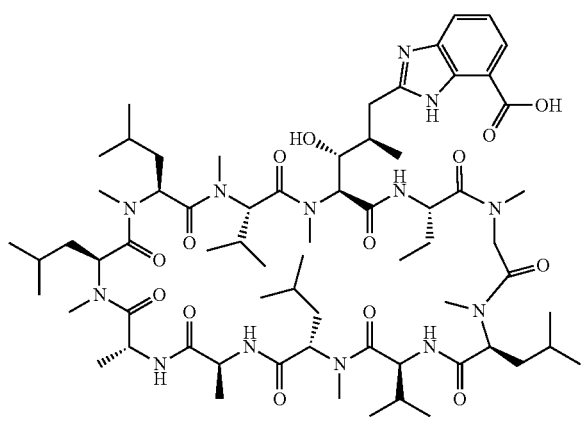
Compound 29
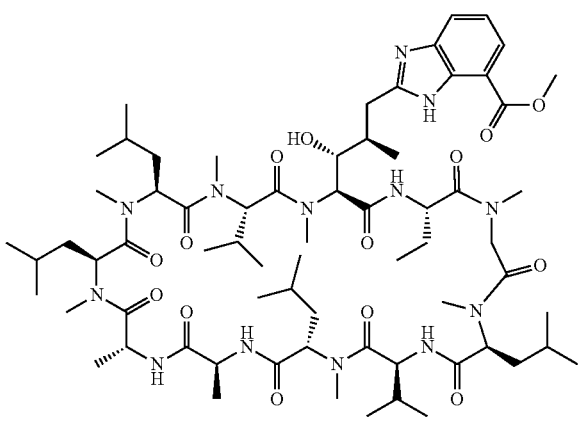
Compound 30
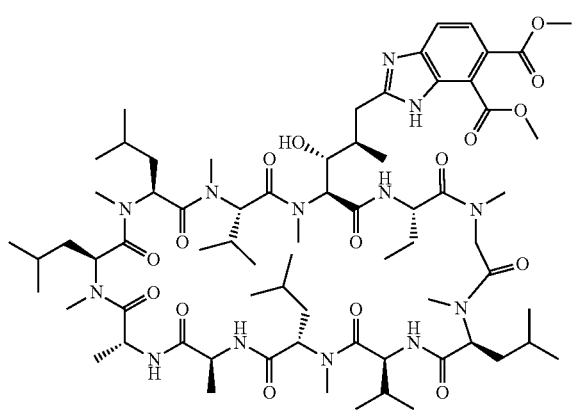
Compound 31
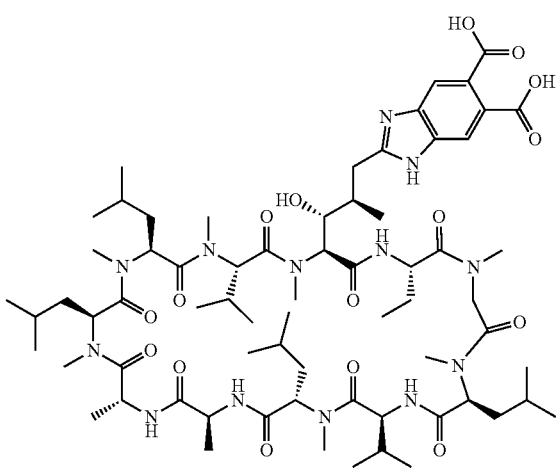
Compound 32
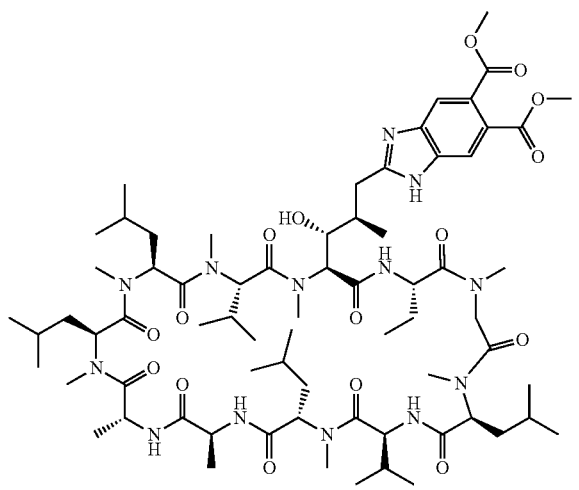
Compound 33
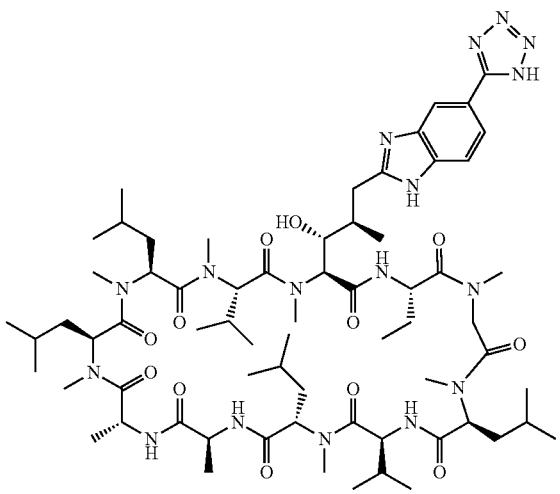

-continued
Compound 34
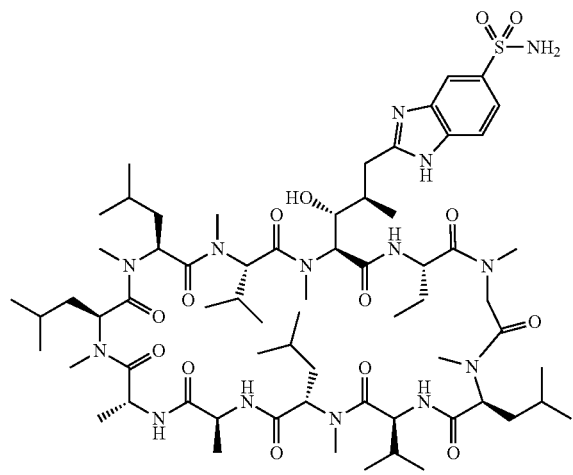
Compound 35
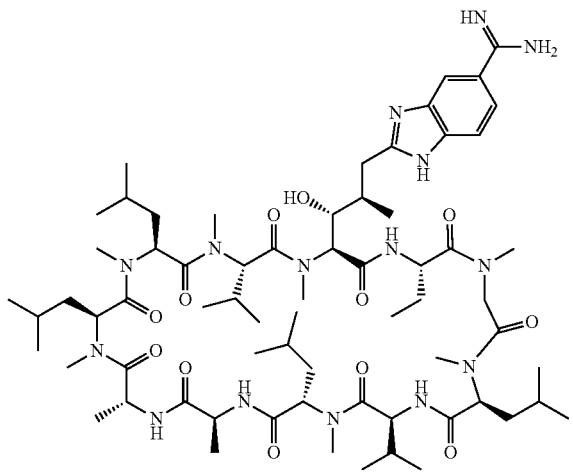
Compound 36
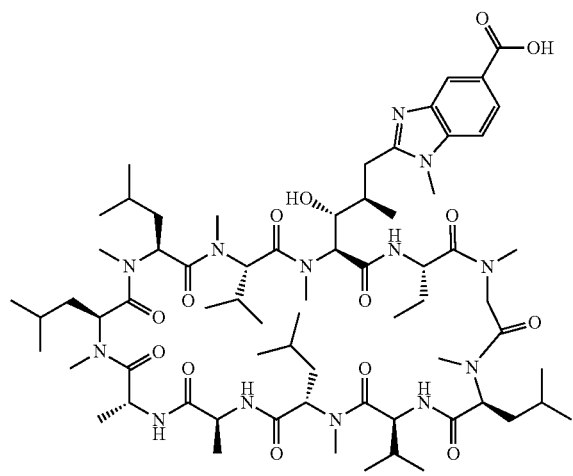
Compound 37
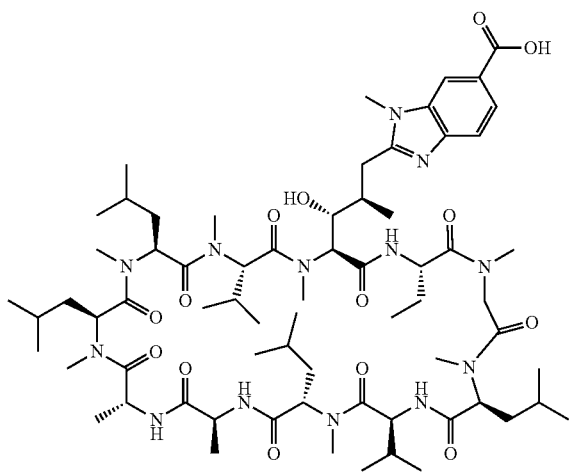
Compound 38
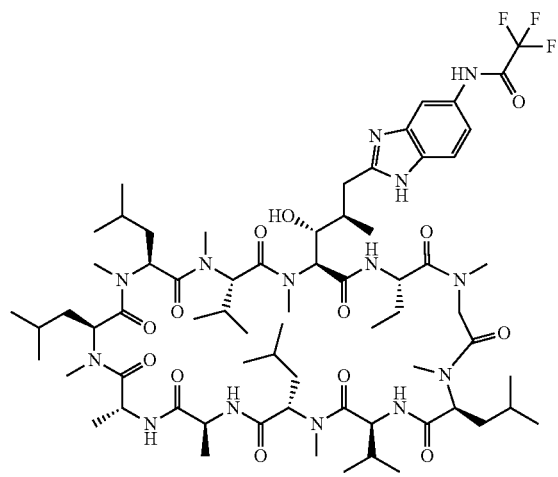
Compound 39
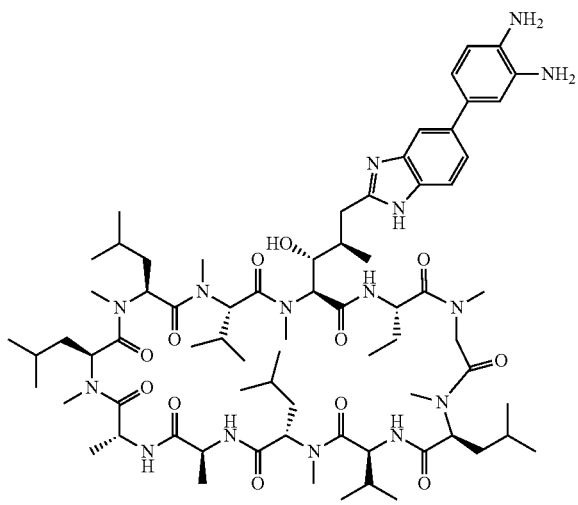

-continued
Compound 40
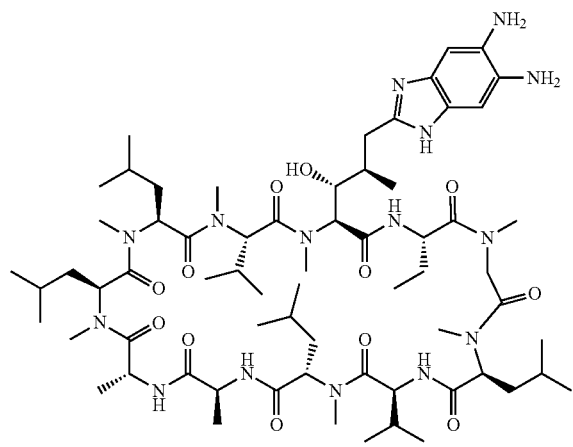
Compound 41
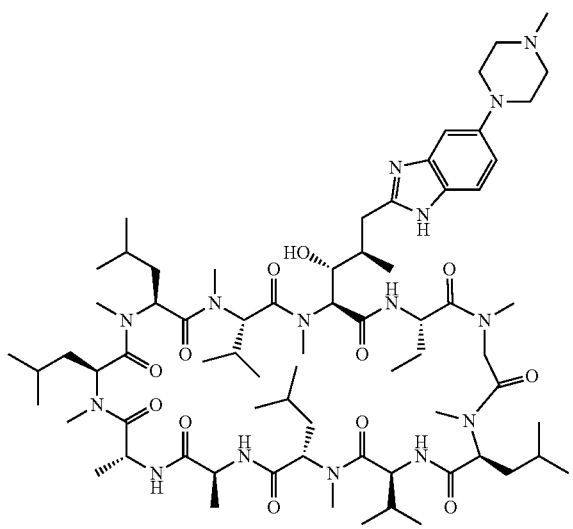
Compound 42
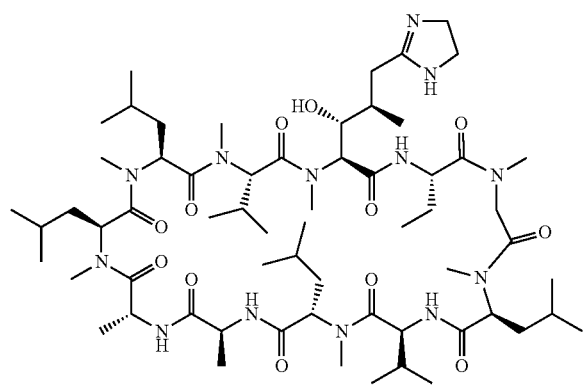
Compound 43
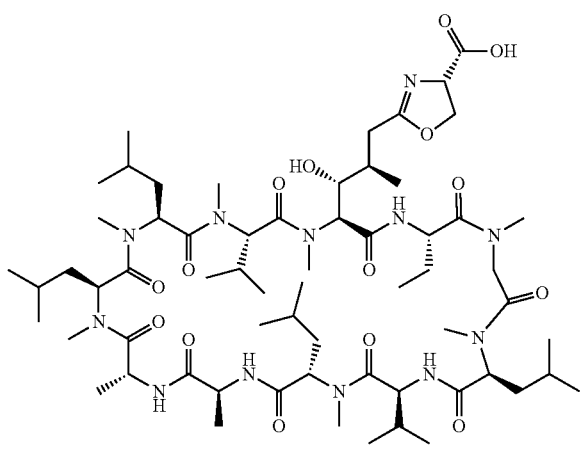
Compound 44
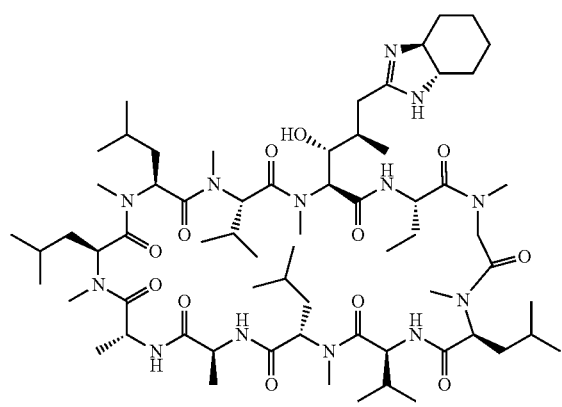
Compound 45
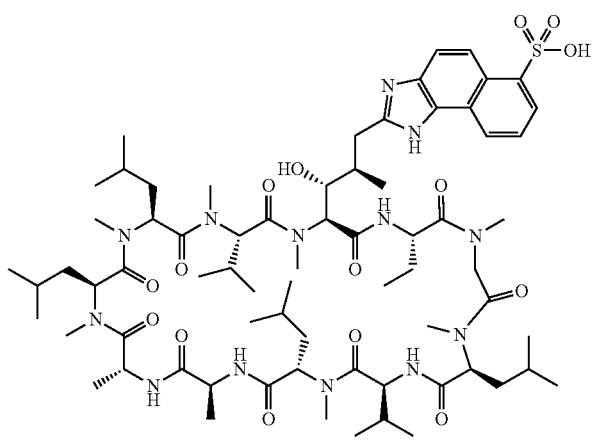

-continued
Compound 46
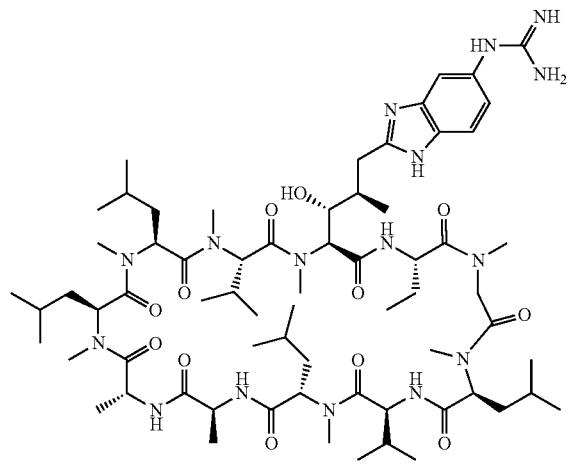
Compound 47
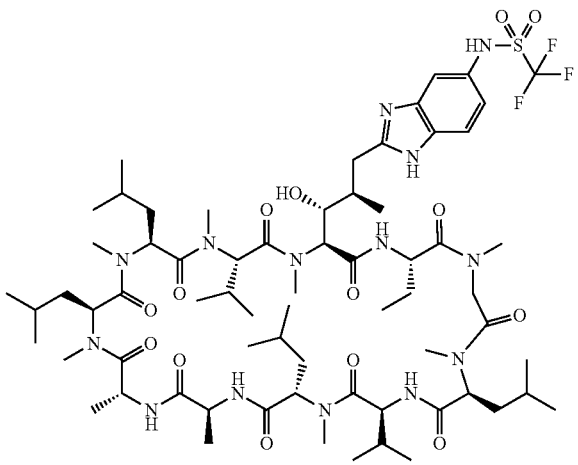
Compound 48
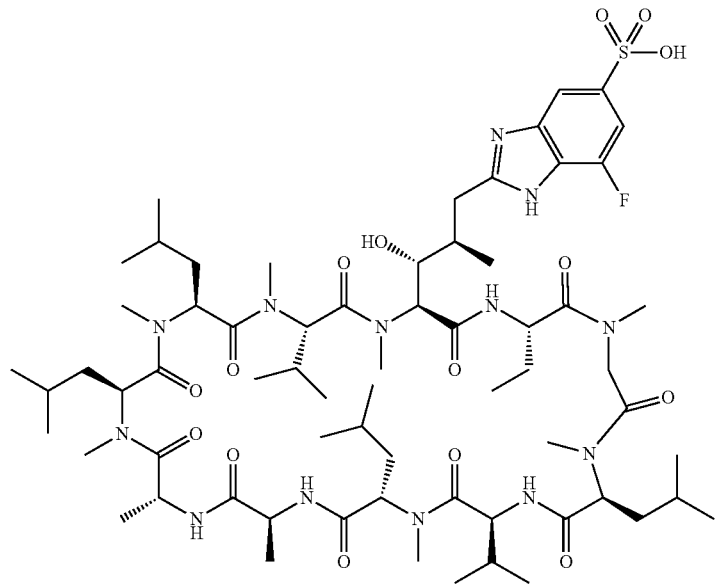

-continued
Compound 49
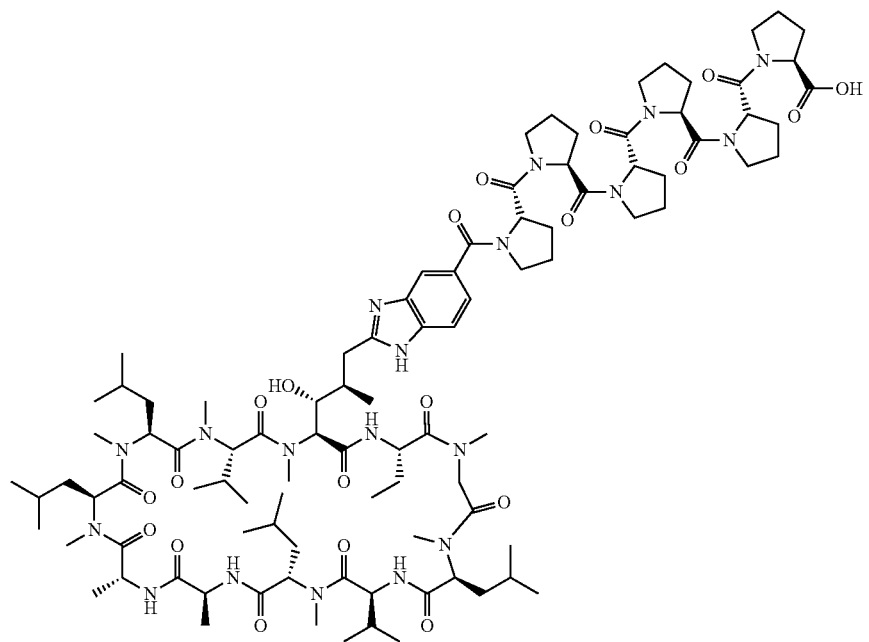
Compound 50
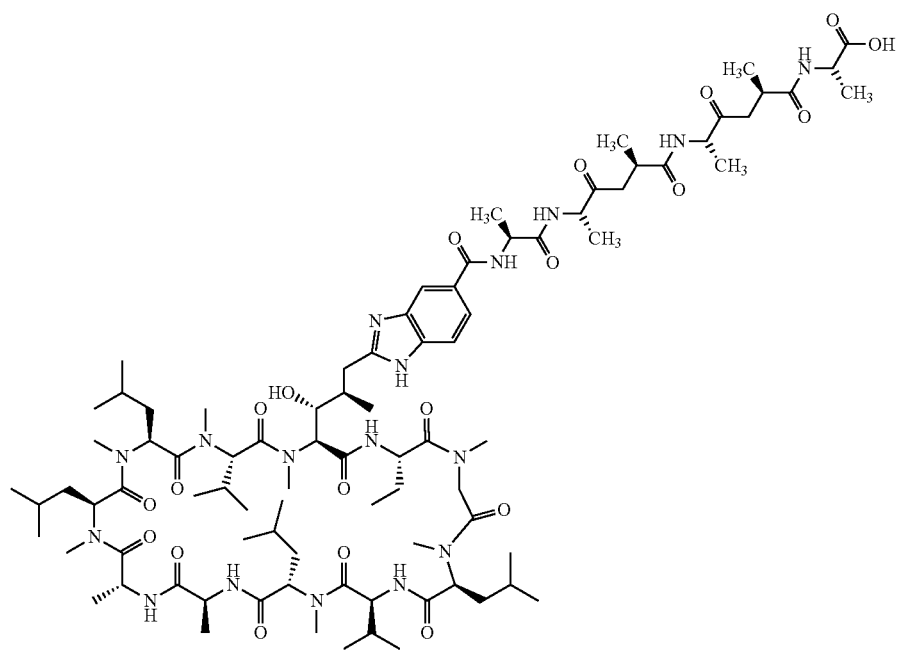

-continued
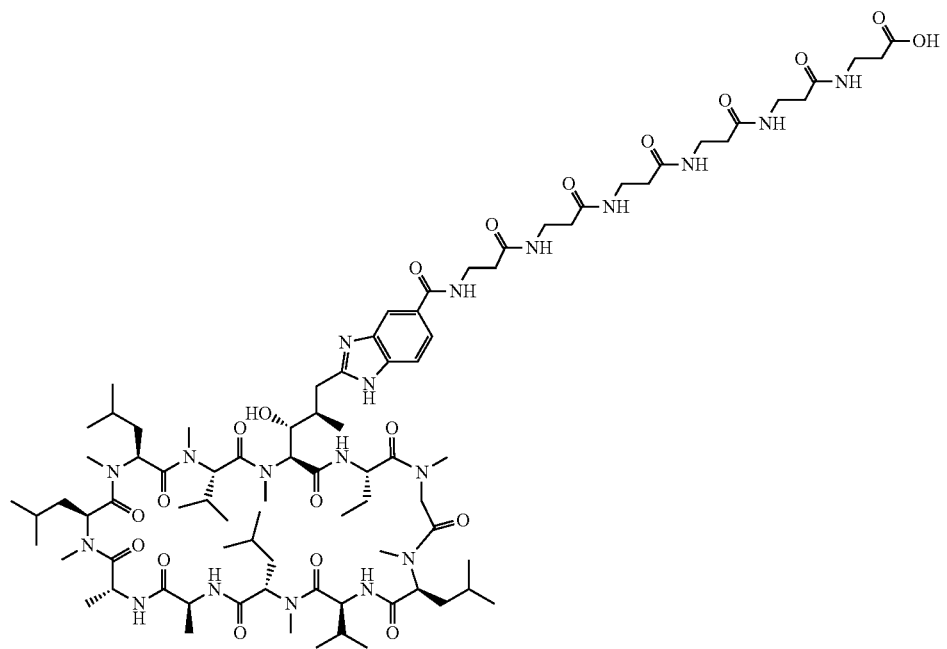
Compound 51
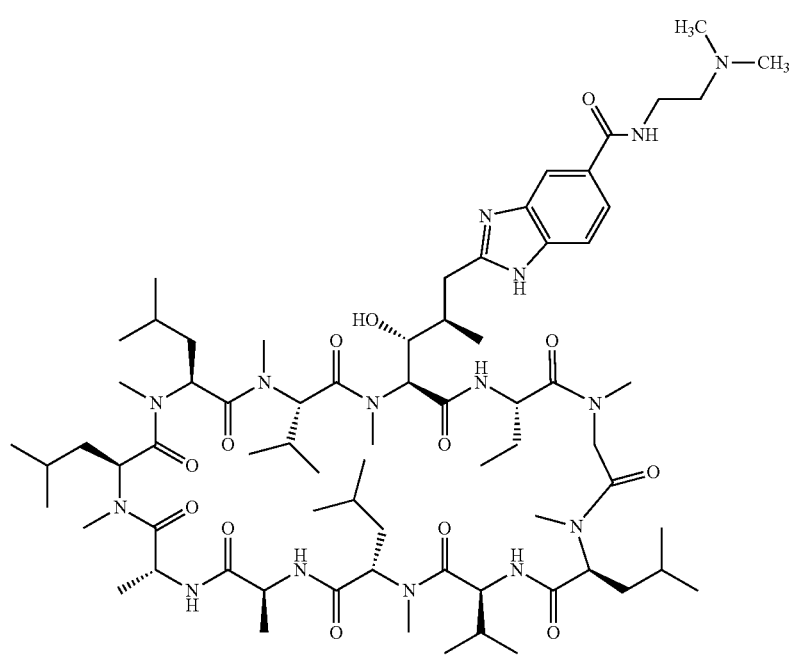
Compound 52

-continued
Compound 53
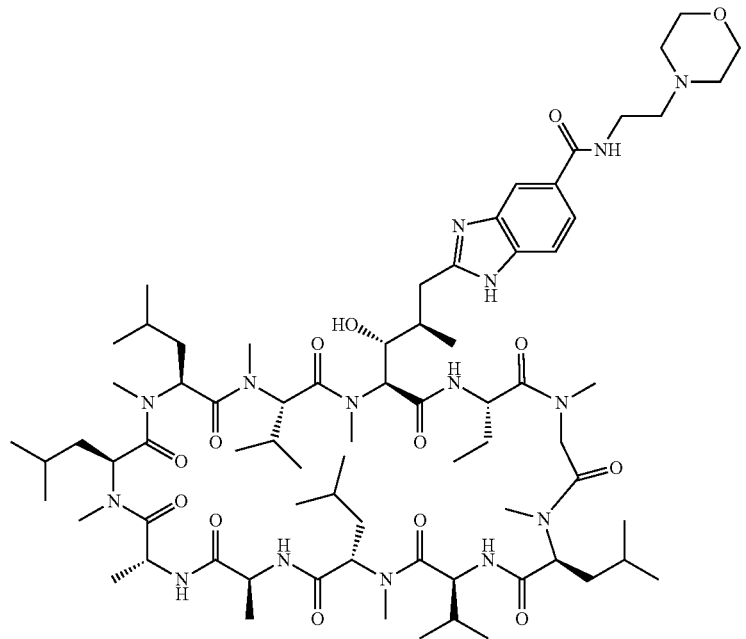
Compound 54
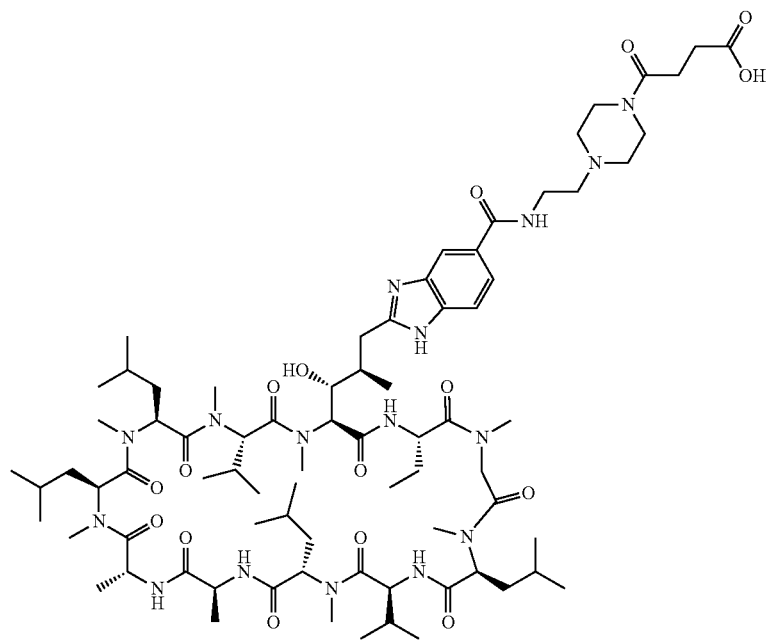

-continued
Compound 55
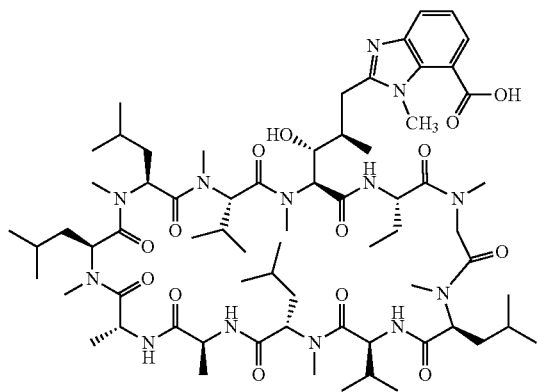
Compound 56
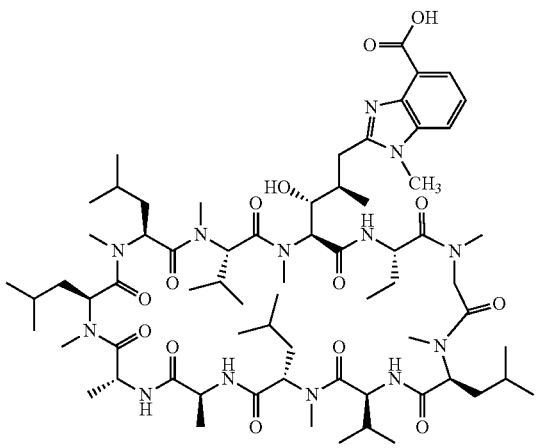
Compound 57
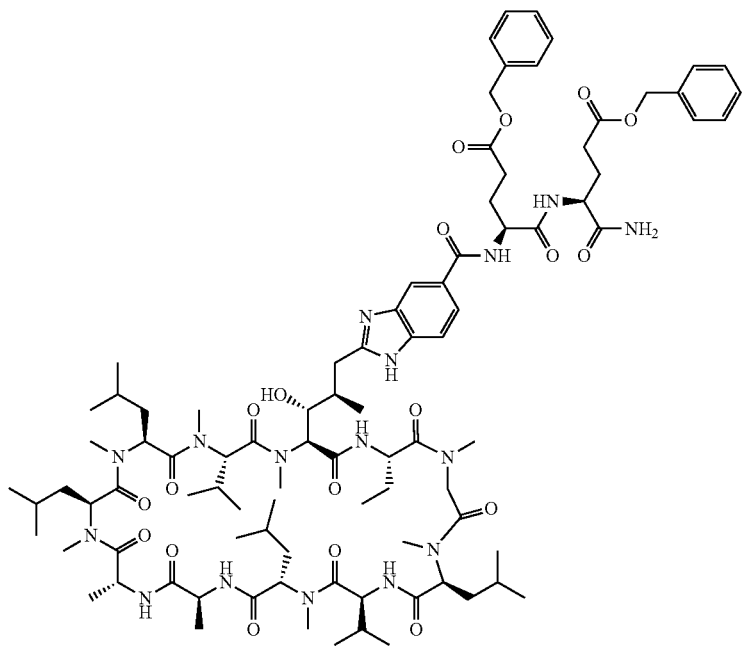

-continued
Compound 58
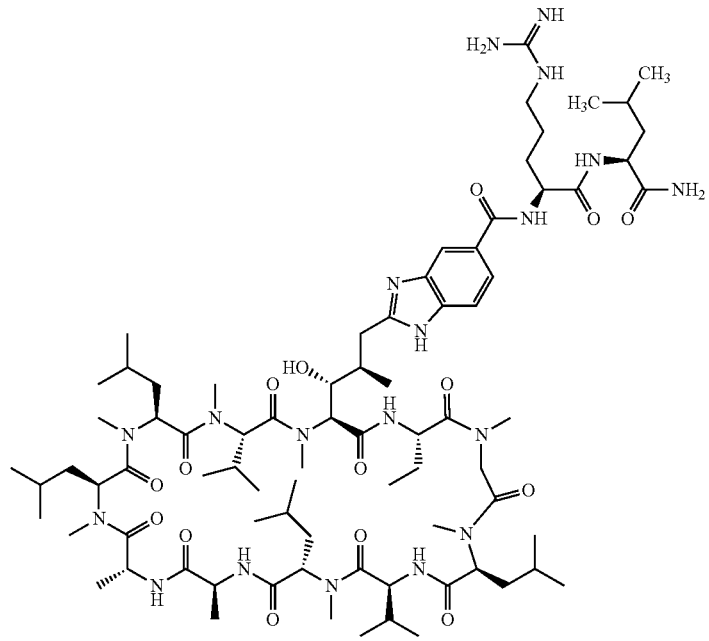
Compound 59
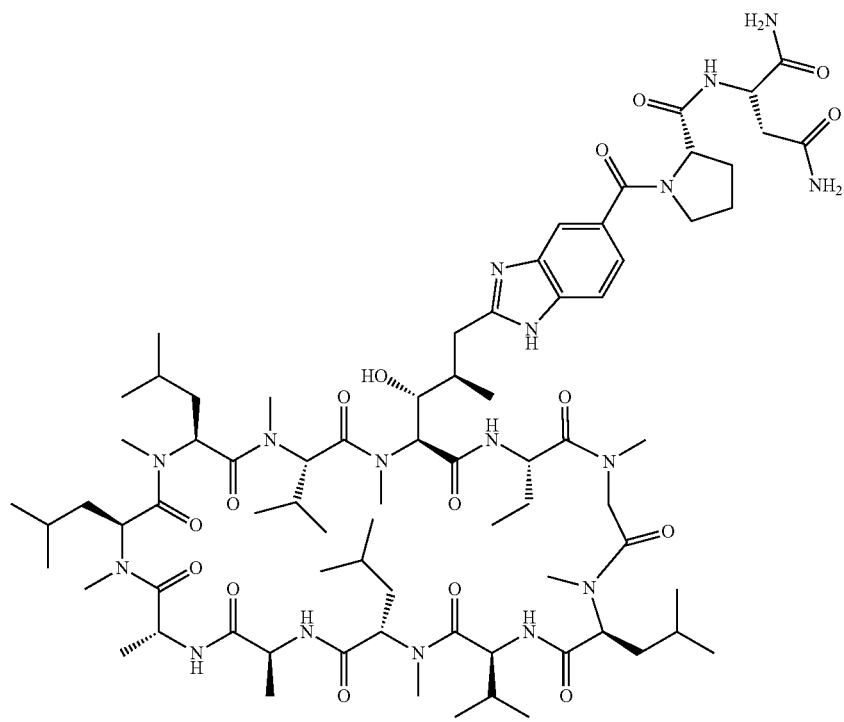

-continued
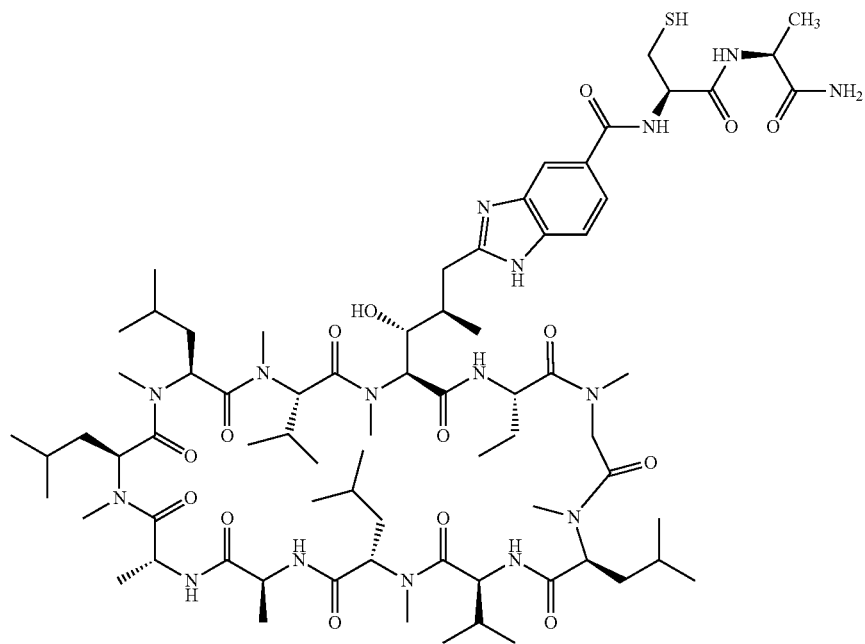
Compound 60
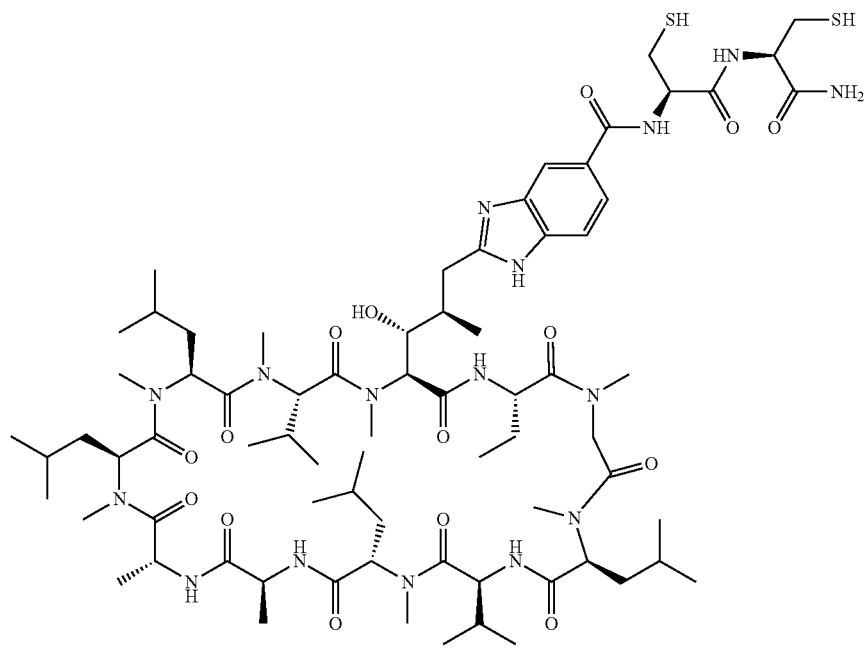
Compound 61

-continued
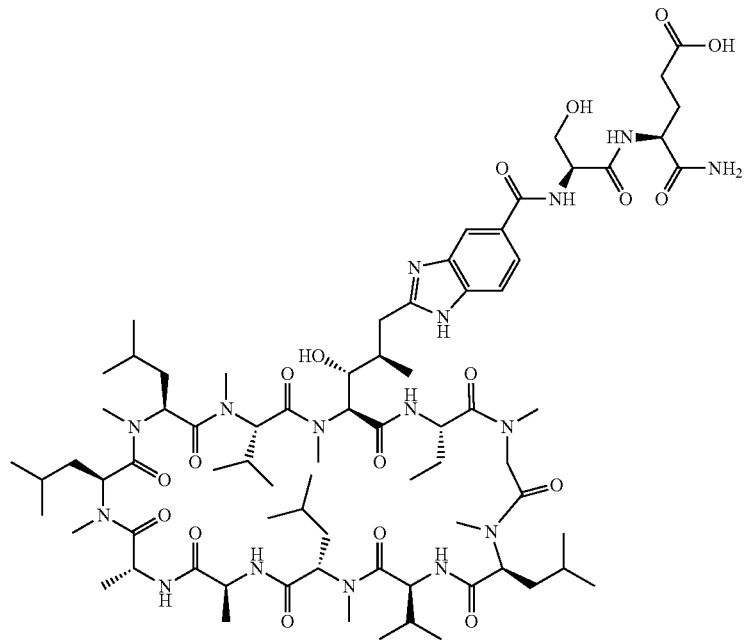
Compound 62
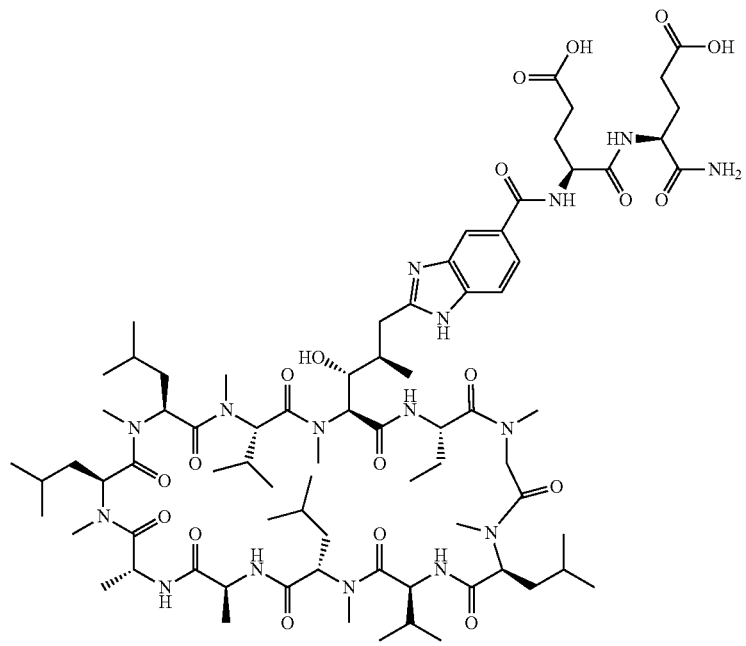
Compound 63

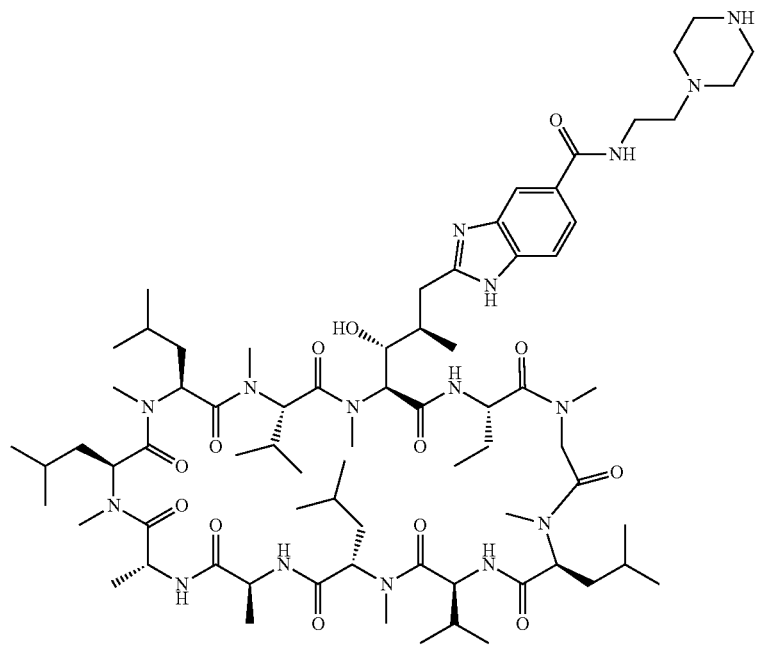
Compound 64
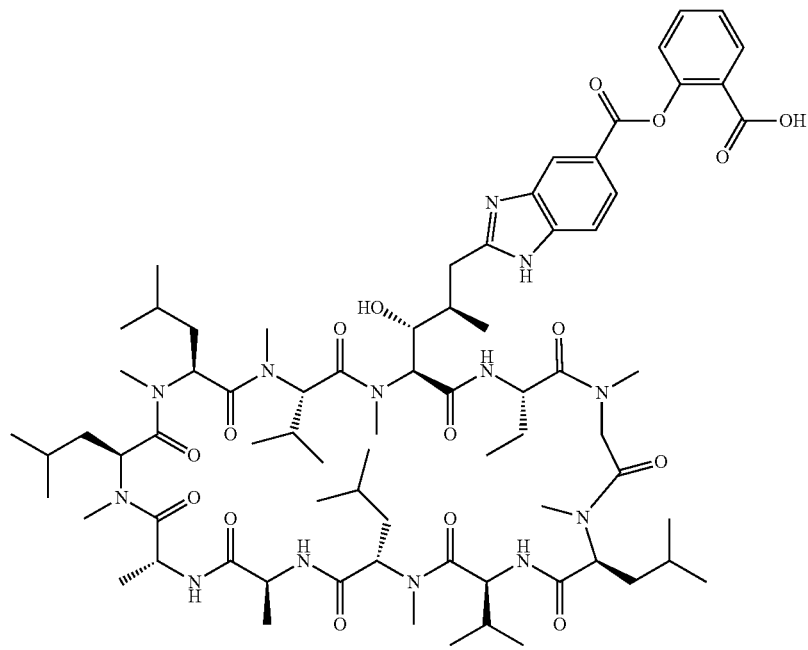
Compound 65

-continued
Compound 66
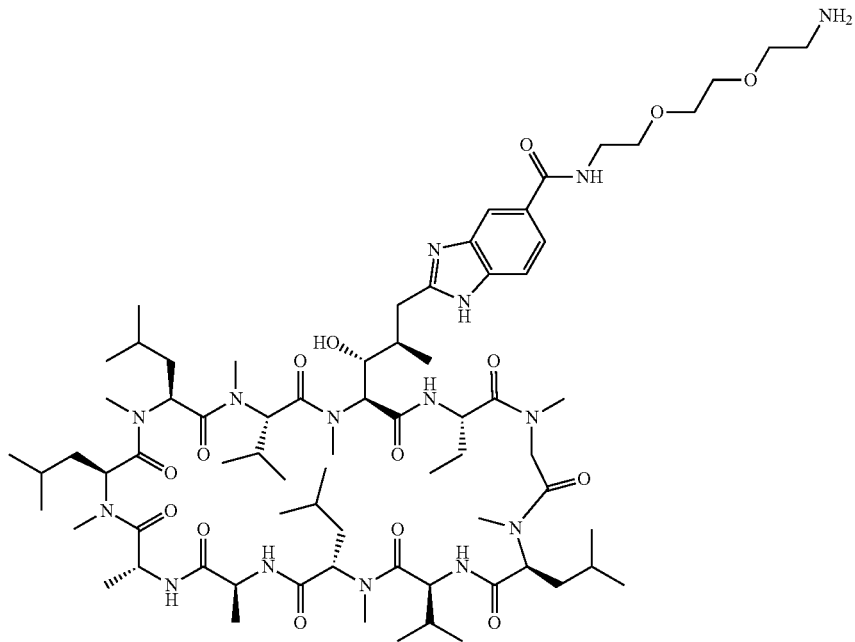
Compound 67
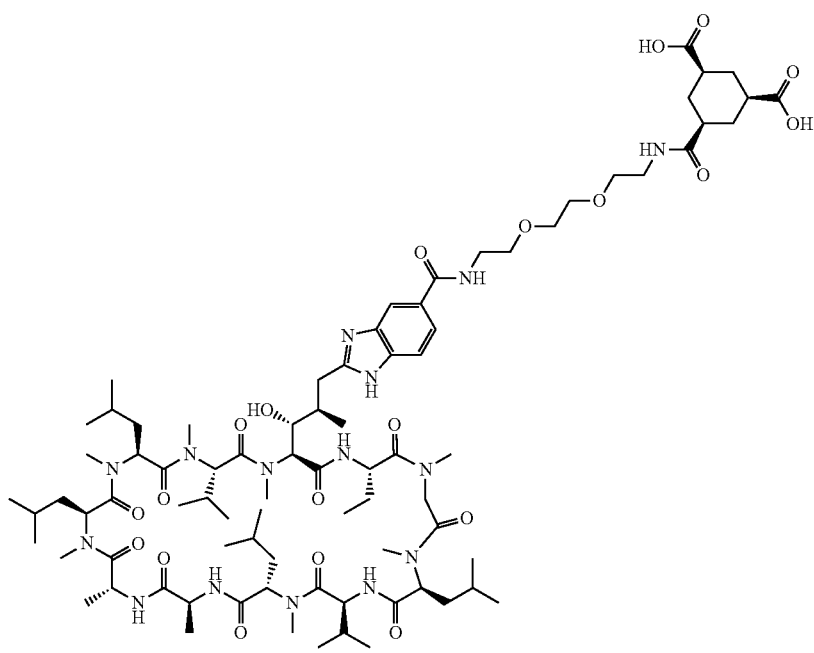

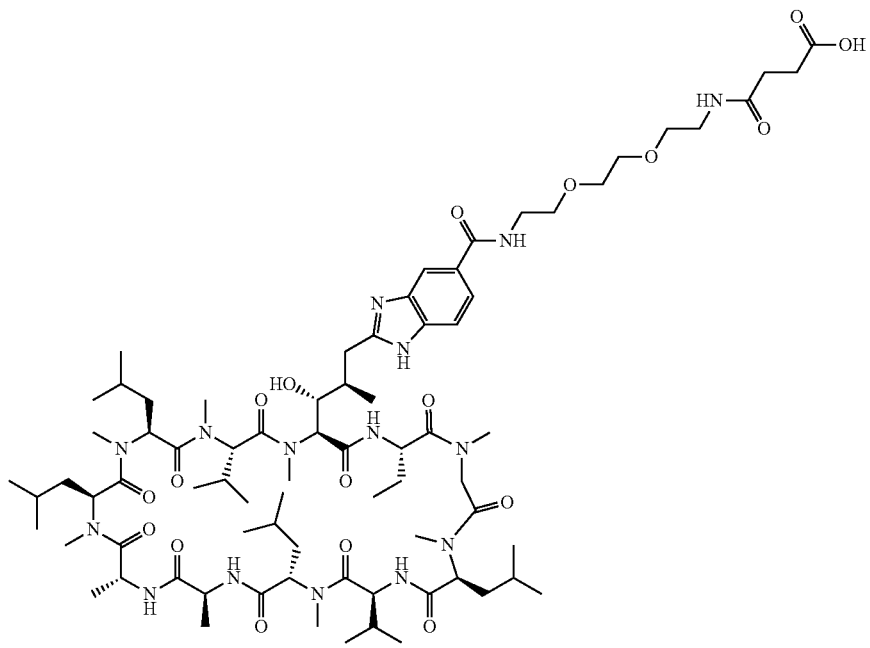

Compound 68

The groups listed above and below in this application are binding at the position where the bond ends at a wavy line.

If tautomeric forms of compounds 4 to 68 are possible, said tautomeric forms should also be covered by the indicated tautomer and they should be object of the present application.

According to the current invention compounds 5, 13, 20, 22, 28, 31, 33, 34, 35, 37, 42, 43, 45, 46 and 48, and in particular compounds 5 and 33 have proved to be particularly preferred.

As used herein the term (C1-C4)-alkyl, respectively (C1-C6)-alkyl is to be understood as a linear or branched alkyl group with 1 to 4, respectively 1 to 6 C-atoms, more preferably with 1 to 4 C-atoms, and even more preferably with 1 to 3 C-atoms. Individual —CH— or —CH$_2$— groups can be replaced by N, NH, O or S. Likewise, one or more H-atoms of the alkyl group can be replaced by fluorine atoms. Examples of such groups are the following: methyl, ethyl, n-propyl, iso-propyl, n-butyl, iso-butyl, s-butyl, t-butyl, 2-methyl-butyl, n-pentyl, s-pentyl, t-pentyl, n-hexyl, 2,2-(di-ethyl)-ethyl, trifluoromethyl, pentafluoroethyl and 2,2,2-trifluoroethyl, wherein methyl and ethyl are preferred.

Within the present application, the term (C2-C6)-alkenyl is to be understood as a linear or branched group of hydrocarbon units with 2 to 6 C-atoms, preferably with 2 to 4 C-atoms and especially preferred with 2 to 3 C-atoms, wherein 1 or several double bonds, and preferably one double bond is present between two C-atoms. Individual —CH— or —CH$_2$— groups can be replaced by N, NH, O or S. Also, 1 or several H-atoms of the alkenyl group can be replaced by fluorine atoms. Examples of such groups are the following: ethenyl, propenyl, butenyl, pentenyl, hexenyl. The residues ethenyl and propenyl are especially preferred.

Within the present invention, the term —NH(C1-C4-alkenyl) is to be understood as an above defined (C1-C4)-alkenyl, which is bound via a —NH— unit. Same preferences as for (C1-C4)-alkenyl apply also here.

As used within the present invention, the term (C3-C6)-cycloalkyl is to be understood as a cyclic hydrocarbon group with 3 to 6 cyclic C-atoms. Individual —CH$_2$— groups can be replaced by N, NH, O or S. Also, 1 or several H-atoms of the alkyl group can be replaced by fluorine atoms. Examples for such groups are the following: cyclopropyl, cyclobutyl, cyclopentyl and cyclohexyl. Cyclohexyl is especially preferred.

As used within the present invention, the term (C1-C6)-alkoxy, respectively —O(C1-C4-alkyl) is to be understood as an above defined (C1-C6)-alkyl respectively (C1-C4)-alkyl, which is bound via an oxygen atom. Herein, methoxy and ethoxy are especially preferred.

As used within the present invention, the term (C1-C6)-alkylthio is to be understood as an above defined (C1-C6)-Alkyl, which is bound via a sulfur atom. Herein, methylthio and ethylthio are particularly preferred.

As used within the present invention, the term (C1-C6)-alkylsulfonyl is to be understood as an above defined (C1-C6)-alkyl, which is bound via a sulfonyl group. Herein, methylsulfonyl and ethylsulfonyl are especially preferred.

According to the present invention, the term —COO((C1-C4)alkyl)) is to be understood as an above defined (C1-C4)-alkyl, which is bound via a —COO-group, wherein the (C1-C4)-alkyl binds to the oxygen atom. Herein, —COO-methyl and —COO-ethyl are especially preferred.

According to the present invention, the term (C1-C6) alkyl-amino respectively, —NH(C1-C4-alkyl) is to be understood as an above defined (C1-C6)-alkyl, respectively (C1-C4)-alkyl that binds via an —NH— unit. Examples include methylamino and ethylamino.

According to the present invention, the term (C1-C6) dialkyl-amino is to be understood as a secondary amino group bearing the two (C1-C6)-alkyl defined as above. Examples include dimethylamino and diethylamino.

The term (substituted) aryl is understood within the present invention as a mono- or polycyclic (preferably mono-, bi- or tricyclic) aromatic or heteroaromatic hydrocarbon residue with preferably 5, respectively 6 to 10, and even more preferably 5 to 6 aromatic ring atoms. The aromatic or heteroaromatic hydrocarbon residue can carry furthermore substituents.

In this context the term aromatic respectively heteroaromatic unit is understood either as a single aromatic cycle, such as benzene, respectively a single heteroaromatic cycle such as pyridine, pyrimidine, thiophene, etc., or as a condensed aryl- or heteroaryl group, such as naphthalene, quinoline, isoquinoline, benzothiophene, benzofuran and indole etc. Hence, according to the present invention examples of an aromatic or heteroaromatic unit are: benzene, naphthalene, furan, benzofuran, isobenzofuran, thiophene, benzothiophene, isobenzothiophene, pyrrole, indole, isoindole, pyridine, quinoline, isoquinoline, pyrazole, indazole, imidazole, benzimidazole, oxazole, 1,2-thiazole, 1,3-thiazole, benzothiazole, pyridazine, benzopyridazine, pyrimidine, benzopyrimidine, quinoxaline, pyrazine, phenazine, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purin, pteridine and indolizine. Preferred are herein benzene, naphthalene, furan, thiophene, pyrrole, pyrimidine, pyrazine, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purin, pteridine, and especially preferred benzene.

According to the present invention, the term (substituted) O-aryl respectively (substituted) NH-aryl is to be understood as an above defined (substituted) aryl that binds via an oxygen atom or a —NH— unit.

The substituent on the substituted aryl can be for example: methyl, ethyl, methoxy, ethoxy, fluoro, chloro, bromo, trifluoromethyl, pentafluoroethyl, —OH, —SH, —NH$_2$, —CN or —NO$_2$.

As above mentioned, a further embodiment of the present invention is directed to a tracer-coupled compound, which comprises a compound of aforementioned formula I and a tracer compound (tracer) that are linked to each other via a covalent bond. The linkage of the compound of the formula I is present in a way that instead of a terminal atom or a terminal group of the compound of formula I a bond to the tracer, possibly through a linker, is present The tracer is preferably covalently bound to the compound of formula I. However, the tracer can in principle be bound to the active agent in any manner known to the skilled person as being suitable for the purpose of the invention. Especially preferred is that the tracer is covalently bound via a linker to the compound of formula I.

Within the scope of this invention the linker can be any group that is known to the skilled person as being suitable for the objective of the invention. Preferably, it refers to a group, which is free of a protease cleavage site. Especially preferred, the linker is selected from groups forming an inter-atomic distance of four to 40 atoms, preferably 5 to 30 atoms, and most preferably 6 to 20 atoms.

According to the present invention, under the term "tracer" are encompassed substances, such as dyes, voltage-sensitive indicators, pH indicators, calcium-sensitive indicators, radioactive elements, NMR-labels or electron spin labels, which were described several times in the scientific literature (WO/2005/022158, EP 0649022, U.S. Pat. No. 6,596,499, U.S. Pat. No. 7,090,995, U.S. Pat. No. 4,672,044). The term tracer comprises according to the present invention individual atoms or molecules that are covalently bound to the active agent molecule. Thereby, one tracer and also several tracers can be directly, covalently bound to the active agent molecule.

The tracer and also the several tracers can also be bound to a multifunctional linker or the tracer and also the several tracers can be covalently bound within an acidic peptide or terminally on an acidic peptide.

Within the scope of this invention, "dyes" are substances that may be optically verified by detection of the radiation emitted by them or by the electromagnetic radiation not being absorbed by them. These includes for example dyes like fluorescein isocyanate (FIC), fluorescein isothiocyanate (FITC), (dimethylamino)naphthalene-S-sulfonyl chloride (DANSC), tetramethylrhodamine isothiocyanate (TRITC), lissamine rhodamine B200-sulfonyl chloride (RB 200 SC) etc. A description of numerous suitable molecules can be found exemplarily in DeLuca, "Immunofluorescence Analysis", in "Antibody As A Tool", Marchalonis et al., Eds., John Wiley & Sons, Ltd., pp. 189-231, (1985).

Within the scope of this invention, "voltage-sensitive indicators" are substances, which depending on an applied electrical potential difference or on the present electrical potential change their physical, optical or catalytic properties thus, causing a detectable signal. Voltage-sensitive indicators such as DIBAC (Japanese Journal of Pharmacology 86(2001) 342-350, American Journal of Physiology—Heart & Circulatory Physiology 287(2004) H985-H993) are known to the skilled person.

Within the scope of this invention, "pH indicators" are substances, which depending on the pH value change their physical, optical or catalytic properties thus, causing a detectable signal. Such indicator dyes, like for example phenol red, bromothymol blue, bromophenol blue and many others are known to the skilled person.

Within the scope of this invention "calcium-sensitive indicators" are substances, which in the presence of calcium change their physical, optical or catalytic properties thus causing a detectable signal. Calcium-sensitive indicators known to the skilled person are for example aequorin and other calcium-sensitive dyes such as FURA-2.

"Radioactive elements" according to this invention generate for example gamma radiation like for example the following isotopes $^{124}$I, $^{125}$I, $^{128}$I, $^{131}$I, $^{132}$I or $^{51}$Cr, wherein $^{125}$I is particularly preferred. Others like for example $^{11}$C, $^{18}$F, $^{15}$O or $^{13}$N, can be detected by their positron emission and suitable detectors (positron-emission-radiography) and others, like for example $^{111}$In can be detected by electron capture.

According to this invention, "NMR-labels" are substances containing atoms with odd number of nucleons (sum of protons and neutrons). Such atomic nuclei, for example $^{13}$C, $^{15}$N or $^{19}$F, posses a nuclear spin and therefore, a nuclear magnetic moment.

"Electron spin labels" serve within the scope of this invention to measure the "electron paramagnetic resonance" using electron spin resonance. Hence, the microwave absorption of a sample is measured in an external magnetic field. Thus, molecules having a permanent magnetic moment (unpaired electrons) can be detected (Physics in Medicine & Biology. 43(1998)U 3-U 4, Clinical Chemistry & Laboratory Medicine. 46(2008) 1203-1210).

The use of tracers is particularly advantageous if the tracer-coupled compound of the aforementioned formula I is used in a diagnostic method (such as anamnesis inquiry, physical examination, use of imaging techniques such as X-ray/MRI or analysis with laboratory values of the blood or other body fluids). If the compounds of formula I according to the present invention further contain one or several tracers, the distribution volume of the active agent can be detected based on said tracers. Tracers can be furthermore used to quantify the active agent.

Such an—as an example mentioned—tracer-coupled compound according to this invention is for example the following compound 69:

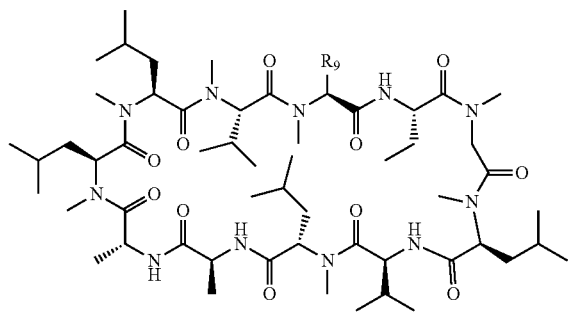

wherein R$_9$ corresponds to the following structure:

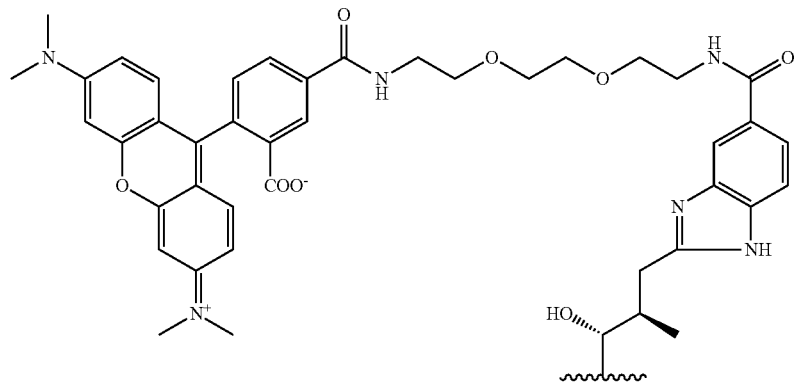

Another embodiment of the present invention is directed to a compound of the aforementioned formula I or the tracer-coupled compound according to the present invention for use in medicine. In other words, a compound of general formula I is used as a pharmaceutically-active substance respectively a drug, the tracer-coupled compound according to the present invention is used as a diagnostic agent in medicine. The inventive compound can be used for the manufacture of any drug appearing to the skilled person as being suitable for the compound of the present invention. Preferably, the inventive compound is used for the manufacture of a non-immunosuppressive drug. Drugs are considered to be non-immunosuppressive, if they do not decrease the functions of the immune system.

The drugs or the compounds according to the invention, respectively, (in the following only called drugs) can thereby be administered in any form, which is known to the skilled person as being suitable for the intended purpose. For example the drug can be used in a form selected from the group consisting of injections, infusions, tablets, crèmes, gels, ointments, sprays, capsules, syrups, emulsions, powders, flour, suppositories, or similar. In this context, it is especially preferred that the drug is used in form of sprays, ointments, injections or tablets. Thereby, additives are very often needed that convert the drug in a dosage form to be administrable.

Therefore, one further embodiment of the present invention is directed to a pharmaceutical preparation, which contains a compound of the aforementioned formula I and preferably one or several additives.

The choice of the additive depends hereby specifically on the type of the dosage form. Preferred are such additives, which are physiologically acceptable and per se not pharmaceutically active The pharmaceutical preparation can be each pharmaceutical preparation known to the skilled person as being suitable. In a preferred embodiment the pharmaceutical preparation is a spray, ointment, injection or tablet.

Application range of the compounds of the aforementioned formula I, the pharmaceutical preparation according to the invention and the tracer-coupled compounds according to the invention can be therapy and diagnostics of disease, but also cosmetics. Therapy is primarily understood as meaning the therapy of disease of human and animals.

Special advantages of the compounds according to the aforementioned formula I, of the pharmaceutical preparations according to the invention and of the tracer-coupled compounds according to the invention are inherent in the animal and human medicine, with the application of substances on or in cell suspensions, tissue cultures, transplants or the whole mammal.

The present invention is furthermore directed to the use of compounds of the aforementioned formula I respectively of the pharmaceutical preparation according to the invention, in particular of the tracer-coupled compounds according to the invention as agents for diagnosis.

In a further embodiment, the present invention refers to a compound according to the aforementioned formula I or a pharmaceutical preparation according to the invention for the treatment of the following diseases:
  a) viral infections
  b) acute and chronic inflammatory diseases
  c) cancer
  d) degenerative muscle diseases
  e) neurodegenerative diseases, and
  f) disorders which are associated with an impairment of calcium homeostasis.

In other words, the present invention is also directed to the use of a compound of the aforementioned formula I or the pharmaceutical preparation of the invention for the manufacture of a medicament for the treatment of the diseases mentioned above under a) to f). In still other words, the present invention is directed to a method for the treatment of one of the diseases mentioned above under a) to f) in an individual in need of treatment comprising the administration of a therapeutically effective amount of a drug comprising/consisting of a compound according to the aforementioned formula I or the pharmaceutical preparation of the invention. The individual to be treated is preferably a mammal. Mammals may be humans and animals.

In another embodiment, the present invention refers to a tracer-coupled compound according to the invention for the diagnosis of the following diseases:
a) viral infections
b) acute and chronic inflammatory diseases
c) cancer
d) degenerative muscle diseases
e) neurodegenerative diseases, and
f) disorders which are associated with an impairment of calcium homeostasis.

In other words, the present invention is also directed to the use of a tracer-coupled compound of the invention for the manufacture of a medicament for diagnosis of the diseases mentioned above under a) to f). In still other words, the present invention is directed to a method for the diagnosis of one of the diseases mentioned above under a) to f) in an individual in the need of treatment comprising the administration of a diagnostically effective amount of a drug comprising/consisting of a tracer-coupled compound according to the invention. The individual to be treated is preferably a mammal. Mammals may be humans and animals.

According to the invention, the aforementioned viral infection is preferably caused by viruses such as HIV, hepatitis A, hepatitis B, hepatitis C, hepatitis D, and hepatitis E.

According to the invention, the aforementioned inflammatory disease includes preferably asthma, chronic inflammations, chronic prostatitis, glomerulonephritis, multiple chemical sensitivity, inflammatory intestinal diseases, sepsis, inflammation of the vascular smooth muscle cells, aneurysm, inflammation in the pelvic area, reperfusion injury, rheumatoid arthritis, and vasculitis.

According to the invention the aforementioned cancer disease is understood as meaning preferably—but not exclusively—lung cancer, cancer of the bladder, hepatic cancer, pancreatic cancer, and breast cancer.

According to the invention, the aforementioned degenerative muscle disease is preferably directed to muscle dystrophy, collagen IV-myopathies, and the myocardial reperfusion injury.

According to the invention, the aforementioned neurodegenerative disease is preferably selected from: Alzheimer's disease, Parkinson's disease, Huntington's disease, multiple systemic atrophy, multiple sclerosis, cerebral poliomyelitis, stroke, diabetic neuropathy, amyotrophic lateral sclerosis, spinal cord injuries, and cerebral sclerosis.

According to the invention, the aforementioned disease associated with an impairment of calcium homeostasis, refers preferably to myocardial infarct, stroke, acute hepatic toxicity, cholestasis, and reperfusion injury of transplanted organs.

Compounds of the aforementioned formula I of the present invention are not immunosuppressive, extracellular effective inhibitors of the enzymatic activity of extracellular cyclophilins. As such, the compounds are suitable for the treatment and/or prevention of cyclophilin mediated acute and chronic diseases. The compounds are preferably, but not only, suitable for the treatment or prevention of persistent or chronic inflammatory diseases, neurogenic inflammation as well as inflammation associated fibrosis and edema formation. This includes, but is not limited to acute inflammatory overreaction (burning, post-operative inflammation), gastro intestinal inflammation (colitis, Addison's Disease), sepsis, disease of the respiratory system (asthma, chronic obstructive pulmonary disease), inflammatory vasculopathies (atherosclerosis, reperfusion injury), rheumatoid arthritis, inflammatory skin diseases (psoriasis, atopic dermatitis), eye diseases (keratoconjunctivitis) and inflammatory diseases of the peripheral and central nervous system (Parkinson's disease, stroke, multiple sclerosis).

In another aspect, the present invention is directed to a method for accumulation of active agents in an intracellular space of a multi-cellular object, comprising the steps:

Providing a compound according to the aforementioned formula I or a tracer-coupled compound according to the invention;

Contacting one of said compounds with a multi-cellular object.

In particular, the accumulation within the method of the invention refers to an in-vitro-accumulation. This means that the multi-cellular object is an object separated from the living organism.

The "extracellular space" should refer to all areas, which are outside of the cytosol and the membrane enclosing the cytosol. For example, the culture medium present in cell suspension is included, too.

The multi-cellular object can be any object that consists of at least two identical or different biological cells.

The term "biological cell" thereby comprises human, animal as well as plant and bacterial cells, as well as unicellular organisms. If the biological cells are bacterial cells or unicellular organisms, then the term "multi-cellular object" refers to a conglomeration of several cells as, for example, a cell colony or a bacterial culture. If the biological cells are human or animal cells, then the term "multi-cellular object" refers to a separated body part, such as a transplant, in particular an organ-, a cell-, an extremities- or a tissue-transplant, blood or a blood fraction, such as blood plasma or an in-vitro culture of human and/or animal cells, as for example a two-dimensional tissue culture or a spheroid culture of cells. If the biological cells are plant cells, then the term "multi-cellular object" refers to a part of a plant, such as for example leaves, root or stem but also to a whole plant.

According to the invention, the multi-cellular object is a separated organ or a body-part, blood or a blood fraction, a cell culture or a plant.

Furthermore, the present invention is directed to the use of a compound of the below shown formula XIV, which derives from cyclosporin A and covers compounds 1 to 3, for the preparation of a compound according to the aforementioned formula I or of the tracer-coupled compound according to the present invention. In other words, the present invention is also directed to a method for the preparation of such a compound according to the aforementioned formula I or tracer-coupled compounds according to the present invention using a compound of formula XIV.

Compound of formula XIV:

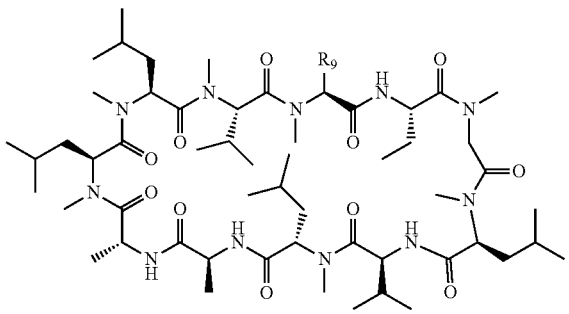

wherein $R_9$ represents a residue of the following formula:

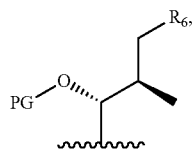

wherein $R_8$ represents —CHO or —COOH; and
wherein PG represents an alcohol protective group. The protective group PG is able to protect a hydroxyl group so that it remains unchanged during the transformation of other functional groups in the molecule or that the unprotected hydroxyl group does not disturb these transformations. Examples of said protective groups as well as methods for their introduction and their cleavage are described in P. G. M. Wuts and T. W. Greene: "Protective Groups in Organic Synthesis", 4. edition, 2006; chapter "Protection for the hydroxyl group". Preferred protective groups are ether, in particular substituted ether such as e.g. methoxymethyl-, methylthiomethyl-, benzyloxymethyl-, tert-butoxymethyl-, 2-methoxyethoxymethyl-, 2-(trimethylsilyl)ethoxymethyl-, 2,2,2-trichloroethoxymethyl-, tetrahydropyranyl-, tetrahydrofuranyl-, 1-ethoxyethyl-, 1-methyl-1-methoxyethyl-, 1-methyl-1-benzyloxyethyl-, 2,2,2-trichloroethyl-, 2-(trimethylsilyl)ethyl-, allyl-, benzyl-, 4-methoxybenzyl-, 3,4-dimethoxybenzyl-, diphenylmethyl- or triphenylmethyl ether; silyl ether such as e.g. trimethylsilyl-, triethylsilyl-, triisopropylsilyl-, tert-butyldimethylsilyl-, tert-butyldiphenylsilyl-, triphenylsilyl- or diphenylmethylsilyl ether;
ester such as ester of the formic, acetic, chloroacetic, dichloroacetic, trichloroacetic, trifluoroacetic, pivalic or benzoic acid;
carbonate such as e.g. methyl-, 9-fluoroenylmethyl-, ethyl-, 2,2,2-trichloroethyl-, 2-(trimethylsilyl)ethyl-, isobutyl-, allyl-, 2-propenyl-, 4-nitrophenyl-, benzyl-, 4-methoxybenzyl- or 3,4-dimethoxybenzyl carbonate.

Particularly preferred are ethers such as methoxymethyl ether or tetrahydropyranyl ether, silyl ether such as trimethylsilyl-(TMS), tert-butyldiphenylsilyl-(TBDPS) or tert-butyldimethylsilyl ether (TBDMS) or an ester protective group such as acetyl. Especially preferred are TBDMS and acetyl.

Derivatives of cyclosporin A of the general formula I, which have substituents $R_8$ of the formula IV to formula XIII can be prepared starting from a compound of formula XIV and suitable aromatic, heteroaromatic, aliphatic or heteroaliphatic primary amines presenting an unsubstituted or substituted amino group ($X=NR_1$), a hydroxyl group ($X=O$) or a thiol group ($X=S$) at an adjacent carbon atom. Preferably, the aldehydes of the formula XIV ($R_8$=—CHO) can be used. In case of reaction of aldehydes of the formula XIV with the amines, said reaction is carried out in an inert solvent such as e.g. ethanol, methanol, isopropyl alcohol, tetrahydrofuran (THF), dichloromethane, chloroform, dimethylformamide (DMF), N,N-dimethyl acetamide (DMA), acetonitrile, or ethyl acetate, or also mixtures of said solvents, optionally also in presence of water. Preferred solvents are methanol, acetonitrile or DMF. The reaction can take place at room temperature or at elevated temperature up to boiling of the reaction mixture. Optionally, an oxidizing agent is added for completing the reaction. Examples of oxidizing agents are quinones such as 2,3-dichloro-5,6-dicyano-14-benzoquinone (DDQ); diacetoxyiodobenzene; benzofuroxan; nitrobenzene; dimethylsulfoxide (DMSO); metallic compounds with metals having a higher oxidation state such as e.g. barium manganate, manganese dioxide, nickel oxide, lead tetraacetate, pyridinium chlorochromate, scandium(III) triflate, ytterbium(III) triflate, copper(II) triflate, manganese triacetate;
halogens such as e.g. iodine; tert-butyl hypochlorite;
sulphur compounds having a higher oxidation state such as oxone, sodium metabisulfite, sodium hydrogen sulfite, potassium bisulfate, potassium monopersulfate; N-bromosuccinimide; N-chlorosuccinimide; N-iodosuccinimide or oxygen of the air.

Preferred oxidizing agents are N-bromosuccinimide or atmospheric oxygen. The reaction of the amines with carboxylic acids of the formula XIV ($R_5$=—COOH) can be carried out in presence of strong acids such as e.g. polyphosphoric acid, in particular at elevated temperature. In one preferred variant, the reaction is carried out in two steps, wherein firstly, an amide is obtained starting from a carboxylic acid of formula XIV and an amine with elimination of water, and using said amide, in a second step the heterocyclic compound of formula I is prepared with repeated elimination of water. For preparation of the amide, may be used reagents that are known to a skilled person for forming an amide bond under dehydration conditions, e.g. using (benzotriazol-1-yl)-oxytripyrrolidinophosphonium hexafluorophosphate (PyBOP) in presence of a base such as e.g. diisopropylethylamine (DIPEA). The second step can for example take place by heating with an anorganic acid chloride such as thionyl chloride or $POCl_3$, by heating in presence of an acid such as p-toluene sulfonic acid in a solvent such as toluene or xylene, by heating in an organic carboxylic acid such as acetic acid or propionic acid or in presence of water eliminating reagents such as e.g. dicyclohexylcarbodiimide (DCC). Compounds of formula I may also be transformed into other compounds of formula I, by transforming substituents $R_2$, $R_3$, $R_4$, $R_5$, $R_{10}$ or $R_{11}$, which are bound to groups $R_8$ of the formula IV to formula XIII using standard reactions of organic synthesis known to the skilled person. For example, nitro groups can be reduced to amino groups. Amino groups can be converted to sulfonamides using sulfonyl chlorides or to amides using acyl chlorides or other activated carboxylic acid derivatives. Carboxylic acids $R_2$=—COOH can be transformed to their esters using alkyl halogenides. Also, under similar reaction conditions, a compound of formula I, with X=NH, can be converted to a compound X=N(C1-C4-alkyl) or N-benzyl. Furthermore, carboxylic acids $R_2$=—COOH can be transformed to corresponding carboxylic acid amides using primary or secondary amines under standard amide coupling conditions.

One embodiment (i) of the present invention is directed to a pharmaceutical preparation containing a compound of formula I according to the invention or a tracer-coupled compound according to the invention.

Another embodiment (ii) of the present invention is directed to a method for the treatment/diagnosis of the following diseases a) to f) in an individual in need of a treatment comprising the application of a therapeutically effective dose of a drug comprising a compound according to formula I or an inventive pharmaceutical preparation according to embodiment (i):

a) viral infections b) acute and chronic inflammatory diseases c) cancer d) degenerative muscle diseases e) neurodegenerative diseases, and f) disorders, which are associated with an impairment of calcium homeostasis.

Another embodiment (iii) of the present invention is directed to a method according to embodiment (ii) for the treatment of viral infections caused by viruses such as HIV, hepatitis A, hepatitis B, hepatitis C, hepatitis D, and hepatitis E, asthma, chronic inflammations, chronic prostatitis, glomerulonephritis, multiple chemical sensitivity, inflammatory intestinal diseases, sepsis, inflammation of the vascular smooth muscle cells, aneurysm, inflammation in the pelvic area, peritonitis, reperfusion injury, rheumatoid arthritis, vasculitis, lung cancer, cancer of the bladder, hepatic cancer, pancreatic cancer, breast cancer, muscle dystrophy, collagen IV-myopathies, myocardial reperfusion injury, Alzheimer's disease, Parkinson's disease, Huntington's disease, multiple systemic atrophy, multiple sclerosis, cerebral poliomyelitis, stroke, diabetic neuropathy, amyotrophic lateral sclerosis, spinal cord injuries, cerebral sclerosis, myocardial infarct, stroke, acute hepatic toxicity, cholestasis, reperfusion injury of transplanted organs, asthma, psoriasis, atopic dermatitis and ulcerative colitis.

Another embodiment (iv) of the present invention is directed to a method for accumulation of active agents/diagnostic agents in an extracellular space of a multi-cellular object, comprising the steps:

Providing an inventive compound according to formula I or a tracer-coupled compound according to the invention;

Contacting one of said compounds with the multi-cellular object.

Another embodiment (v) of the present invention is directed to a method for the preparation of a derivative of cyclosporin A according to the invention by reacting a compound of the following formula

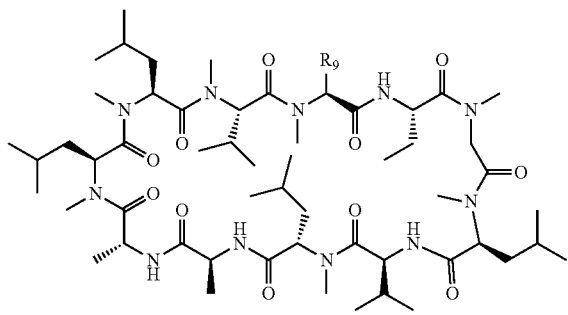

wherein $R_9$ represents a residue of the following formula:

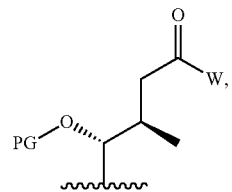

wherein PG represents an alcohol protective group and W is H or OH and the respective residue is linked via the bond at which end a wavy line is drawn in.

Another embodiment (vi) of the present invention is directed to a method for the preparation of a tracer-coupled compound by reaction of a compound according to formula I with a tracer containing compound.

FIGURES AND EXAMPLES

The present invention should now be described in more detail on the basis of the following figures and examples. The figures and examples have only an illustrative character and should in no way limit the scope of the present invention.

There are:

FIG. 1: FIG. 1 shows two diagrams, in which the corresponding concentration of compounds 5 and 33 are plotted against the percent of the control. In other words the diagrams in FIG. 1 show the cell permeability of compound 5 and 33, as well as cyclosporin A in Jurkat-cells.

FIG. 2: Verification of the immunosuppressive effect of compound 5 compared to cyclosporin A in proliferation assay.

FIG. 3: Influence of 200 μg of compound 5 on the number of the eosinophilic granulocytes (eosinophils) in bronchial lavage.

FIG. 4: Influence of 200 μg of compound 5 on the number of the eosinophilic granulocytes (eosinophils) in lung tissue.

FIG. 5: Influence of compound 5 on the number of the CD4-positive T-cells in the bronchial lavage.

FIG. 6: Influence of compound 5 on the number of the CD4-positive T-cells in the lung tissue.

EXAMPLES

The following abbreviations are used in the examples:
CsA cyclosporin A
DBU 1,8-diazabicyclo[5.4.0]undec-7-ene
DCM dichloromethane
DIC N,N'-diisopropylcarbodiimide
DIPEA diisopropylethylamine
DMAP 4-(dimethylamino)pyridine
DMEM Dulbecco's Modified Eagle Medium
DMF N,N-dimethylformamide
DMSO dimethylsulfoxide
DTT dithiothreitol
EDO ethylene dioxide
ES electro spray
FACS Fluorescence Activated Cell Sorter
FCS Fetal Calve Serum
FITC fluoresceinisothiocyanate
Fmoc fluorenylmethoxycarbonyl
FSC Forward Scatter
HATU 2-(7-aza-1H-benzotriazol-1-yl)-1,1,3,3-tetramethyluronium hexafluorophosphate
HBSS Hank's Buffered Salt Solution HOAc acetic acid
HPLC High-performance Liquid Chromatography
MeOH methanol
MS mass spectrum
MTT (methylthiazol-2-yl)-diphenyltetrazolium bromide
NMP N-methylpyrrolidone
OVA ovalbumin
Pbf 2,2,4,6,7-pentamethyldihydrobenzofuran-5-sulfonyl
PBS Phosphate Buffered Saline
PMA phorbol myristate acetate
PyBOP (benzotriazol-1-yl)oxytripyrrolidinophosphonium hexafluorophosphate
SSC Side Scatter
TAM RA tetramethyl-6-carboxyrhodamine
TBDMS tert-butyldimethylsilyl
TFA trifluoro acetic acid
THF tetrahydrofuran
Trt trityl

Example 1

Synthesis of Compound 1 (acetyl-CsA-aldehyde)

A solution of sodium periodate (1.03 mg; 4.81 mmol) in water (7 ml) was carefully added dropwise to a solution of acetyl-cyclosporin A (3.0 g; 2.4 mmol) and ruthenium (III) chloride hydrate (25 mg; 0.125 mmol) in a mixture of acetonitrile (30 ml) and water (4 ml). Subsequently, the mixture was stirred overnight at room temperature. Then, ethyl acetate (225 ml) was added and extracted using saturated saline solution (3×111 ml). The organic phase was dried over $MgSO_4$ and subsequently in vacuo. Compound 1 could be separated from the acetyl-CsA carboxylic acid (compound 3) formed as by product using flash-chromatography (300 g silica gel, 0.043-0.063 mm; solvent: 0.1% acetic acid in ethyl acetate). A yield of 1.76 g (60%) of compound 1 was obtained.

Example 2

Synthesis of Compound 2 (TBDMS-CsA-aldehyde)

Step 1:
A solution of cyclosporin A (4.0 g; 3.33 mmol) in dry methylene chloride (20 ml) was cooled to −20° C. under a protective atmosphere of nitrogen. Subsequently, at this temperature 2,6-lutidine (1.43 g; 13.3 mmol) and tert-butyldimethylsilyl trifluoromethanesulfonate (1.76 g; 6.66 mmol) were slowly added one after the other. After stirring overnight at room temperature the same amount of the silyl compound was again added and further 3 hours stirred. The solvent was removed in vacuo, the remainder chromatographed (silica gel; dichloromethane/methanol 100:0-90:10) and 4.2 g TBDMS-CsA were obtained.

Step 2:
Ruthenium(III)chloride hydrate (33 mg; 0.16 mmol) was added to a solution of TBDMS-CsA (4.2 g; 3.19 mmol) in a mixture of acetonitrile (80 ml) and water (10 ml). Subsequently, a solution of sodium periodate (1.36 g; 6.36 mmol) in water (30 ml) was slowly added dropwise. After stirring overnight it was filtered, the filtrate largely concentrated in vacuum and mixed with ethyl acetate. The organic phase was washed with saturated saline solution, dried over $Na_2SO_4$ and concentrated. The remainder was chromatographed (gradient: cyclohexane/ethyl acetate) and thereby, TBDMS-CsA-aldehyde was obtained, which was used without further cleaning in the following reactions. Yield: 78 g (64% over two steps); MS (ES) $C_{66}H_{121}N_{11}O_{13}Si$ calculated 1304. found 1305 $(M+H)^+$.

Example 3

Synthesis of Compound 3 (acetyl-CsA-carboxylic acid)

The compound was synthesized according to a literature procedure (Bioconjugate Chem 3 (1992), 32-36) by oxidation of acetyl-cyclosporin A with sodium periodate/potassium permanganate.

Example 4

Synthesis of Compound 4

50 mg (0.041 mmol) compound 1 and 11.25 mg cis-diamino biotin in 20 ml MeOH were heated for 1 h under reflux and subsequently, stirred at room temperature overnight. After evaporation of the methanol, the remainder was taken in 10 ml DCM, treated with 9 mg N-bromosuccinimide and then, stirred for 1 hour. The acetyl-protected product was subsequently separated by preparative HPLC and lyophilized. Then, the acetyl-protecting group was removed with 3 ml 0.1M LiOH in 50% tetrahydrofuran and the final product was isolated by preparative HPLC. Yield: 10 mg (18%).

Example 5

Synthesis of Compound 5

Method A:
A solution of 100 mg (0.081 mmol) of compound 1 and 190 mg (1.215 mmol, 15 eq) 3,4-diaminobenzoic acid in MeOH (10 ml) was stirred for 12-48 hours until the completion of the reaction (control by analytical HPLC). Subsequently, it was filtered and the solid was washed with 10 ml MeOH. 1.5 ml of the methanolic solution was separated for the next step and the remaining of the filtrate was concentrated in vacuum. The acetyl-compound was subsequently purified by preparative HPLC (column RP C18 250×25 mm; gradient water+0.05% TFA/acetonitrile+0.05% TFA) and obtained after lyophilization as a white solid. Yield: 70 mg (69%).

1.5 ml 0.2M LiOH were added to 1.5 ml of the methanolic solution of the aforementioned acetyl-compound (~6.1 µmol) and mixed until the end of the hydrolysis (about 3 hours; control by analytical HPLC). After acidifying with diluted hydrochloric acid, compound 5 was purified by preparative HPLC (column RP C18 250×25 mm; gradient water+0.05% TFA/acetonitrile+0.05% TFA), lyophilized and isolated as white solid. Yield: 7 mg (87%).

Method B:
Step 1:
An excess of 3,4-diaminobenzoic acid (4.86 g; 31.9 mmol) was added to a solution of TBDMS-CsA-aldehyde (2.78 g; 2.13 mmol) in methanol (10 ml) and the mixture was stirred overnight by directing a weak air flow through it. It was filtered, the filtrate was concentrated and the remainder was used without further purification in the next step. MS (ES) $C_{73}H_{125}N_{13}O_{14}Si$ calculated 1436. found 1437 $(M+H)^+$.

Step 2:

The remainder of the previous step was mixed with a 1M-solution of tetrabutylammonium fluoride in THF (15 ml; 15 mmol) and the mixture was stirred for 2.5 hours until the TBDMS-compound could not be anymore detected. The solution was used directly, without separation of the solvent, for separation by RP-HPLC (column C18; gradient $H_2O$ (0.1% TFA)/MeOH (0.1% TFA)), and compound 5 was obtained after lyophilization as a colorless solid. Yield: 909 mg (32% over two steps); MS (ES) $C_{67}H_{111}N_{13}O_{14}$ calculated 1322. found 1323 $(M+H)^+$.

Example 6

Synthesis of Compound 6

A mixture of acetyl-CsA-carboxylic acid (50 mg; 0.04 mmol), methyl 3-amino-4-hydroxy benzoate (10 mg; 0.06 mmol), benzotriazol-1-yl-oxytripyrrolidinophosphonium hexafluorophosphate (PyBOP) (23 mg; 0.044 mmol) and DIPEA (21 µl) in DMF (3 ml) was stirred overnight and subsequently, the intermediate carboxamide was purified by preparative HPLC. The amide was dissolved in toluene (10 ml), treated with thionylchloride (3 µl) and the solution was heated under reflux for several hours. After a new addition of thionylchloride (10 µl), followed by further heating for 24 hours, HPLC analysis showed a conversion to benzoxazole of approximately 80%. The solvent was removed in vacuo and the remainder was treated with MeOH (1 ml) and 0.2M NaOH (1 ml). The mixture was cooled to 5° C. and stirred overnight. It was acidified with 18% solution of chlorhydric acid (100 µl) and compound 6 was isolated by preparative HPLC purification.

Example 7

Synthesis of Compound 7 and Compound 8

Method A:
A solution of compound 5 (10 mg; 0.00732 mmol) in dry THF was treated with 17 mg $CH_3I$ and 5-6 mg benzyltriethylammonium chloride and shacked overnight at room temperature. After addition of water, the pH was adjusted to approximately 2-3 and the solution was subsequently lyophilized under vacuum. 0.1M LiOH (4 ml) and MeOH (4 ml) were added, and the mixture was stirred for two hours. In addition to compound 7, by preparative HPLC was also compound 8 isolated. Yield: compound 7: 3.5 mg (36%) and compound 8: 1 mg (9%).

Method B:
Compound 7 was prepared as compound 5 (method B), with the difference that the following substances in the following amounts were used: TBDMS-CsA-aldehyde (300 mg; 0.23 mmol) and methyl 3,4-diamino benzoate (38 mg; 0.23 mmol); Yield: 52.3 mg (17%), colorless solid; MS (ES) $C_{68}H_{113}N_{13}O_{14}$ calculated 1336. found 1337 $(M+H)^+$.

Example 8

Synthesis of Compound 9

Method A:
Compound 9 was prepared as compound 5 (method B), with the difference that the following substances in the following amounts were used: TBDMS-CsA-aldehyde (300 mg; 0.23 mmol) and ethyl 3,4-diamino benzoate (42 mg; 0.23 mmol); Yield: 46 mg (15%), colorless solid; MS (ES) $C_{69}H_{115}N_{13}O_{14}$ calculated 1350. found 1351 $(M+H)^+$.

Method B:
25 mg of compound 5 were dissolved in dry THF, treated with 20 mg ethyl bromide, 8 mg $K_2CO_3$ and 5-6 mg benzyltriethylammonium chloride and shacked for 12-48 hours till the completion of the reaction (control by analytical HPLC). Then, the mixture was concentrated in vacuum and separated by preparative HPLC. The acetyl group was cleaved with 4 ml 0.1M NaOH in 50% THF at room temperature within 2 h and the final product was isolated by preparative HPLC. Yield: 10 mg (40%).

Example 9

Synthesis of Compound 10

Compound 10 was prepared as compound 9 in example 8 (method B), with the difference that 1-bromo-2-ethyl butane was use instead of ethyl bromide as alkylating reagent.

Example 10

Synthesis of Compound 11

7 mg of compound 11 were prepared starting from 25 mg of compound 5 and the added 1-bromobutane according to the procedure indicated at example 7 (method A). Yield: 7 mg (28%).

Example 11

Synthesis of Compound 12

5 mg of compound 12 were prepared starting from 25 mg of compound 5 and the added iso-butyl bromide according to the procedure indicated at example 7 (Method A). Yield: 5 mg (20%).

Example 12

Synthesis of Compound 13

The dipeptide H-D-Glu(Ot-Bu)-D-Glu(Ot-Bu)-OH was bound on a 2-chloro-tritylchloride resin via standard fluorenylmethoxycarbonyl(Fmoc)-peptide-synthesis. 152 mg of dipeptide-resin, followed by DIPEA (10 µl) were added to a solution of 13 mg of compound 5 and 4 mg HATU in a mixture of DMF (1 ml) and DCM (1 ml). The reaction mixture was stirred for one hour at room temperature, then the solid was filtrated and washed with DMF (3×), followed by DCM (3×). Compound 13 was cleaved from the resin by stirring for 2 h at 5° C. with 2 ml of 100% trifluoroacetic acid (TFA). After TFA removal in vacuum, the final product was purified by preparative HPLC. Yield: 4 mg (27%).

Example 13

Synthesis of Compound 14

A solution of acetyl-CsA-aldehyde (compound 1; 20 mg) and tert-butyl-3-(3,4-diamino-phenyl)-acrylate (50 mg; 0.21 mmol) in MeOH (1 ml) was shacked at room temperature till completion of the reaction (control by analytical HPLC). The reaction mixture was cooled at 5° C., 0.2M NaOH (1 ml) was added and the reaction mixture was shacked at 5° C. till completion of the hydrolysis (control by analytical HPLC). Then, the reaction mixture was acidified with 18% chlorhydric acid (100 µl) and the product was purified by preparative HPLC. Yield: 5 mg (22.2%).

Example 14

Synthesis of Compound 15

Trifluoroacetic acid (1 ml) was added to ~2.5 mg of compound 14. The mixture was shacked at room temperature for 30 min. After evaporation of TFA in vacuum, the product was purified by preparative HPLC. Yield: 0.3 mg (11.1%).

Example 15

Synthesis of Compound 16

A solution of acetyl-CsA-aldehyde (compound 1; 10 mg; 8 µmol) and 4,5-diamino-2,6-dimercaptopyrimidine (6.9 mg; 40 µmol) in MeOH (1 ml) was shacked at room temperature till completion of the reaction (control by analytical HPLC). Acetate hydrolysis, work-up of the reaction mixture and purification of the compound 16 were performed in the same manner as described for compound 14. Yield: 3.1 mg (28.8%).

Example 16

Synthesis of Compound 17

A solution of acetyl-CsA-aldehyde (compound 1; 10 mg; 8 µmol) and 4,5-diamino-6-hydroxy-2-mercaptopyrimidine (3.2 mg; 18 µmol) in DMF (1 ml) was stirred at 100° C. overnight. After removal of the solvent in vacuum, acetate hydrolysis, work-up of the reaction mixture and the purification of compound 17 were performed in the same manner as described for compound 14. Yield: 1.5 mg (14%).

Example 17

Synthesis of Compound 18

A solution of acetyl-CsA-aldehyde (compound 1; 10 mg; 8 µmol) and 5,6-diamino-1H-pyrimidin-4-one hemisulfate (7.3 mg; 21 µmol) in MeOH (1 ml) was shacked at room temperature till completion of the reaction (control by analytical HPLC). Acetate hydrolysis, work-up of the reaction mixture and purification of the compound 18 were performed in the same manner as described for compound 14. Yield: 0.83 mg (8%).

Example 18

Synthesis of Compound 19

Compound 19 was prepared in the same manner as described in example 17 with the difference that 3,4-diaminobenzoic acid hydrazide (4.4 mg; 26 µmol) was used as diamine. Yield: 2.5 mg (23.4%).

Example 19

Synthesis of Compound 20

Compound 20 was prepared in the same manner as described in example 17 with the difference that 2,3-di-amino-4,5-difluoro-benzene sulfonic acid (3.4 mg; 15 µmol) was used as a diamine. Yield: 2.5 mg (22.4%).

Example 20

Synthesis of Compound 21

Compound 21 was prepared in the same manner as described in example 17 with the difference that 2,3-di-amino-5-fluoro benzoic acid (3.8 mg; 22 µmol) was used as diamine. Yield: 7.6 mg (70.9%).

Example 21

Synthesis of Compound 22

Method A:
Compound 22 was prepared as compound 5 (method B), with the difference that the following substances in the following amounts were used: TBDMS-CsA-aldehyde (300 mg; 0.23 mmol) and 3,4-diaminobenzene sulfonic acid (51.8 mg; 0.275 mmol); Yield: 116.1 mg (37%), colorless solid; MS (ES) $C_{66}H_{111}N_{13}O_{15}5$ calculated 1358. found 1359 $(M+H)^+$.

Method B:
A solution of 10 mg (8 µmol) of compound 1 and 4.9 mg (26 µmol) 3,4-diaminobenzene sulfonic acid in 1 ml MeOH was shacked at room temperature till completion of the reaction (control by analytical HPLC). The reaction mixture was cooled to 5° C. and 0.2M NaOH (1 ml) was added for cleavage of the acetyl protecting group. The reaction mixture was shacked at 5° C. till completion of the hydrolysis (control by analytical HPLC). Then, 100 ml 18% HCl were added and the product was purified by preparative HPLC. Yield: 2.3 mg (21.1%).

Example 22

Synthesis of Compound 23

Method A:
3,4-Diaminobenzamide was obtained following a literature procedure (J. Med. Chem. 48 (2005), 1873-1885) and the diamine (35 mg; 0.23 mmol) was reacted with TBDMS-CsA-aldehyde (300 mg; 0.30 mmol) in the same manner as described for compound 5 (method B). Yield: 43.7 mg (14%), brownish solid; MS (ES) $C_{67}H_{112}N_{14}O_{13}$ calculated 1321. found 1322 $(M+H)^+$.

Method B:
Compound 23 was prepared in the same manner as described in example 17 with the difference that 3,4-diaminobenzonitrile (2.3 mg; 17 µmol) was used as diamine. Yield: 0.4 mg (3.8%).

Example 23

Synthesis of Compound 24

A solution of acetyl-CsA-aldehyde (compound 1; 10 mg; 8 µmol) and 5,6-diaminouracil sulfate (3.2 mg; 14 µmol) in DMF (1 ml) was stirred overnight at a temperature of 100° C. After solvents removal in vacuum, acetate hydrolysis, work-up of the reaction mixture and purification of compound 24 were performed in the same manner as described for compound 14. Yield: 1.7 mg (16.2%).

Example 24

Synthesis of Compound 25

Compound 25 was prepared as compound 5 (method B) with the difference that the following substances in the following amounts were used: iso-propyl 3,4-diaminobenzoate was prepared following a literature procedure (US2007/0032525) and the ester (45 mg; 0.23 mmol) was reacted with TBDMS-CsA-aldehyde (300 mg; 0.23 mmol); Yield: 99.1 mg (32%), colorless solid; MS (ES) $C_{70}H_{117}N_{13}O_{14}$ calculated 1364. found 1365 (M+H)$^+$.

Example 25

Synthesis of Compound 26

Step 1:

To 3,4-diaminobenzoic acid (300 mg; 1.97 mmol) concentrated sulfuric acid (2 ml) was added, followed by 2-(dimethylamino)ethanol (176 mg; 1.97 mmol). The mixture was stirred for 1 hour at room temperature, subsequently placed on ice and brought to pH 14 with a 20% sodium hydroxide solution. Then, it was extracted with ethyl acetate, the organic phase was dried over $MgSO_4$, evaporated to dryness and the remainder containing 2-(dimethylamino)ethyl-3,4-diaminobenzoate (154 mg; 35%) was used without further purification in the next step.

Step 2:

The compound 26 was prepared in the same manner as compound 5 (method B) starting from TBDMS-CsA-aldehyde (300 mg; 0.23 mmol) and 2-(dimethylamino)ethyl-3, 4-diaminobenzoate (52 mg; 0.23 mmol). Yield: 4.3 mg (1.3%), colorless solid; MS (ES) $C_{71}H_{120}N_{14}O_{14}$ calculated 1393. found 1394 (M+H)$^+$.

Example 26

Synthesis of Compound 27

Step 1:

2-(Morpholin-4-yl)ethyl 3,4-diaminobenzoate was prepared as described in step 1 of the example 25 starting from 3,4-diaminobenzoic acid (300 mg; 1.97 mmol) and 2-(morpholin-4-yl)ethanol (258 mg; 1.97 mmol). Yield: 61 mg (12%).

Step 2:

The compound 27 was prepared in the same manner as compound 5 (method B) starting from TBDMS-CsA-aldehyde (300 mg; 0.23 mmol) and 2-(morpholin-4-yl)ethyl-3, 4-diaminobenzoic acid (61 mg; 0.23 mmol). Yield: 8.5 mg (2.6%), colorless solid; MS (ES) $C_{73}H_{122}N_{14}O_{15}$ calculated 1435. found 1436 (M+H)$^+$.

Example 27

Synthesis of Compound 28

Compound 28 was prepared as compound 5 (method B), with the difference that the following substances in the following amounts were used: TBDMS-CsA-aldehyde (300 mg; 0.23 mmol) and 2,3-diaminobenzoic acid (35 mg; 0.23 mmol); Yield: 65 mg (21%), colorless solid; MS (ES) $C_{67}H_{111}N_{13}O_{14}$ calculated 1322. found 1323 (M+H)$^+$.

Example 28

Synthesis of Compound 29

Compound 29 was prepared as compound 5 (method B), with the difference that the following substances in the following amounts were used: TBDMS-CsA-aldehyde (300 mg; 0.23 mmol) and methyl 2,3-diaminobenzoate (38 mg; 0.23 mmol); Yield: 50.8 mg (17%), colorless solid; MS (ES) $C_{68}H_{113}N_{13}O_{14}$ calculated 1336. found 1337 (M+H)$^+$.

Example 29

Synthesis of Compound 30

Dimethyl 3,4-diaminophthalate was prepared following a literature procedure (J. Heterocyclic Chem. 10 (1973), 891-898) and the ester (30 mg; 0.13 mmol) was reacted with TBDMS-CsA-aldehyde (175 mg; 0.13 mmol) in the same manner as described for compound 5 (method B). Yield: 38.6 mg (21%), colorless solid; MS (ES) $C_{70}H_{115}N_{13}O_{16}$ calculated 1394. found 1395 (M+H)$^+$.

Example 30

Synthesis of Compound 31

Step 1:

An ethanolic solution of Na-ethanolate, prepared from sodium (181 mg, 7.87 mmol) in ethanol (5 ml), was added to a suspension of dimethyl 3,4-diaminophthalate (820 mg; 3.66 mmol) in ethanol (3.5 ml) and water (0.15 ml) and the mixture was heated at reflux during two hours. After cooling, the solid was filtered, dissolved in water (7 ml) and the solution was neutralized with 1M HCl. Then, it was lyophilized and the remainder was stirred with methanol (50 ml). After renewed filtration, the filtrate was concentrated in vacuum and the 4,5-diaminophthalic acid was obtained from the remainder after RP-HPLC (column C18; gradient H$_2$O/MeOH 95:5) and lyophilization. Yield: 553 mg (77%).

Step 2:

The compound 31 was prepared in the same manner as compound 5 (method B) starting from TBDMS-CsA-aldehyde (300 mg; 0.23 mmol) and 4,5-diaminophthalic acid (45 mg; 0.23 mmol). Yield: 16.5 mg (5.3%), colorless solid; MS (ES) $C_{68}H_{111}N_{13}O_{16}$ calculated 1366. found 1367 (M+H)$^+$.

Example 31

Synthesis of Compound 32

Dimethyl 3,4-diaminophthalate was prepared following a literature procedures (J. Heterocyclic Chem. 10 (1973), 891-898) and the ester (51 mg; 0.23 mmol) was reacted with TBDMS-CsA-aldehyde (300 mg; 0.23 mmol) in the same manner as described for compound 5 (method B). Yield: 63.9 mg (20%), colorless solid; MS (ES) $C_{70}H_{115}N_{13}O_{16}$ calculated 1394. found 1395 (M+H)$^+$.

Example 32

Synthesis of Compound 33

5-(3,4-Diaminophenyl)tetrazol dihydrochloride was prepared following a literature procedure (EP1944311) and the tetrazole (57 mg; 0.23 mmol) was reacted with TBDMS-CsA-aldehyde (300 mg; 0.23 mmol) in the same manner as described for compound 5 (method B). Yield: 32.9 mg (11%), colorless solid; MS (ES) $C_{67}H_{111}N_{17}O_{12}$ calculated 1346. found 1346 (M+).

Example 33

Synthesis of Compound 34

Compound 34 was prepared as compound 5 (method B), with the difference that the following substances in the following amounts were used: TBDMS-CsA-aldehyde (174 mg; 0.13 mmol) and 3,4-diaminobenzenesulfonic amide (25 mg; 0.13 mmol); Yield: 14.5 mg (8%), colorless solid; MS (ES) $C_{66}H_{112}N_{14}O_{14}S$ calculated 1357. found 1358 (M+H)+.

Example 34

Synthesis of Compound 35

3,4-diaminobenzamidine was prepared following a literature procedure (WO1999/24395) and the amidine (35 mg; 0.23 mmol) was reacted with TBDMS-CsA-aldehyde (300 mg; 0.23 mmol) in the same way as described for compound 5 (method B). Yield: 86.9 mg (29%), colorless solid; MS (ES) $C_{67}H_{113}N_{15}O_{12}$ calculated 1320. found 1321 (M+H)+.

Example 35

Synthesis of Compound 36

3-Amino-4-(methylamino)benzoic acid was prepared following a literature procedure (WO2005/030704) and the diamine (39 mg; 0.23 mmol) was reacted with TBDMS-CsA-aldehyde (300 mg; 0.23 mmol) in the same manner as described for compound 5 (method B). Yield: 87.7 mg (29%), colorless solid; MS (ES) $C_{68}H_{113}N_{13}O_{14}$ calculated 1336. found 1337 (M+H)+.

Example 36

Synthesis of Compound 37

4-Amino-3-(methylamino)benzoic acid was prepared following a literature procedure (WO2000/020400) and the diamine (39 mg; 0.23 mmol) was reacted with TBDMS-CsA-aldehyde (300 mg; 0.23 mmol) in the same manner as described for compound 5 (method B). Yield: 80.2 mg (26%), colorless solid; MS (ES) $C_{68}H_{113}N_{13}O_{14}$ calculated 1336. found 1337 (M+H)+.

Example 37

Synthesis of Compound 38

N-(3,4-Diaminophenyl)trifluoroacetamide was prepared following a literature procedure (WO2004/039318) and the diamine (51 mg; 0.23 mmol) was reacted with TBDMS-CsA-aldehyde (300 mg; 0.23 mmol) in the same manner as described for compound 5 (method B). Yield: 23.7 mg (7.4%), colorless solid;
MS (ES) $C_{68}H_{111}F_3N_{14}O_{13}$ calculated 1389. found 1390 (M+H)+.

Example 38

Synthesis of Compound 39

Compound 39 was prepared in the same manner as described in example 17, with the difference that 3,3'-diaminobenzidin tetrahydrochloride dihydrate (18.3 mg; 46 µmol) was used as a diamine. Yield: 4.5 mg (40.6%).

Example 39

Synthesis of Compound 40

Compound 40 was prepared in the same manner as described in example 17, with the difference that 1,2,4,5-tetraaminobenzene tetrahydrochloride (5.4 mg; 19 µmol) was used as diamine. Yield: 4.3 mg (41.1%).

Example 40

Synthesis of Compound 41

Compound 41 was prepared in the same manner as described in example 17 with the difference that 4-(4-methylpiperazin-1-yl)-1,2-diaminobenzene (4.1 mg; 20 µmol) was used as diamine. Yield: 2.3 mg (20.9%).

Example 41

Synthesis of Compound 42

A solution of acetyl-CsA-aldehyde (25 mg; 20 µmol) und ethylendiamine (1.5 µl) in dichloromethane (5 ml) was stirred for 1 h at room temperature, and then for 20 minutes at 5° C. N-bromosuccinimide (4 mg) was added subsequently and the solution was stirred overnight. The solvent was removed in vacuo and the remainder was taken in ethyl acetate (30 ml). Then, it was subsequently washed with saturated $NaHCO_3$— (2×10 ml), 5% $KHSO_4$— (2×10 ml) and saturated sodium chloride-solution (2×10 ml). After drying over $MgSO_4$, the solvent was removed in vacuo and subsequently, the remainder was taken in a solution of 0.1 M NaOH (4 ml) in the same volume of tetrahydrofuran. It was stirred for 2-5 hours till completion of the reaction (control by analytical HPLC). The product was separated by preparative HPLC. Yield: 7 mg (28%).

Example 42

Synthesis of Compound 43

Acetyl-CsA-carboxylic acid (50 mg; 0.04 mmol), L-serine methylester hydrochloride (7 mg) and (benzotriazol-1-yl)oxytripyrrolidinophosphonium hexafluorphosphate (PyBOP) (23 mg; 0.044 mmol) were dissolved in DMF (3 ml) and subsequently treated with DIPEA (21 µl). After stirring for 50 min at room temperature, the intermediate product was separated by preparative HPLC. Yield: 27 mg (50%).

27 mg of amide-intermediate product were dissolved in toluene (20 ml) and then triethylamine (20 µl) and methansulfonyl chloride (10 µl) were added. After removal of solvents in vacuo, the residue was treated with 0.2 M NaOH (2 ml) and THF (2 ml) and the mixture was stirred till completion of the reaction (control by analytical HPLC). The final product was isolated by preparative HPLC. Yield: 7 mg (27%).

Example 43

Synthesis of Compound 44

Compound 44 was prepared in the same manner as described in example 17 with the difference that (R,R)-(−)-trans-1,2-diaminocyclohexane hydrochloride (3.3 mg; 22 µmol) was used as diamine. Yield: 5.8 mg (56.4%).

Example 44

Synthesis of Compound 45

A mixture of acetyl-CsA-aldehyde (11 mg; 8.8 µmol) and 5,6-diamino-naphthalen-1-sulfonic acid (2.8 mg; 12 µmol) in DMF (1 ml) was shacked at room temperature overnight. The solvent was removed in vacuo and MeOH (1 ml) and 0.2 M NaOH (1 ml) were added to the remainder. The reaction mixture was shacked at 5° C. overnight and the product was purified by preparative HPLC. Yield: 8.0 mg (71.0%).

Example 45

Synthesis of Compound 46

N-(3,4-diaminophenyl)guanidine hydrochloride was prepared following a literature procedure (WO1998/045275) and the diamine (62 mg; 0.307 mmol) was reacted with TBDMS-CsA-aldehyde (400 mg; 0.307 mmol) in the same manner as described for compound 5 (method B). Yield: 121.7 mg (30%), colorless solid; MS (ES) $C_{67}H_{114}N_{16}O_{12}$ calculated 1335. found 1336 (M+H)$^+$.

Example 46

Synthesis of Compound 47

Step 1:
A solution of 2,4-diaminonitrobenzene (8 g; 52.2 mmol) and DIPEA (9.9 g; 76.6 mmol) in DCM (300 ml) was cooled to 0° C. and at this temperature trifluoromethanesulfonic anhydride (23 g; 81.5 mmol) was added dropwise within 90 min. Then, it was stirred overnight, diluted with DCM, washed with saturated $NaHCO_3$ solution, dried over $MgSO_4$ and evaporated in vacuo. The remainder was stirred with ether (3×400 ml). The combined supernatants were combined and N-(4-amino-3-nitrophenyl)trifluormethansulfonamide was obtained after chromatography purification on silica gel by elution with DCM; Yield: 12.2 g (82%).

Step 2:
To a solution of the above nitro compound (12.2 g; 42.8 mmol) in MeOH (150 ml) was added 10% Pd—C (1.2 g). The mixture was stirred at room temperature under $H_2$ atmosphere overnight, the solid was filtered and was with MeOH. In vacuo concentration, chromatography on silica gel (gradient: DCM/MeOH) gave N-(3,4-diaminophenyl)-trifluormethansulfonamide. Yield: 3.87 g (35%).

Step 3:
Compound 47 was obtained in the same manner as described for compound 5 (method B) starting from N-(3,4-diaminophenyl)-trifluormethansulfonamide (40 mg; 0.157 mmol) and TBDMS-CsA-aldehyde (205 mg; 0.157 mmol). Yield: 14 mg (6.3%), reddish solid; MS (ES) $C_{67}H_{111}F_3N_{14}O_{14}S$ calculated 1425. found 1426 (M+H)$^+$.

Example 47

Synthesis of Compound 48

Step 1:
A solution of 1,2-diamino-3-fluorobenzene (100 mg; 0.8 mmol) in 100% sulfuric acid (5 ml) was heated by microwave at 150° C. for 30 min and the progress of the reaction was followed by HPLC. Then, the solution was stirred in 200 g ice and neutralized with 40% NaOH solution. The lyophilized remainder was suspended in acetonitrile (100 ml). After filtration and subsequent removal of the solvent, the 3,4-diamino-5-fluoro-benzensulfonic acid was dissolved in water (5 ml) and purified over a Dowex Cl$^-$. Yield: 148 mg (90%).

Step 2:
A solution of Ac-CsA-aldehyde (compound 1; 12 mg; ~10 µmol) in DMF (3 ml) was added to 3,4-diamino-5-fluoro-benzensulfonic acid (3.6 mg; 17.5 µmol) in DMF (1 ml). After addition of a solution of potassium monopersulfate (6.1 mg; ~10 µmol) in water (0.1 ml), the mixture was stirred. The reaction was completed after 3 hours and the remainder was purified by preparative HPLC. Yield: 7 mg (49%).

MeOH (1 ml) and ice-cold 0.2M NaOH (1 ml) were added to the purified fraction and the mixture was shacked at 5° C. overnight. Then, it was acidified and the remainder was purified over preparative HPLC. Yield: 4.9 mg (72%).

Example 48

Synthesis of Compound 49

Step 1: Synthesis of hexapeptide H-(L-Pro)$_6$-OH

The hexapeptide H-(L-Pro)$_6$-OH was prepared on a 2-chloro-tritylchloride resin by standard Fmoc solid-phase peptide synthesis protocol. In every synthetic cycle, Fmoc protected L-proline was activated with PyBOP and DIPEA in DMF and coupled for 2 h. The Fmoc-protecting group was cleaved with a 20% solution of piperidine in DMF by stirring the amine one time for 5 min and another time for 15 min. After the last coupling, the peptide was cleaved from the resin with 100% TFA and purified by preparative HPLC.

Step 2:
DIPEA (5 µl; 29 µmol) was added to a solution of compound 5 (10 mg; 7.6 µmol) and HATU (3.3 mg; 8.7 µmol) in NMP (1 ml). The mixture was shacked for 5 min and subsequently treated with H-(L-Pro)$_6$-OH (10 mg; 16 µmol). After shaking the mixture for 2 h, the product was purified by preparative HPLC. Yield: 8.7 mg (60%).

Example 49

Synthesis of Compound 50

Step 1: Synthesis of hexapeptide H-(L-Ala)$_6$-OH The hexapeptide was synthesized starting from Fmoc-protected L-alanine analogously to the preparation protocol of H-(L-Pro)$_6$-OH as described at step 1 of the example 48.

Step 2:
Compound 50 was obtained starting from compound 5 (10 mg; 7.6 µmol) and H-(L-Ala)$_6$-OH (10 mg; 23 µmol) in the same way as described at example 48 (step 2). Yield: 8.1 mg (61%).

Example 50

Synthesis of Compound 51

Step 1: Synthesis of hexapeptide H-(β-Ala)$_6$-OH The hexapeptide was synthesized starting from Fmoc-protected β-alanine analogously to the preparation protocol of H-(L-Pro)$_6$-OH as described at step 1 of the example 48.

Step 2:

Compound 51 was obtained starting from compound 5 (10 mg; 7.6 µmol) and H-(β-Ala)$_6$-OH (10 mg; 23 µmol) in the same way as described at example 48 (step 2). Yield: 4.2 mg (32%).

Example 51

Synthesis of Compound 52

DIPEA (5 µl; 29 µmol) was added to a solution of compound 5 (10 mg; 7.6 µmol) and HATU (3.3 mg; 8.7 µmol) in NMP (1 ml) and the mixture was shacked for 5 min. After addition of 2-(N,N-dimethylamino)ethylamine (2.3 µl; 21 µmol), the mixture was shacked for additional 2 h and the product was then purified by preparative HPLC. Yield: 7.9 mg (75%).

Example 52

Synthesis of Compound 53

Compound 53 was obtained starting from compound 5 (10 mg; 7.6 µmol) and 4-(2-aminoethyl)morpholine (2.1 µl; 16 µmol) according to the method described in example 51. Yield: 9.0 mg (83%).

Example 53

Synthesis of Compound 54

Step 1: N-(2-(piperazin-1-yl)ethyl)-tritylamine

A solution of 1-(2-aminoethyl)-piperazine (100 µl; 0.76 mmol) and triethylamine (106 µl; 0.76 mmol) in DCM (20 ml) was cooled at 5° C. and treated with trityl chloride. The mixture was stirred at 20° C. overnight and after solvent removal, the product was purified by preparative HPLC. Yield: 84 mg (30%).

Step 2:
4-[4-(2-Aminoethyl)piperazin-1-yl]-4-oxo-butanoic acid

To a solution of N-(2-(piperazin-1-yl)ethyl)-tritylamine (55 mg; 0.15 mmol) in DMF (2 ml) were added succinic anhydride (30 mg; 0.30 mmol) and DIPEA (51 µl; 0.3 mmol). The mixture was stirred for 2 h and the product 4-oxo-4-{4-[2-(trityl-amino)ethyl]piperazin-1-yl}-butanoic acid was purified by preparative HPLC. After lyophilization, TFA (2 ml) was added to this product and the mixture was stirred for 30 min. The TFA was in vacuo distilled and the remainder was purified by preparative HPLC. Yield: 25 mg (36%).

Step 3

A solution of compound 5 (10 mg; 7.6 µmol), HATU (8 mg; 8.7 µmol) and DIPEA (10 µl; 29 µmol) in NMP (1 ml) was shacked for 5 min. After addition of 4-[4-(2-aminoethyl)piperazin-1-yl]-4-oxo-butanoic acid (24 mg; 106 µmol), the mixture was shacked for additional 2 h. The product was purified by preparative HPLC. Yield: 18 mg (67%).

Example 54

Synthesis of Compound 55

3-Amino-2-(methylamino)benzoic acid was prepared following a literature procedure (WO2008/008431) and the acid (38 mg; 0.23 mmol) was reacted with TBDMS-CsA-aldehyde (300 mg; 0.23 mmol) in the same manner as described for compound 5 (method B). Yield: 60.3 mg (20%), colorless solid; MS (ES) $C_{68}H_{113}N_{13}O_{14}$ calculated 1336. found 1337 (M+H)$^+$.

Example 55

Synthesis of Compound 56

Step 1:

3-(N-Acetyl-N-methyl-amino)-2-nitrobenzoic acid was prepared following a literature procedure (WO1998/24771) and the acid (5.35 g; 22.46 mmol) was heated together 6N HCl (46 ml) at 120° C. in a bomb tube for 90 min. After distilling off the solvent, dilution with MeOH, absorption on diatomaceous earth, and chromatography on silica gel (CHCl$_3$/MeOH 19:1+0.5% HOAc), 3.4 (77%) 3-(methylamino)-2-nitrobenzoic acid was obtained.

Step 2:

A solution of the above described nitro compound (3.35 g; 17.1 mmol) and hydrazine hydrate (2.5 ml; 51.2 mmol) in dry MeOH (100 ml) was carefully mixed portionwise with a suspension of Ni-Raney (3.4 g) in the same solvent. The mixture was stirred for 30 min at 50° C., concentrated, and the remainder was filtered over silica with MeOH to give 1.24 g (44%) 2-amino-3-(methylamino)benzoic acid as a dark solid.

Step 3:

The benzoic acid of the above step (32 mg; 0.19 mmol) was reacted with TBDMS-CsA-aldehyde (250 mg; 0.19 mmol) in the same manner as described for compound 5 (method B). Yield: 89 mg (35%), brown solid; MS (ES) $C_{68}H_{113}N_{13}O_{14}$ calculated 1336. found 1337 (M+H)$^+$.

Example 56

Synthesis of Compound 57

The dipeptide H-L-Glu(OCH$_2$Ph)-L-Glu(OCH$_2$Ph)-NH$_2$ was bound to the Rink amide resin using standard fluorenylmethoxycarbonyl(Fmoc)-peptide-synthesis (activation of Fmoc-L-Glu(OCH$_2$Ph)-OH with PyBOP/DIPEA and cleavage of the Fmoc-group with 2% DBU in DMF and 2% piperidine in DMF). A solution of compound 5 (16 mg; 0.012 mmol), HATU (7 mg; 0.18 mmol) and DIPEA (6 µl) in DMF (2 ml) was added to the resin. After overnight shacking, the product of the reaction was cleaved from the resin by treatment during 1 h at room temperature with TFA/DCM 1:1 (2 ml). After filtration and dilution with toluene (2×2 ml) the solvent was removed under vacuum. The final product was separated from the remainder by preparative HPLC. Yield: 6 mg (28%).

Example 57

Synthesis of Compound 58

Compound 58 was obtained following the method described in example 56 starting from Fmoc-L-Leu-OH, Fmoc-L-Arg(Pbf)-OH, compound 5 (35 mg; 0.0265 mmol), HATU (11 mg; 0.029 mmol) and DIPEA (9 µl). After washing the resin with DMF and DCM, compound 58 was cleaved with TFA and isolated from the remainder by preparative HPLC. Yield: 2 mg (5%).

Example 58

Synthesis of Compound 59

Compound 59 was obtained in the same manner as described at example 57 starting from Fmoc-L-Pro-OH, Fmoc-L-Asn(Trt)-OH and compound 5 (35 mg; 0.0265 mmol). Yield: 28 mg (69%).

Example 59

Synthesis of Compound 60

Compound 60 was obtained in the same manner as described at example 57 starting from Fmoc-L-Cys(Trt)-OH, Fmoc-L-Ala-OH and compound 5 (35 mg; 0.0265 mmol). The cleavage of the final compound from the resin was carried out with DTT (100 mg) containing TFA (3 ml). Yield: 12 mg (30%).

Example 60

Synthesis of Compound 61

Compound 61 was obtained in the same manner as described at example 59 starting from Fmoc-L-Cys(Trt)-OH and compound 5 (35 mg; 0.0265 mmol). Yield: 4.4 mg (11%).

Example 61

Synthesis of Compound 62

Compound 62 was obtained in the same manner as described at example 57 starting from Fmoc-L-Ser(t-Bu)-OH, Fmoc-L-Glu(Ot-Bu)-OH and compound 5 (35 mg; 0.0265 mmol). Yield: 11.6 mg (28%).

Example 62

Synthesis of Compound 63

Compound 63 was obtained in the same manner as described at example 57 starting from Fmoc-L-Glu(Ot-Bu)-OH and compound 5 (35 mg; 0.0265 mmol). Yield: 13 mg (31%).

Example 63

Synthesis of Compound 64

To a solution of compound 5 (10 mg; 7.6 µmol) in NMP (1 ml) were added HATU (3.3 mg; 8.7 µmol) and DIPEA (5 µl). After stirring of the mixture for 2 min, 1-(2-aminoethyl)-piperazine (1.2 mg; 9.4 µmol) was added and the mixture was shacked for 3 hours. Compound 64 was separated by preparative HPLC. Yield: 3.7 mg (34%).

Example 64

Synthesis of Compound 65

DIC (2 µl) and DMAP (1.4 mg; 11.4 µmol) were added to a solution of compound 5 (10 mg; 7.6 µmol) in DCM (1 ml). After stirring for 30 minutes, the solvent was removed in vacuo. The remainder was treated with a solution of salicylic acid (2 mg; 14.5 µmol) in NMP (1 ml), the mixture was shacked overnight and then compound 65 was isolated by preparative HPLC. Yield: 1.5 mg (13%).

Example 65

Synthesis of Compound 66

Step 1:
N-(Trityl)-2-(2-(2-aminoethoxy)ethoxy)ethylamine was prepared following a literature procedure (Eur. J. Org. Chem. 2009, 3953-3963).

Step 2:
Compound 5 (50 mg; 0.038 mmol) and PyBOP (19.7 mg; 0.038 mmol) were dissolved in NMP (3 ml); DIPEA (19.3 µl) and the amine of step 1 (17.7 mg; 0.045 mmol) were added. The reaction mixture was stirred for 1 hour, diluted with ethyl acetate (50 ml) and subsequently washed for two times with 5% $KHSO_4$—, 5% $NaHCO_3$— and saturated sodium chloride-solution. The organic layer was dried over $MgSO_4$, concentrated in vacuo and reacted with TFA (2 ml). After 15 minutes at room temperature, the reaction mixture was concentrated and compound 66 was isolated by preparative HPLC. Yield: 29 mg (52%).

Example 66

Synthesis of Compound 67

DIPEA (10 µl) was added to a solution of cis,cis-1,3,5-cyclohexane tricarboxylic acid (22 mg; 0.1 mmol), compound 66 (7.3 mg; 0.005 mmol) and PyBOP (3 mg; 0.0058 mmol) in NMP (1 ml). The mixture was stirred for 2 hours at room temperature and compound 67 was isolated by preparative HPLC. Yield: 5 mg (61%).

Example 67

Synthesis of Compound 68

DIPEA (10 µl) was added to a solution of succinic anhydride (20 mg; 0.2 mmol) and compound 66 (7.3 mg; 0.005 mmol) in NMP (1 ml) and the mixture was stirred overnight at room temperature. Compound 68 was then isolated by preparative HPLC. Yield: 2.9 mg (37%).

Example 68

Preparation of Compound 69 by Derivatization of Compound 5 with a Molecule of Dye a) Synthesis of TAMRA-EDO (tracer):
A solution of 5(6)-carboxytetramethylrhodamine (20 mg; 46.5 µmol) in DMF (5 ml) was treated with 2-(7-aza-1H-benzotriazole-1-yl)-1,1,3,3-tetramethyluronium hexafluorophosphate (HATU) (19 mg; 8.3 µmol) and stirred for 5 minutes for pre-activation. To this solution 2,2-(ethylenedioxy)ethyldiamine (68 μl; 465 μmol) was then added. After 2 h of stirring, the product was isolated by preparative HPLC. Yield: 15 mg (57.6%).

b) Synthesis of compound 69:

Compound 5 (10 mg; 7.56 μmol) was dissolved in DMF (1 ml) and after addition of HATU (3.2 mg; 8.3 μmol) and DIPEA (3.9 μl; 22.68 μmol) was stirred for 5 minutes for pre-activation. Then, the solution of TAMRA-EDO (8.5 mg; 15.12 μmol) dissolved in DMF (1 ml) was added. After 2 h of stirring, the product (compound 69) was isolated by preparative HPLC. Yield: 7 mg (50%).

Example 69

Inhibition of the peptidyl-prolyl-cis/trans-isomerase (PPIase) activity of the cyclophilin Cyp18wt The determination was performed on a UV/Vis spectrometer at 10° C. cuvette temperature, whereby the device is operated at 390 nm in kinetic-mode (measurement buffer: 35 mM HEPES/NaOH pH 7.8 (AppliChem A1069)). 0.58 nM recombinant human wild type Cyp18 (Cyp18 wt), 2.33 nM bovine serum albumin (BSA) and 1 mg/ml chymotrypsin (Merck) solved in 35 mM HEPES/NaOH pH 7.8 as well as different concentration of each test substance, where appropriate, were in the cuvette. The reaction was started with a stock solution of Suc-Ala-Ala-Pro-Phe-4-nitroanilide (Bachem, 10 mg/ml DMSO) as substrate so that a final substrate concentration of 32 μM resulted. The extinction-time-curves were evaluated after expiry of the fast phase of the reaction i.e. after approximately 60 seconds according to a rate equation of a first-order reaction. $IC_{50}$ values of the inhibitors result from the first order rate constant of the non-inhibited reaction in ratio to the inhibited reaction (% inhibition) measured in function of the inhibitor concentration in the cuvette. The resulting $IC_{50}$ values of the test compounds are listed in table 1.

Example 70

Inhibition of the Phosphatase Activity of Calcineurin

The determination of the dephosporylating calcineurin activity in presence and absence of inhibitors was carried out in a scintillation-proximity-assay (see also R. Baumgrass, et al.; J. Biol. Chem. 276 (2001), 47914-47921). The measurement was carried out by incubation of 10 μMol of the biotinylated phosphopeptide Asp-Leu-Asp-Val-Pro-Ile-Pro-Gly-Arg-Phe-Asp-Arg-Arg-Val-pSer-Val-Ala-Ala-Glu (MW=2192.0) (RII-peptide) marked with $^{33}P$ in a sample buffer (40 mM Tris-HCl, pH 7.5, 100 mM NaCl, 6 mM $MgCl_2$, 0.5 mM dithiothreitol, 1 mM. $CaCl_2$, 0.1 mg/ml bovine serum albumin) in presence of 50 nM calmodulin and 1.32 nM calcineurin at 30° C. for 20 min in a 96 well micro titer plate (Costar, Bodenheim, Germany). The total volume of the assay/well was 100 μl. After this reaction time a 90 μl aliquot of the reaction mixture was transferred into a scintillation cavity coated with streptavidin and incubated for 20 min at 22° C. After a washing step the RII phosphopeptide-associated $^{33}P$ radioactivity was measured in a MicroBeta Top Counter (Wallac) and the enzyme activity was indicated as average value of three measurements±S.D. The uninhibited dephosphorylation activity has been set on 100%. The calcineurin-inhibition of potential cyclophilin-inhibitor-complexes has been measured in presence of 10 nM to 50 μM Cyp18 concentrations with constant inhibitor concentration of 10-50 μM (typical stock solution 1 mM in DMSO). The results for the test compounds are listed in Table 1.

Example 71

Verification of the Immunosuppressive Effect in the Cellular NFAT-Reporter-Gene Assay An antigen specific stimulation of the T-cell receptor causes the activation of transcription factors such as e.g. NFAT (nuclear factor of activated T cells). NFAT-activation is essential for the expression of interleukine-2 and therefore, for the proliferation of T-cells as part of the immune response. A stable NFAT-reporter-gene cell line enables the analysis of modulators of the NFAT-pathways and thus, the evaluation of the immunosuppressive effects of compounds.

The stably transfected reporter-gene cell line GloResponse NFAT-RE-luc2P HEK293 (promega Corp. USA) was cultivated in DMEM (10% FCS; 2 mM Glutamin; 200 μg/ml Hygromycin) and seeded on 96-well plates (200.000 cells/well). The compounds to be tested were either added to the cells in a 2-point-determination (5 μM and 10 μM) or an $IC_{50}$-determination (concentration series 4.1 nM-1 μM). Unmodified cyclosporin A has been used as immunosuppressive reference compound. Immediately thereafter the cells were stimulated with 5 nM PMA and 2 μM ionomycin and incubated over 16 h (37° C.; cell incubator). This double stimulation simulates a T-cell receptor stimulation and causes a NFAT activation with subsequently expression of the luciferase-reporter-gene. The amount of luciferase was quantitatively determined after 16 h by measurement of the bioluminescence by Bright-Glo Luciferase-Assay-System (Promega Corp., USA). The averaged luciferase values of the vehicle treated (1% DMSO) and with PMA/ionomycin stimulated cells were used as positive control and reference value. The results for the test compounds are listed in Table 1.

In the following table 1 the compounds 4-68 according to the invention in comparison to cyclosporin A are listed in regard to their activity for inhibition of Cyp18 and calcineurin as well as their activity in the NFAT-reporter-gene assay:

TABLE 1

| Compound | Inhibition of Cyp18wt $IC_{50}$ [nM] | Indirect Inhibition of Calcineurin $IC_{50}$ [nM] | NFAT-reporter-gene assay $IC_{50}$ [nM] |
| --- | --- | --- | --- |
| Cyclosporin A | ~8 | 85 | 31.4 |
| 4 | 264 | >10000 | |
| 5 | 9.6 | >10000 | >10000 |
| 6 | 700 | | |
| 7 | 11.9 | 6900 | >10000 |
| 8 | 90.4 | | |
| 9 | 13.9 | 7000 | >10000 |
| 10 | 11.5 | 6900 | >10000 |
| 11 | 13.0 | 4700 | 10000 |
| 12 | 31.4 | | 2000 |
| 13 | 11.1 | >10000 | >10000 |
| 14 | 36.4 | 3200 | |
| 15 | 4.8 | >10000 | >10000 |
| 16 | 15.1 | 7500 | |
| 17 | >50 | >10000 | |
| 18 | 1.4 | 10000 | >10000 |
| 19 | 5.4 | 7000 | >10000 |
| 20 | 6.7 | >10000 | >10000 |
| 21 | 22.2 | >10000 | 5300 |
| 22 | 8.7 | >10000 | >10000 |
| 23 | 3.8 | >10000 | >10000 |

TABLE 1-continued

| Compound | Inhibition of Cyp18wt IC$_{50}$ [nM] | Indirect Inhibition of Calcineurin IC$_{50}$ [nM] | NFAT-reporter-gene assay IC$_{50}$ [nM] |
|---|---|---|---|
| 24 | 6.2 | >10000 | >10000 |
| 25 | 22.0 | 7900 | 10000 |
| 26 | 10.8 | 6200 | >10000 |
| 27 | 5.9 | 6400 | 7400 |
| 28 | 60.0 | >10000 | >10000 |
| 29 | 29.5 | >10000 | 10000 |
| 30 | 29.1 | 10000 | >10000 |
| 31 | 39.9 | 10000 | >10000 |
| 32 | 24.9 | >10000 | >10000 |
| 33 | 9.8 | >10000 | >10000 |
| 34 | 16.4 | 6400 | >10000 |
| 35 | 12.0 | 4800 | >10000 |
| 36 | 1000 | >10000 | >10000 |
| 37 | 61.5 | >10000 | >10000 |
| 38 | 14.3 | 3340 | 3800 |
| 39 | 6.1 | >10000 | 10000 |
| 40 | 5.5 | 8000 | >10000 |
| 41 | 3.0 | >10000 | >10000 |
| 42 | 57.7 | 9500 | 10000 |
| 43 | 45.3 | 10000 | 5300 |
| 44 | 9.2 | >10000 | >10000 |
| 45 | 3.2 | >10000 | >10000 |
| 46 | 13.1 | 6630 | >10000 |
| 47 | 13.2 | >10000 | >10000 |
| 48 | 8.7 | >10000 | |
| 49 | 30.9 | >10000 | |
| 50 | 7.3 | 10000 | |
| 51 | 7.3 | >10000 | |
| 52 | 8.0 | >10000 | |
| 53 | 12.7 | 4200 | |
| 54 | 7.1 | 7200 | |
| 55 | 209.3 | >10000 | |
| 56 | >1000 | >10000 | |
| 57 | 16.9 | | |
| 60 | ~10 | | |
| 61 | ~10 | | |
| 62 | 4.4 | | |
| 63 | 5.1 | | |
| 64 | 17.2 | 10000 | |
| 65 | 20.2 | >10000 | |
| 66 | 15.0 | >10000 | |
| 67 | 8.4 | >10000 | |
| 68 | 8.5 | >10000 | |

Example 72

Determination of Cell Permeability in Jurkat Cells

Jurkat cells of the cell culture have been harvested and centrifuged. The medium has been discarded and the cells were washed once with RPM' (without phenol red, 10% FCS, Hepes, gentamicin). The cells were re-suspended in a medium adjusted to a cell concentration of $1.0 \times 10^5$-$3.0 \times 10^5$ cells/ml and subsequently incubated with a fluorescent CsA derivative (0.5 µM-2.0 µM) at 37° C., 5-10% CO$_2$ and 100% humidity. The cells were then centrifuged, the medium discarded and the cell pellet was washed once with medium and the cells were resuspended in a new medium. Subsequently, the cells were incubated for a half hour to 4 hours with the corresponding concentration (0.01 µM to 100 µM) of the test compound to be analyzed and then centrifuged again. The medium was discarded; it was once washed with 1 ml PBS and suspended in 500 µl PBS. The analysis was carried out using FACS-measurement by quantification of the replaced fluorescent CsA-derivative. The reference (without inhibitor) was thereby set 100%. The results for compound 5 and for cyclosporin A of this test system show (FIG. 1), that compound 5 is not cell permeable in comparison to CsA.

Example 73

Determination of Cell Permeability in Caco2 Cell Membranes

The test substances were diluted from a 10 mM DMSO solution to a final concentration of 5 µM in HBSS buffer pH 7.4. Subsequently, incubation takes place for 2 hours at 37° C. and 5% CO$_2$ on a differentiated mono layer of Caco2-cells, which were grown for 10 days on a Transwell-membrane. The concentration of the test substance was determined in the starting—as well as in the receiving-well. The apparent permeability ($P_{app}$) in apical to basolateral direction (A-B) and vice versa (B-A) was calculated according to the following formula: $P_{app} = 1/AC_0 \, (dQ/dt)$, wherein A is the area of the Transwell membrane, $C_0$ the substance concentration at the time point t=0 and dQ/dt represents the amount of substance migrated per time period. The results for the test compounds are listed in table 2.

Example 74

Determination of Cell Permeability in PAMPA Cell Membranes (Parallel Artificial Membrane Permeability Assay)

The test substances were diluted from a 10 mM DMSO solution to a final concentration of 500 µM in Hepes buffer pH 7.4 and transferred to a Transwell membrane, which was covered with a membrane forming solution of 10% 1,2-dioleyl-sn-glycer-3-phosphocholin and 0.5% (w/v) cholesterol in dodecane. After an incubation of 16 hours at room temperature in a liquid chamber the optical density of the solution after filtration has been measured in a range of 250 to 500 nm in steps of 10 nm each. The percentage "Flux" has been calculated from the integral of the graph between 250 and 500 nm and standardized on the optical density determined in the parallel reaction without artificial membrane. The results for the test compounds are listed in table 2.

TABLE 2

Cell permeability of selected compounds according to the present invention in comparison to cyclosporin A in Caco2- and in PAMPA cell membranes:

| Compound | Cell permeability in Caco2-cell membranes A-B [$10^{-6}$ cm/s] | Cell permeability in Caco2-cell membranes B-A [$10^{-6}$ cm/s] | Cell permeability in PAMPA-cell membranes [% flux] |
|---|---|---|---|
| Cyclosporin A | 3.0 | 7.9 | |
| 5 | 0.17 | 0.13 | 1.7 |
| 22 | 0.9 | 0.2 | 4.1 |
| 23 | 0.3 | 0.6 | |
| 28 | <0.4 | 0.3 | 3.3 |
| 31 | <0.15 | <0.18 | 0.2 |
| 33 | <0.15 | <0.15 | 0.25 |
| 34 | <0.6 | 0.87 | 19.9 |
| 35 | <0.35 | <0.46 | 4 |
| 36 | 0.3 | 0.2 | 0.7 |
| 37 | 0.1 | 0.2 | 2 |
| 46 | 0.4 | 0.2 | 13.5 |

Example 75

Verification of the Immunosuppressive Effect in the Proliferation Assay

For isolation of immune cells from the spleen of mice the strain C57BL/6 was used and obtained from CHARLES RIVER Laboratories. Before section, 14 weeks old animals were placed over 15 min in a tank flooded with $CO_2$. After one could no longer see any sign of life at the mice cervical dislocation and section with removal of the spleen took place. The isolation of the spleen cells was done at room temperature in 5 ml HBSS (PAA) by squashing the organ and plating the cells using the backside of a piston of a 1 ml syringe. Subsequently, the cells were poured through a 40 μm cell sieve and separated. The sieve was washed again with 5 ml HBSS. For the separation of the immune cells a density gradient was used, wherein 5 ml lymphocyte separation medium (Mediatech, Inc.) was layered with 5 ml of the cell suspension. Further steps were carried out according to manufacturer's instructions.

The evaluation of the inhibition of the proliferation of spleen cells by the test substances was carried out in micro titer plates (96 well plate) in triplicate. Therefore, 2 μM of the compounds to be tested or adequate controls (medium, DMSO, CsA) in RPMI-1640 medium (PAA) were incubated with $3.04 \times 10^5$ cells in 90 μl (total volume 100 μl). The activation of the proliferation was carried out by addition of 0.01 mg/ml concanavalin A (ConA) in PBS (Sigma). Subsequently, the cells were incubated at 37° C. for 72 hours. The proliferation was subsequently determined colorimetrically. Therefore, 11 μl MTT reagent (5 mg/ml, methylthiazolyl diphenyltetrazolium bromide; Sigma) were added to the cells and incubated for further 5 hours at 37° C. Subsequently, the medium was discarded, the cells were resuspended in 100 μl DMSO and the absorption was determined at 550 nm and 630 nm with a multi plate reader (VERSmax; Molecular Devices). The test results for compound 5 in comparison to cyclosporin A is exemplarily shown in FIG. 2.

Example 76

Asthma Evaluations

By application of ovalbumin together with aluminium hydroxide an immune response to ovalbumin is provoked. The immune response may be traced using the immigrated T-helper cell population (CD4+) and the immigrated eosinophilic granulocytes. Female mice (BALB/c-strain) were sensitized by intraperitoneal (i.p.) application of 50 μg ovalbumin solved in phosphate buffer (PBS) ((OVA) plus 100 μl aluminium hydroxide) with a total volume of 200 μl per mouse on day 0. 100 μg OVA in PBS (50 μl total volume) was intranasal administered to the ovalbumin sensitized mice under mild anesthesia (isoflurane) at days 7-10. These animals were divided into groups which obtained in addition either 200 μg test compound in PBS (i.p.), only PBS (diluent) or no further additive (−) at days 7, 9 and 11. At day 12 all animals were sacrificed by $CO_2$ exposition and cells of the bronchial tract were obtained by bronchial lavage (BAL) with threefold washing with 1 ml of cold PBS each using a cannula introduced into the trachea. The cells obtained by BAL were then stained twice (a) with Cy-chrome conjugated anti-mouse CD4 antibodies and (b) with FITC conjugated anti-mouse CD62L antibodies. Subsequently, the cells were analyzed by FACS. Effector/memory CD4$^+$ T-cells were differentiated as CD4$^+$/CD62L$^-$ lymphocytes and eosinophilic cells using their stray light characteristics (FSC/CCS). The results obtained with compound 5 are summarized in FIGS. 3 to 6.

FIG. 6 shows the influence of compound 5 on the number of the CD4 positive T-cells in the lung tissue, which migrated into the bronchial mucosa by the ovalbumin sensitization and can be detected there. The administration of 200 μg of compound 5 reduced very significantly the number of CD4 positive T-cells.

Figure 2:
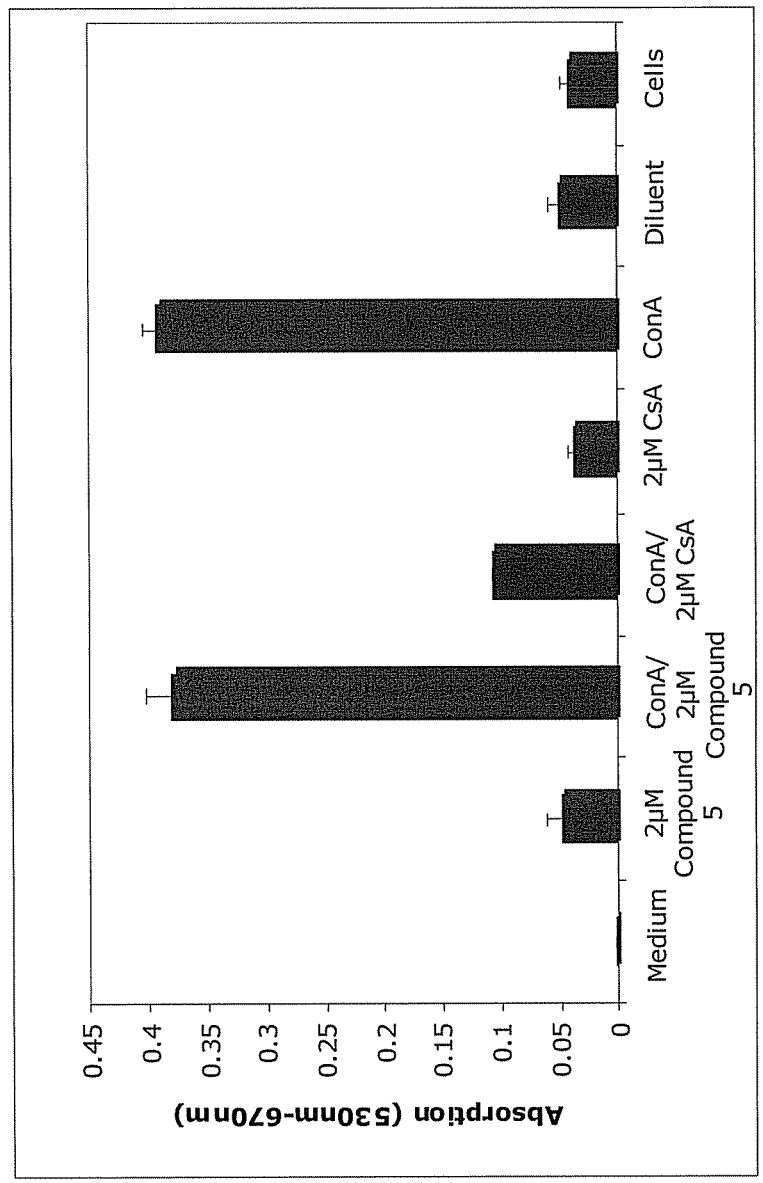
Figure 3:
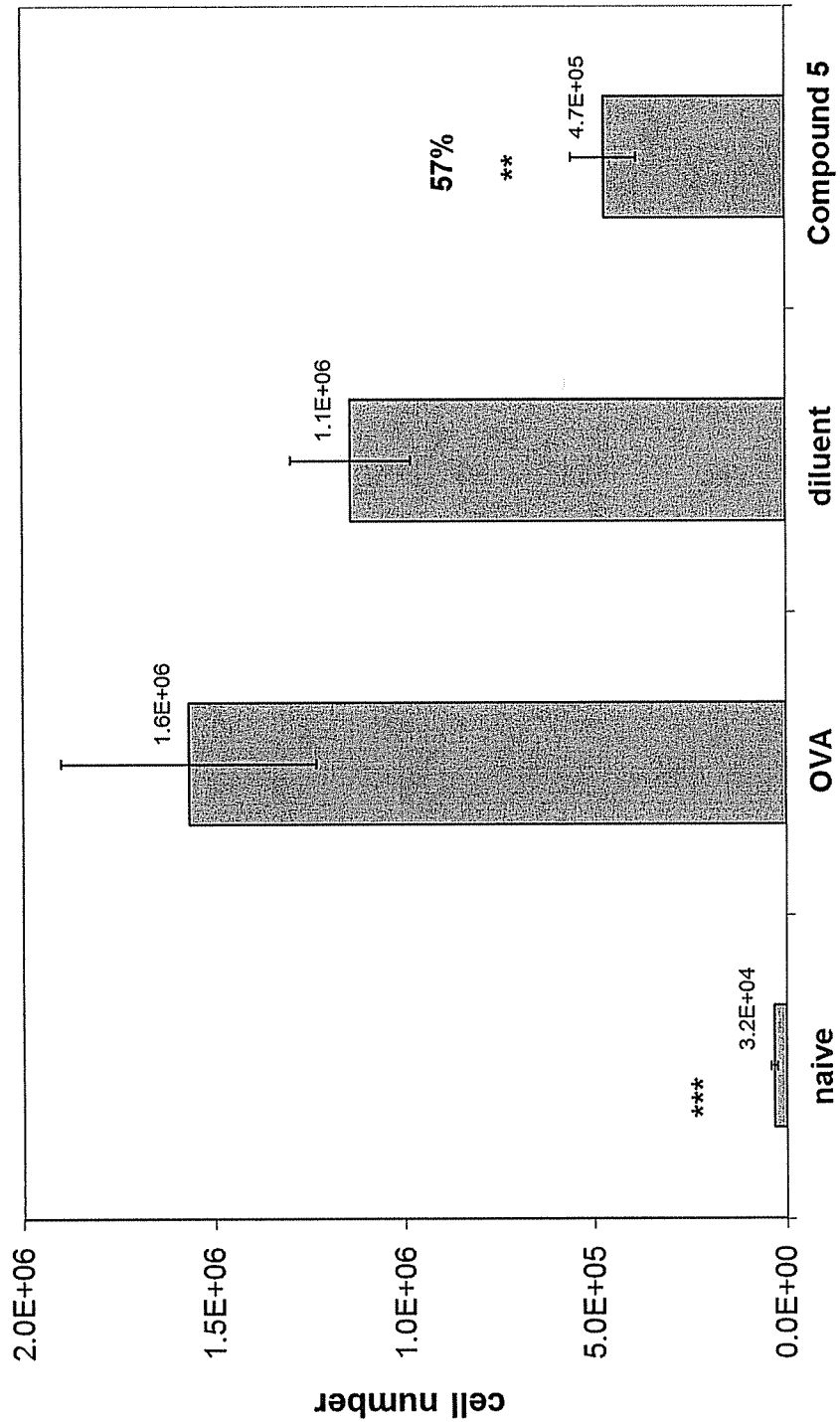
FIG. 3 shows the influence of compound 5 on the number of the eosinophilic granulocytes (eosinophils), which migrated into the bronchial mucosa by the ovalbumin sensitization and can be detected in the lung rinsing solution (lavage). The administration of compound 5 reduced very significantly the number of eosinophilic granulocytes.
Figure 4:
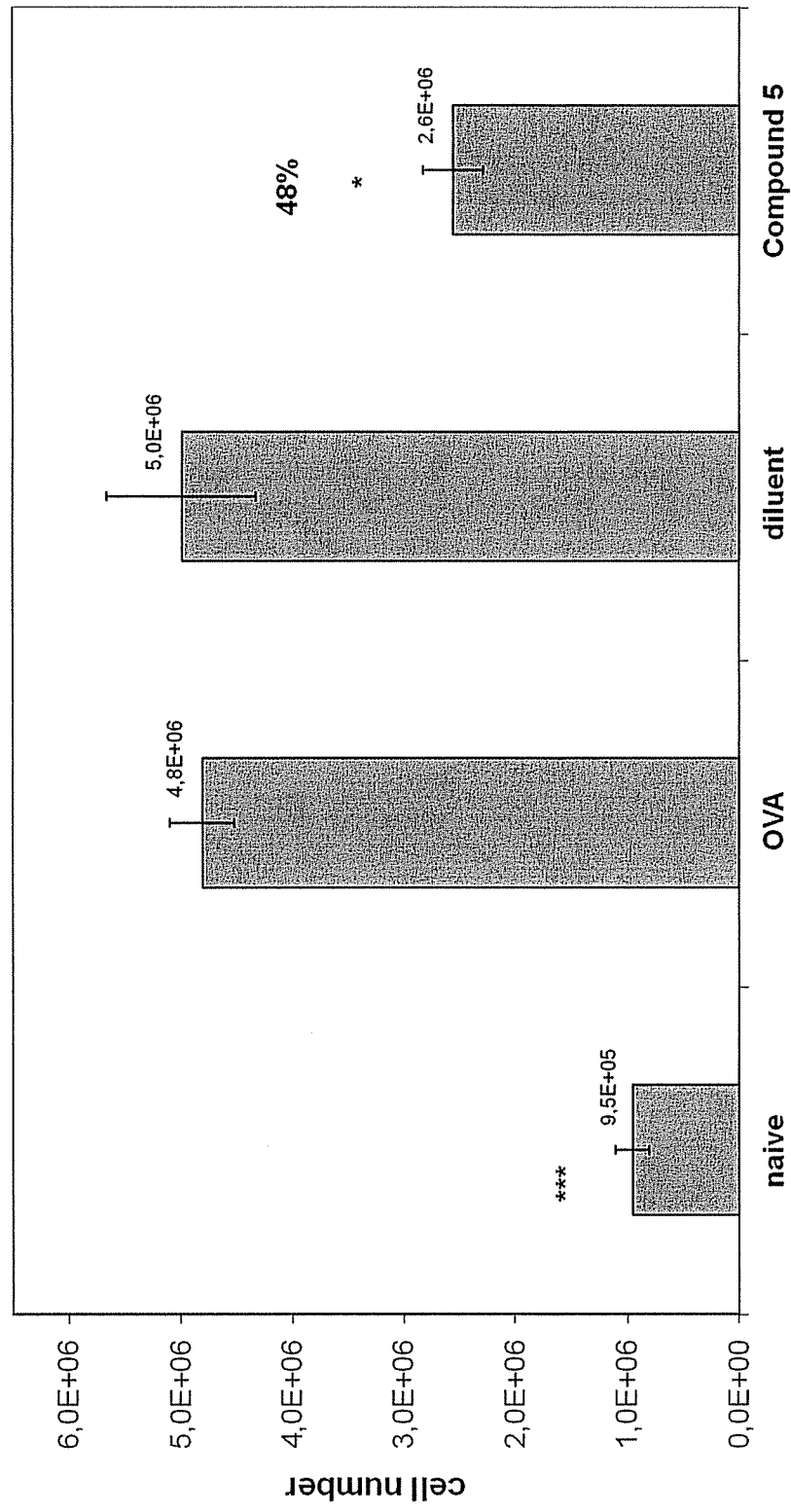
FIG. 4 shows the influence of compound 5 on the number of the eosinophilic granulocytes (eosinophils) in lung tissue, which migrated into the bronchial mucosa by the ovalbumin sensitization. The administration of 200 μg of compound 5 reduced very significantly the number of eosinophilic granulocytes.
Figure 5:
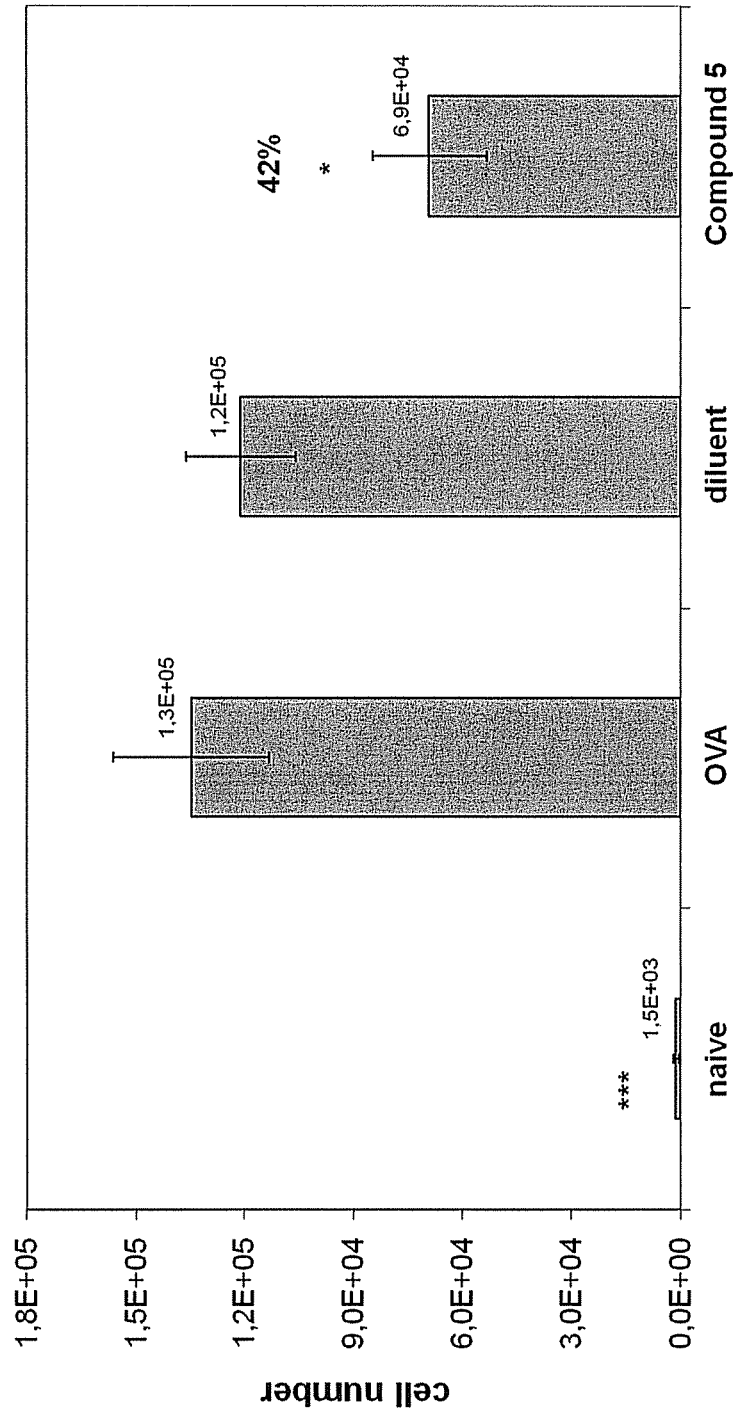
FIG. 5 shows the influence of compound 5 on the number of the CD4 positive T-cells, which migrated into the bronchial mucosa by the ovalbumin sensitization and which can be washed out into the lung rinsing solution by bronchial lavage (BAL). Here as well, the administration of 200 μg of compound 5 reduced very significantly the number of CD4 positive T-cells.

The invention claimed is:
1. A compound of the following formula:

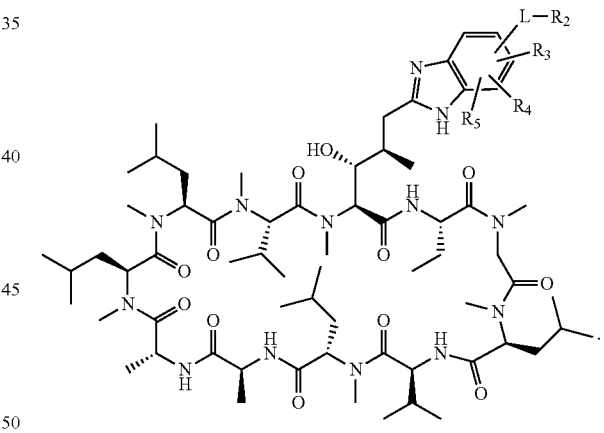

L selected from a group consisting of: a bond, —$CH_2$—, —$CH_2CH_2$—, —$CH_2CH_2CH_2$—, —$CH_2CH_2CH_2CH_2$—, —CH=CH—, —CH=CH$CH_2$—, —$CH_2$CH=CH—, —$CH_2CH_2$CH=CH—, —$CH_2$CH=CH$CH_2$—, —CH=CH$CH_2CH_2$, —O$CH_2$—, —O$CH_2CH_2$—, —O$CH_2CH_2CH_2$—, —O$CH_2$CH=CH—, —CONH—, —CONH$CH_2$— or —CONH$CH_2CH_2$—, —CONH$CH_2CH_2$O$CH_2CH_2$— and —CONH$CH_2CH_2$O$CH_2CH_2$O$CH_2CH_2$—;

$R_2$ selected from a group consisting of: a polar deprotonizable group $P_s$, a group $P_s'$ that under physiological conditions can be converted to the group $P_s$, a polar protonizable group $P_b$ and a group $P_b'$ that under physiological conditions can be converted to the group $P_b$;

R₃ selected from a group consisting of: H, (C1-C6)-alkyl, (C1-C6)-alkoxy, —OH, (C1-C6)-alklthio, (C1-C6)-alkylsulfonyl, —SH, —CF₃, —COOH, —COO((C1-C6)alkyl), —CONH₂, —CONH((C1-C6)alkyl), —CON((C1-C6)alkyl)₂, nitro, halogen, cyano, amino, (C1-C6)alkyl-amino and (C1-C6)dialkyl-amino;

R₄ and R₅ are independently of each other and selected from a group consisting of: H, (C1-C6)-alkyl, (C1-C6)-alkoxy, —CF₃ and halogen, or if R₄ and R₅ are situated on the ring in ortho position, then they can form together a —OCH₂O— or —OCH₂CH₂O— group; and pharmaceutically acceptable salts, as well as a tautomeric, enantiomeric or other stereoisomeric form thereof.

2. The compound according to claim 1, wherein R₂ is selected from the group consisting of: —COOH, —CONH₂, —CONHNH₂, —SO₃H, —SO₂NH₂, —COOCH₃, —COOCH₂CH₃, —COOCH₂CH₂CH₃, —COOCH₂CH₂CH₂CH₃, —COOCH₂CH(CH₂CH₃)₂, —COOCH(CH₃)₂, —COOC(CH₃)₃, —COOCH₂CH₂N(CH₃)₂, —COOCH₂CH₂(morpholin-4-yl),

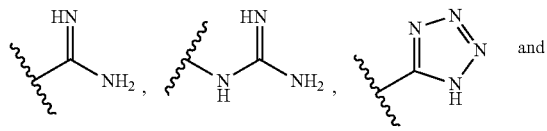

and

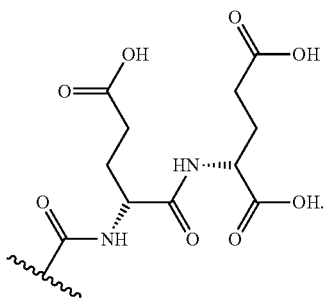

3. The compound according to claim 1, wherein L is selected from the group consisting of: a bond, —CH₂—, —CH₂CH₂—, —CH=CH—, —CONH— and —OCH₂—.

4. The compound according to claim 1, wherein R₃ is selected from the group consisting of: H, —COOH, —CH₃, —OCH₃, F, Cl, Br and CN.

5. The compound according to claim 1, wherein R₄ and R₅ are independently of each other H or F.

6. The compound according to claim 1, wherein the compound of the formula is one of the following:

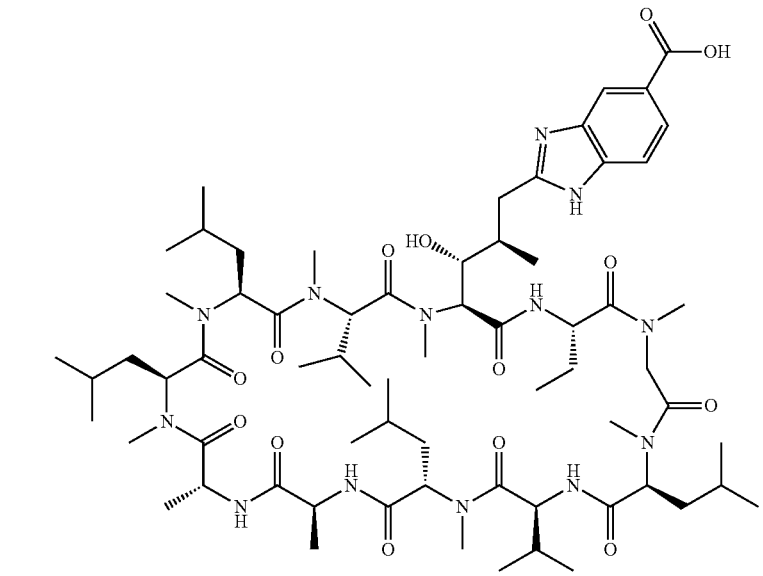

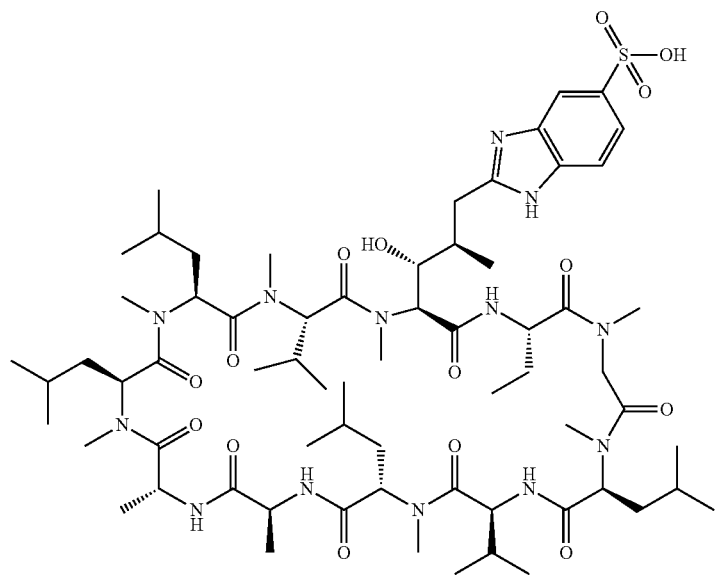
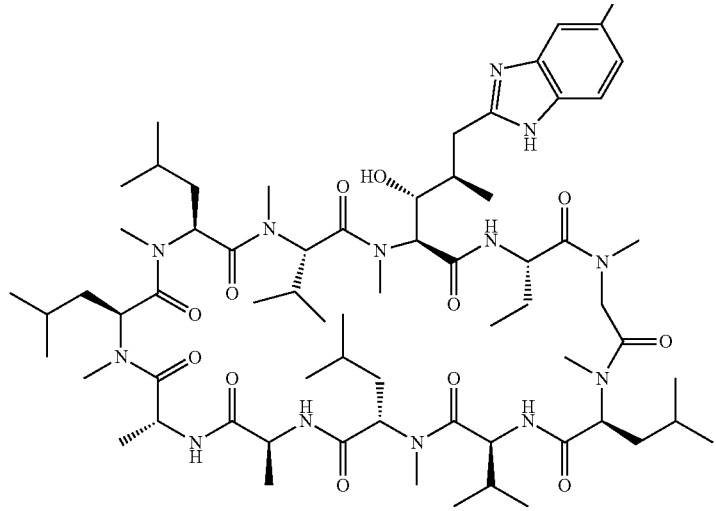

-continued
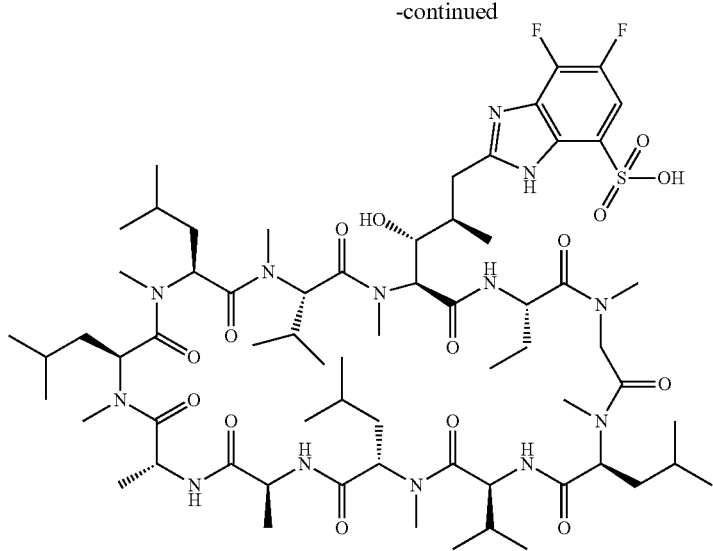
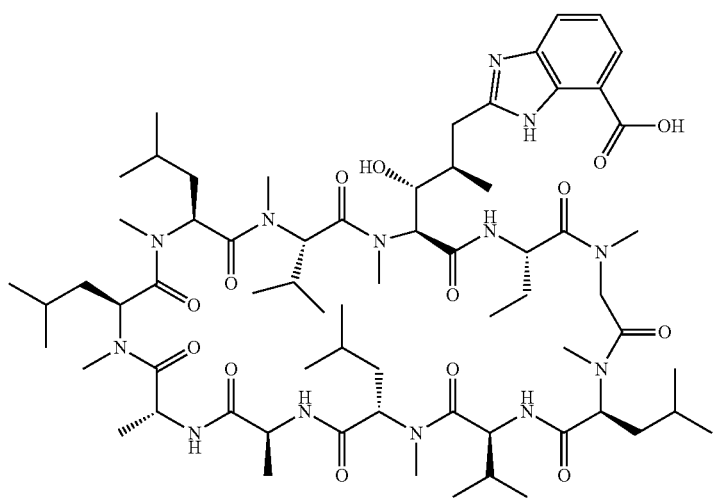
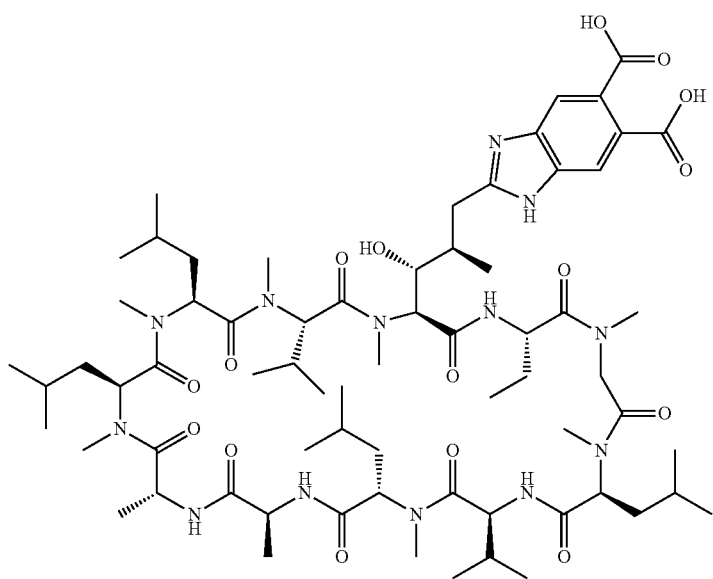

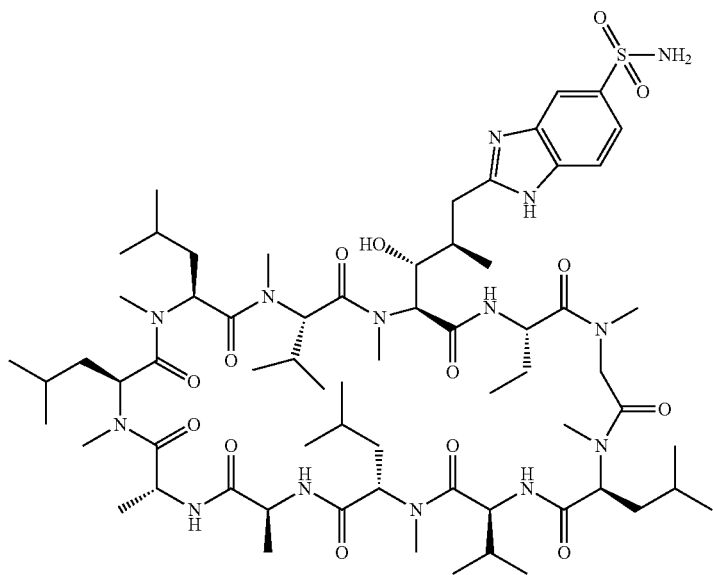
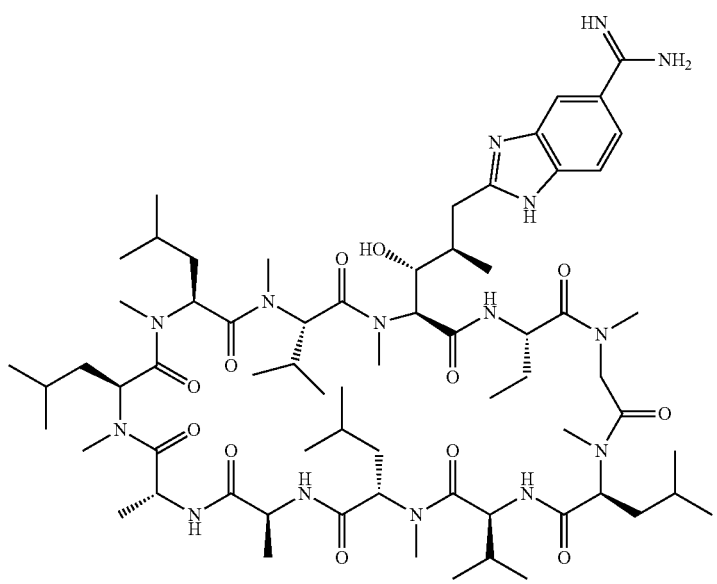

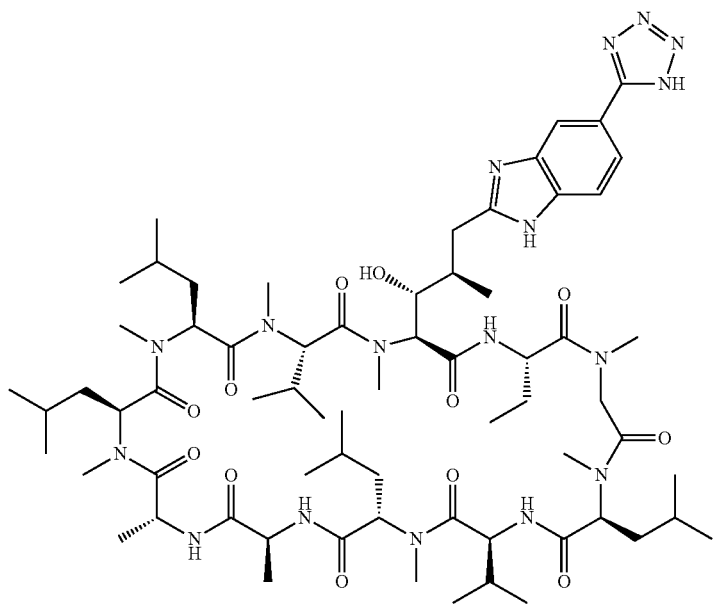 [SMILES: CC[C@@H]1NC(=O)[C@H]([C@H](O)[C@H](C)Cc2nc3cc(-c4nnn[nH]4)ccc3[nH]2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]
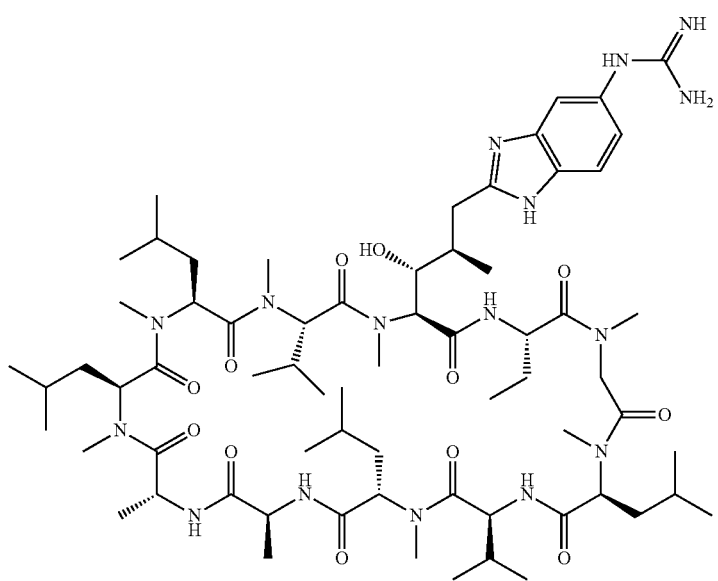 [SMILES: CC[C@@H]1NC(=O)[C@H]([C@H](O)[C@H](C)Cc2nc3cc(NC(=N)N)ccc3[nH]2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]

-continued

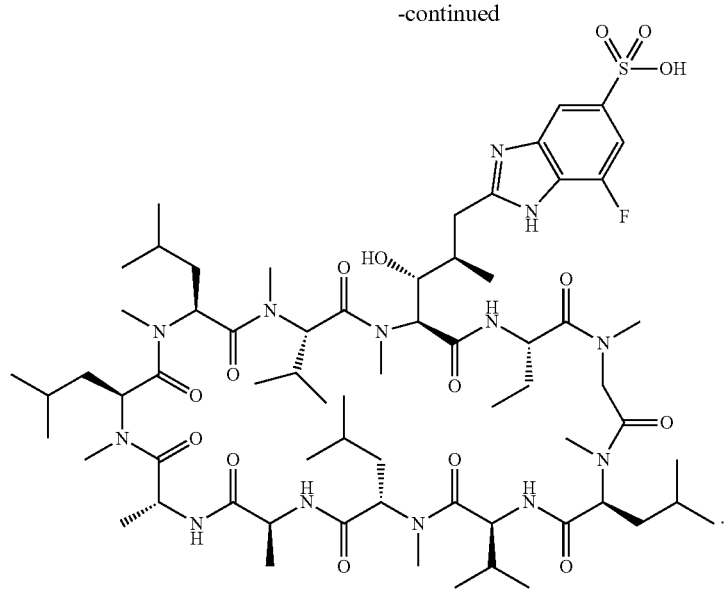

7. A pharmaceutical composition comprising the compound of formula of claim 1 with a suitable pharmaceutical carrier.

8. The compound according to claim 1 capable of treatment and/or diagnosis of:
   a) viral infections;
   b) acute and chronic inflammatory diseases;
   c) cancer consisting of: lung cancer, cancer of the bladder, hepatic cancer, pancreatic cancer, and breast cancer;
   d) degenerative muscle diseases;
   e) neurodegenerative diseases; and
   f) disorders which are associated with an impairment of calcium homeostasis.

* * * * *